United States Patent
Sunagawa et al.

(10) Patent No.: US 7,115,595 B2
(45) Date of Patent: Oct. 3, 2006

(54) CARBAPENEM COMPOUNDS

(75) Inventors: Makoto Sunagawa, Itami (JP); Akira Sasaki, Takarazuka (JP)

(73) Assignee: Dainippon Sumitomo Pharma Co., Ltd., Osaki (JP)

( * ) Notice: Subject to any disclaimer, the term of this patent is extended or adjusted under 35 U.S.C. 154(b) by 113 days.

(21) Appl. No.: 10/465,918

(22) PCT Filed: Dec. 25, 2001

(86) PCT No.: PCT/JP01/11345

§ 371 (c)(1), (2), (4) Date: Jun. 27, 2003

(87) PCT Pub. No.: WO02/053566

PCT Pub. Date: Jul. 11, 2002

(65) Prior Publication Data

US 2004/0063683 A1    Apr. 1, 2004

(30) Foreign Application Priority Data

Dec. 27, 2000 (JP) .............................. 2000-398392
Apr. 27, 2001 (JP) .............................. 2001-131637
Sep. 21, 2001 (JP) .............................. 2001-288295

(51) Int. Cl.
C07D 477/14 (2006.01)
A61K 31/407 (2006.01)
A61K 31/5377 (2006.01)
A61K 31/496 (2006.01)
A61P 31/04 (2006.01)

(52) U.S. Cl. .................. 514/210.09; 540/302; 540/200
(58) Field of Classification Search .................... None
See application file for complete search history.

(56) References Cited

U.S. PATENT DOCUMENTS 5,011,832 A * 4/1991 Dininno et al. ........ 514/210.09
5,025,006 A * 6/1991 Dininno et al. ................ 514/80
5,220,011 A * 6/1993 DiNinno et al. ............. 540/302
5,292,879 A * 3/1994 DiNinno et al. ............. 540/302
5,338,875 A    8/1994 DeCamp et al.
5,350,846 A * 9/1994 DiNinno et al. ............. 540/302
2004/0242874 A1 * 12/2004 Winkley et al. ............ 544/281

FOREIGN PATENT DOCUMENTS

EP    0 430 037 A2    6/1991
JP    03-223285       10/1991
JP    3-233285        10/1991

OTHER PUBLICATIONS

Hinks, Jeremy et al., "Preparation and reactivity of carbapenem-2-stannane" *Tetrahedron Letters*, vol. 41, No. 16, pp. 2995 to 2998, Apr. 2000.
JAGS 50(7), 5226-229 (2002), Yoshikawa et al.

* cited by examiner

Primary Examiner—Mark L. Berch
(74) Attorney, Agent, or Firm—Wenderoth, Lind & Ponack, L.L.P.

(57) ABSTRACT

Carbapenem compounds having a substituted phenyl or a substituted thienyl directly attached to the 3-position of carbapenem nucleus as represented by the formula:

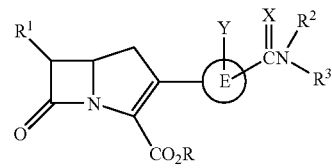

wherein Ring E is benzene ring or thiophene ring; $R^1$ is optionally OH-substituted $C_{1-3}$ alkyl; $R^2$ and $R^3$ represent each H, optionally substituted lower alkyl, etc.; R is H, or a group which is hydrolyzed in the living body to regenerate a carboxyl group, etc.; X is O or S; and Y represents H, lower alkyl, etc., or pharmaceutically acceptable salts thereof and medicaments containing said compound as the active ingredient. These compounds exhibit an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*.

7 Claims, No Drawings

CARBAPENEM COMPOUNDS

TECHNICAL FIELD

The present invention relates to a novel carbapenem compound. More particularly, the present invention relates to a carbapenem compound having a substituted phenyl group or a substituted thienyl group directly attached to the 3-position of the carbapenem nucleus. Further, the present invention relates to an antibacterial agent containing said carbapenem compound as the active ingredient.

BACKGROUND ART

The existing carbapenem compounds which have been developed and placed on the market are poorly absorbed at the digestive tract, and hence, they have been merely used in the clinical field in the form of an injection such as intravenous injections. However, in the clinical field, it is desirable to select several administration routes when a medicament is administered from the viewpoint of patient's conditions and therapeutic purpose, etc. Especially, oral antibacterial agents are more easily administered to a patient as compared with an injection, and are more convenient with respect to the home treatment of patients, so that the clinical usability of oral antibacterial agents is quite high. Accordingly, it has been strongly desired in the clinical field to develop carbapenem compounds having a wide antibacterial spectrum and a high antibacterial activity as well as being able to be orally administered.

DISCLOSURE OF INVENTION

An object of the present invention is to provide a carbapenem compound with a high oral absorbability, which exhibits an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*.

The present inventors have intensively studied, and have found that a compound having a substituted phenyl or substituted thienyl group directly attached to the 3-position of the carbapenem nucleus shows an excellent antibacterial activity, and it shows an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*. Further, they have also found that a compound having a group substituted onto the 2-carboxyl group, said group being capable of regenerating a carboxyl group by hydrolyzing in the living body, shows a good absorbability from the digestive tract by oral administration, and shows a potent antibacterial activity after converted into a 2-de-esterified compound in the living body, and further shows an excellent resistance to renal dehydropeptidase, and finally have accomplished the present invention.

BEST MODE FOR CARRYING OUT THE INVENTION

That is, the present invention relates to the following:

[1] A carbapenem compound of the formula:

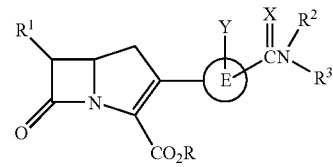

wherein Ring E is a benzene ring or a thiophene ring;

$R^1$ is an alkyl having 1 to 3 carbon atoms or a hydroxy-substituted alkyl having 1 to 3 carbon atoms;

$R^2$ and $R^3$ are independently a hydrogen atom, an optionally substituted lower allyl, an optionally substituted aryl, or $R^2$ and $R^3$ may combine each other together with the, nitrogen atom to form an optionally substituted 3- to 7-membered heterocyclic group;

R is a hydrogen atom or a group being hydrolyzed in the living body to regenerate a carboxyl group;

X is an oxygen atom or a sulfur atom;

Y is a hydrogen atom, a lower alkyl, a hydroxy group, a lower alkyloxy, a lower alkylthio, a lower alkylcarbonyl, a lower alkylcarbonyl-oxy, a lower alkyloxycarbonyl, carboxyl, a halogen atom, cyano, —$NR^4R^5$, —$CONR^4R^5$, —$OCONR^4R^5$, —$SO_2NR^4R^5$, —$NR^4SO_2NR^4R^5$ or —$NR^4CONR^4R^5$, or a lower alkyl substituted by a group selected from a hydroxy group, a lower alkyloxy, a lower alkylthio, a lower alkylcarbonyl, a lower alkyl-carbonyloxy, a lower alkyloxycarbonyl, carboxyl, a halogen atom, a cyano, —$NR^4R^5$, —$CONR^4R^5$, —$OCONR^4R^5$, —$SO_2NR^4R^5$, —$NR^4SO_2NR^4R^5$ and —$NR^4CONR^4R^5$, wherein the carboxyl, hydroxy and amino groups may optionally be protected by a suitable protecting group, and Ring E may be substituted by one or more Y groups, which are the same or different;

$R^4$ and $R^5$ are independently a hydrogen atom or a lower alkyl, or $R^4$ and $R^5$ may combine each other together with the nitrogen atom to form a pyrrolidine, a piperidine or an azepane, or a pharmaceutically acceptable salt thereof.

[2] The carbapenem compound according to the above [1] or a pharmaceutically acceptable salt thereof, wherein the group being hydrolyzed in the living body to regenerate a carboxyl group is a group of the formula:

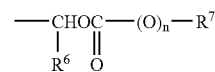

(in which $R^6$ is a hydrogen atom or a lower alkyl, $R^7$ is an optionally substituted lower alkyl, an optionally substituted lower cycloalkyl, and n is 0 or 1).

[3] The carbapenem compound according to the above [1] or a pharmaceutically acceptable salt thereof, wherein R is a group of the formula:

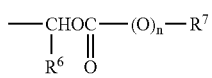

(in which $R^6$, $R^7$ and n are as defined in the above [2]).

[4] The carbapenem compound according to any one of the above [1 to [3] or a pharmaceutically acceptable salt thereof, wherein $R^1$ is a 1-hydroxyethyl.

[5] The carbapenem compound according to any one of the above [1] to [4] or a pharmaceutically acceptable salt thereof, wherein the group of the formula:

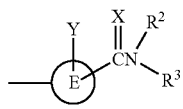

is a group selected from the following formula:

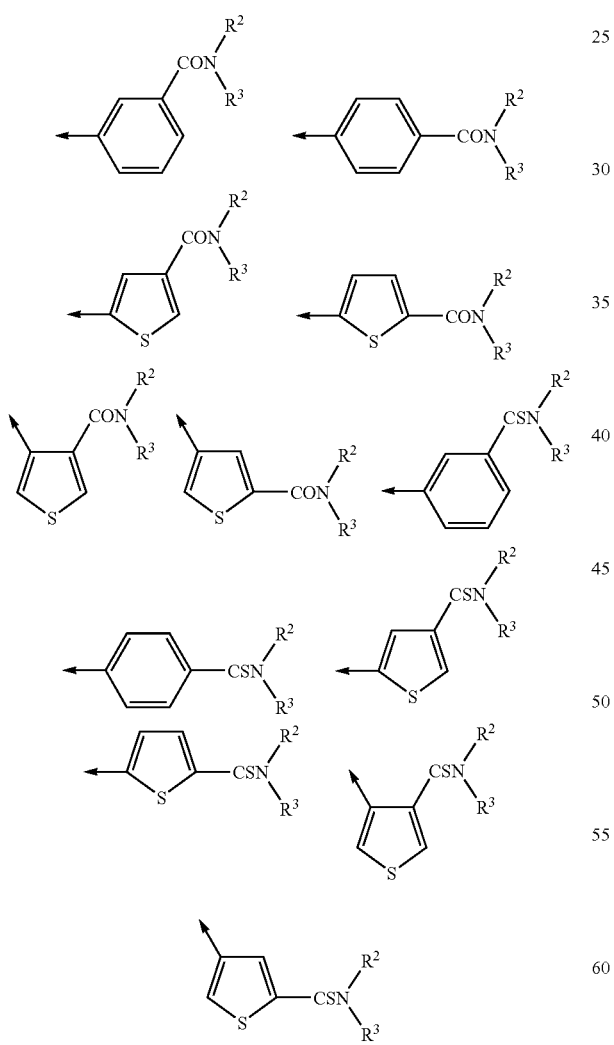

(in which Ring E, $R^2$, $R^3$ and Y are as defined in the above [1], and the arrowhead indicates the substitution position to the carbapenem nucleus).

[6] The carbapenem compound according to any one of the above [1] to [5] or a pharmaceutically acceptable salt thereof, wherein $R^2$ and $R^3$ are independently a hydrogen atom or a methyl group.

[7] The carbapenem compound according to any one of the above [1] to [6] or a pharmaceutically acceptable salt thereof, wherein $R^6$ is a hydrogen atom, $R^7$ is a tert-butyl group, and n is 0.

[8] A carbapenem compound selected from the following compounds or a pharmaceutically acceptable salt thereof:

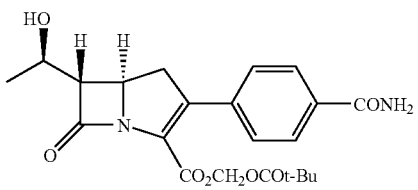

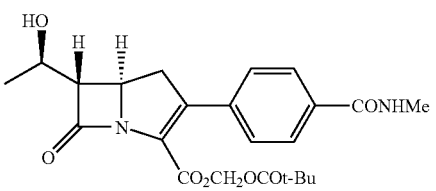

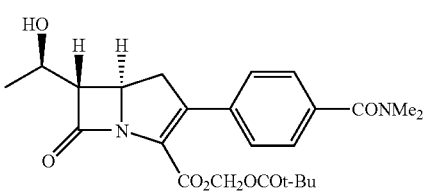

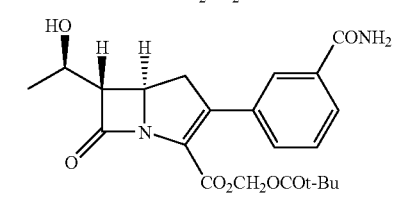

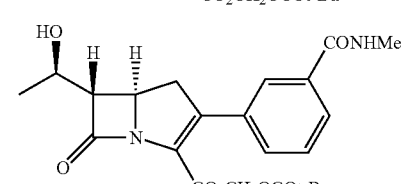

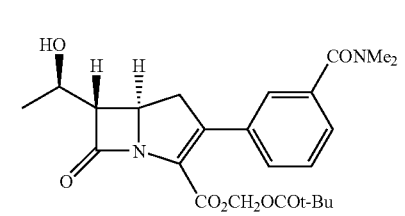

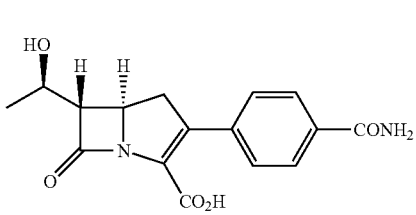

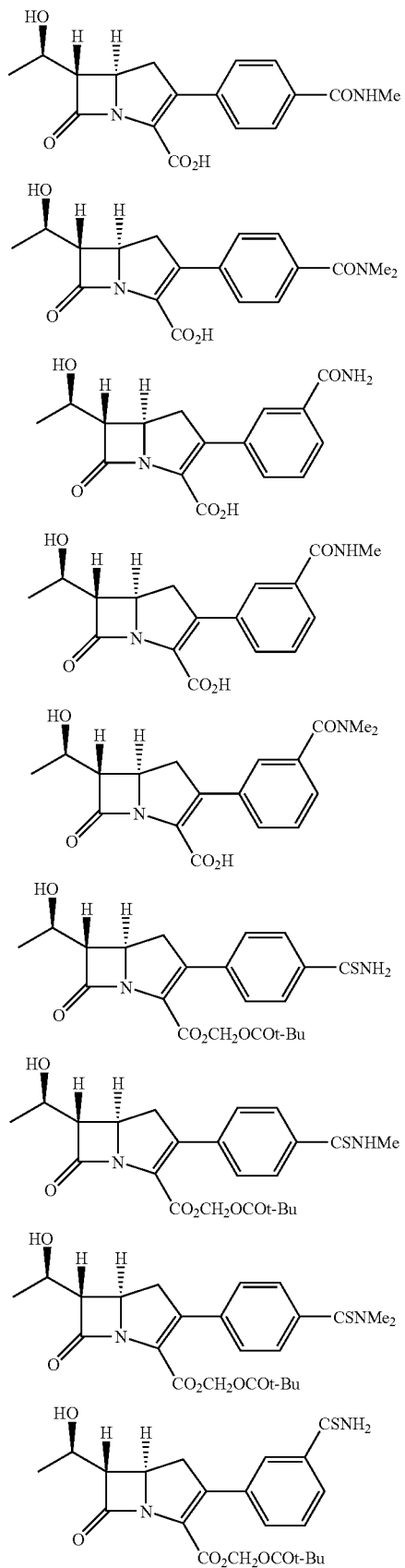
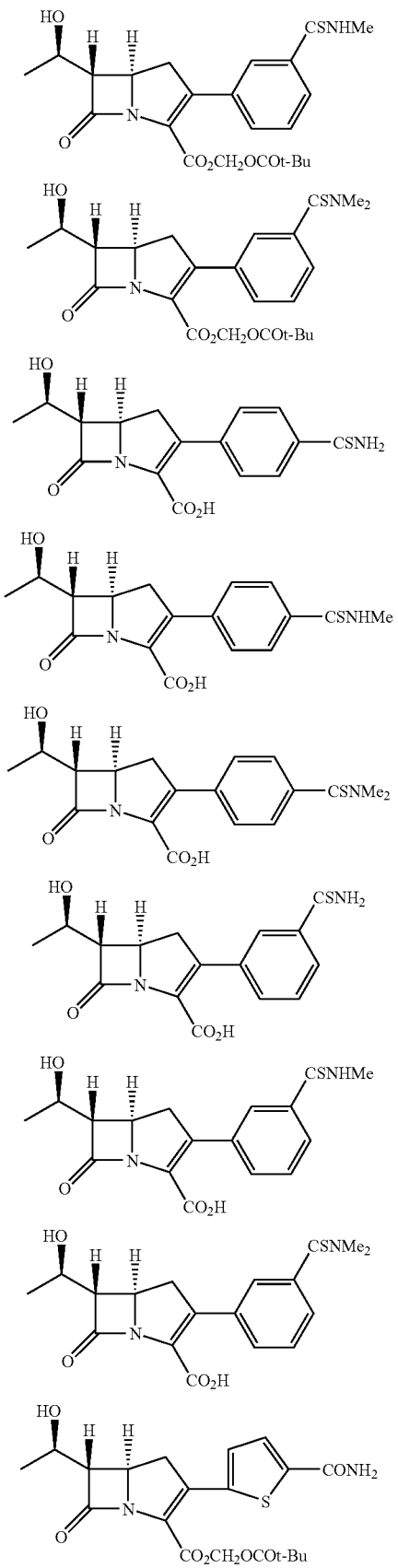

-continued
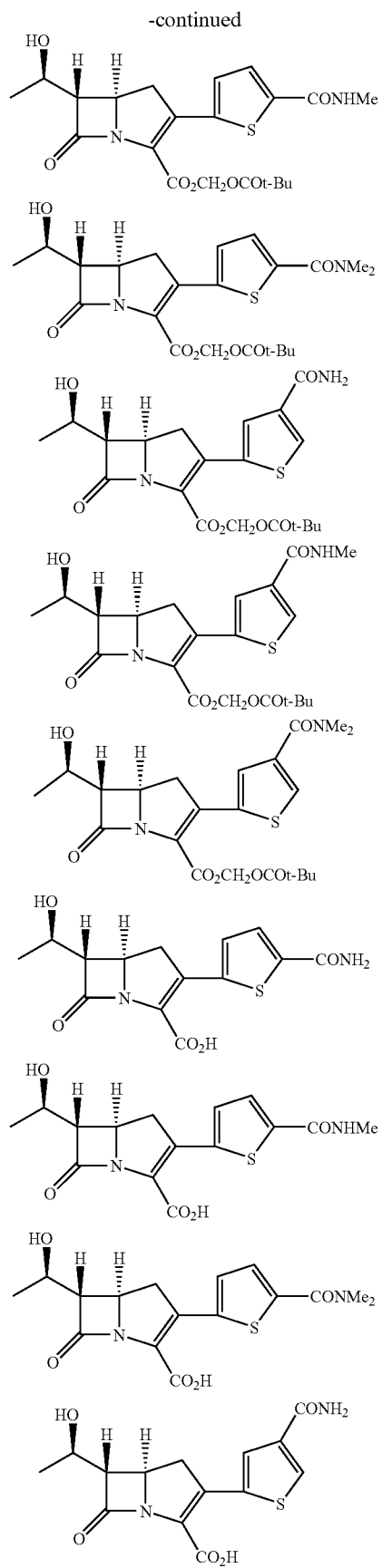
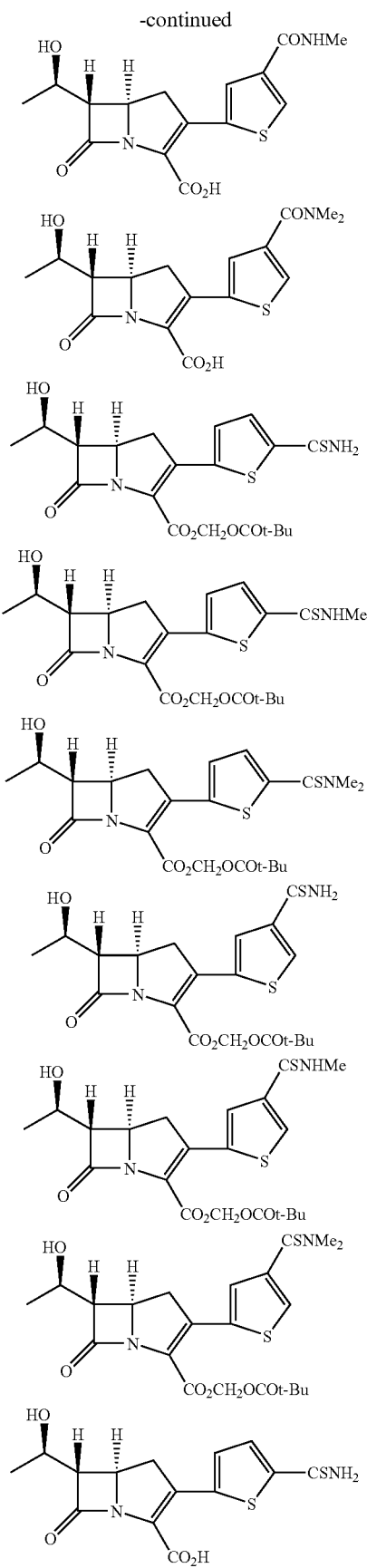

-continued

-continued

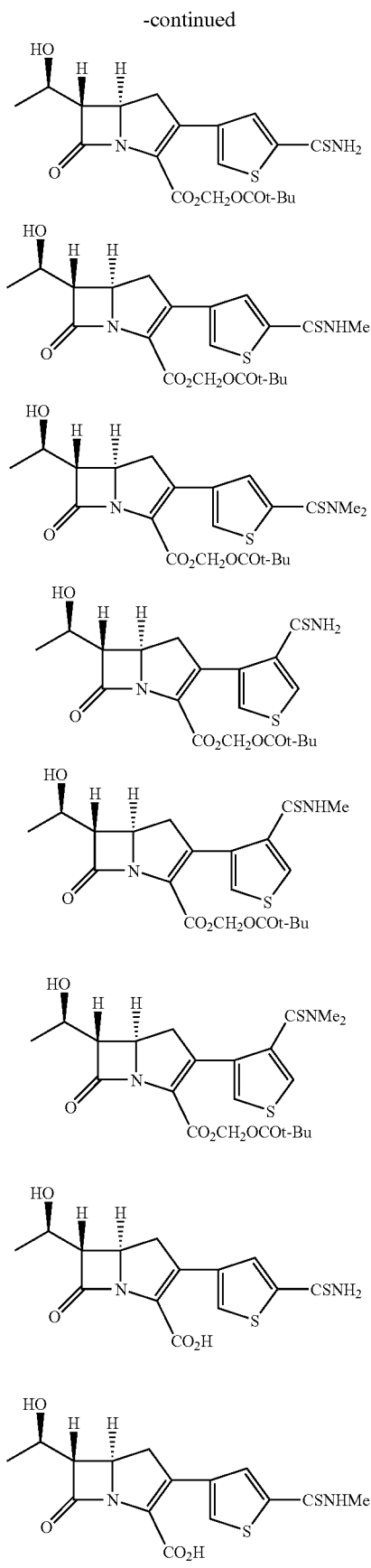

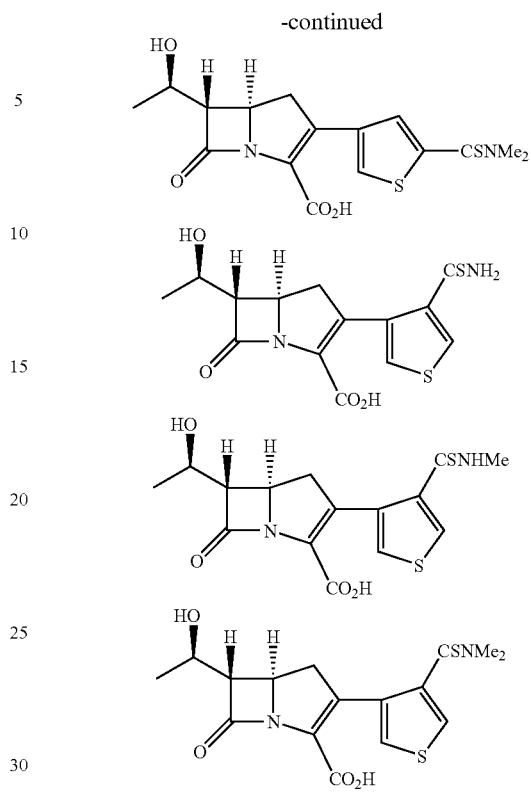

[9] A medicament, which comprises a carbapenem compound as set forth in any one, of the above [1] to [8] or a pharmaceutically acceptable salt thereof as the active ingredient.

[10] An antibacterial agent, which comprises a carbapenem compound as set forth in any one of the above [1] to [8] or a pharmaceutically acceptable salt thereof as the active ingredient.

The primary embodiment of the present invention concerns the above carbapenem compounds.

Each substituent represents the following meanings throughout the present specification and claims.

The "lower alkyl" includes a straight chain or branched chain alkyl having 1 to 6 carbon atoms, such as methyl, ethyl, n-propyl, isopropyl, n-butyl, isobutyl, tert-butyl, n-pentyl, n-hexyl, etc.

The "lower alkyl substituted by a hydroxy group" includes a straight chain or branched chain alkyl having 1 to 6 carbon atom, which is substituted by a hydroxy group, such as hydroxymethyl, 1-hydroxyethyl, 2-hydroxyethyl, 1-hydroxy-1-methylethyl, 1-hydroxypropyl, 2-hydroxypropyl, etc.

The "aryl" includes a 5- to 10-membered aromatic ring containing 0 to 3 hetero atoms, such as phenyl, pyridyl, pyrimidyl, pyridazyl, thienyl, furyl, pyrrolyl, imidazolyl, oxazolyl, isoxazolyl, thiazolyl, isothiazolyl, triazolyl, indolyl, benzothiazolyl, naphthyl, quinazolyl, isoquinazolyl, etc.

The "lower cycloalkyl" includes a cycloalkyl having 3 to 7 carbon atoms, such as cyclopropyl, cyclobutyl, cyclopentyl, cyclohexyl, cycloheptyl, etc.

The substituent of the "optionally substituted lower alkyl", "optionally substituted lower cycloalkyl" and "optionally substituted aryl" include, for example, a hydroxy group, a lower alkyloxy, a lower alkylthio, a lower alkylcarbonyl, a lower alkylcarbonyloxy, a lower alkyloxycarbonyl, a lower cycloalkyl, carboxyl, a halogen atom, cyano, —NR$^4$R$^5$, —CONR$^4$R$^5$, —OCONR$^4$R$^5$, —SO$_2$NR$^4$R$^5$, —R$^4$SO$_2$NR$^4$R$^5$, —NR$^4$CONR$^4$R$^5$ (R$^4$ and R$^5$ are as defined above), —COOCH$_2$OCOR$^8$ (R$^8$ is a lower alkyl), etc. and these substituents may optionally be protected by a suitable protecting group. The substitution position may be one or more of any chemically available positions.

The "lower alkyloxy" includes a straight chain or branched chain alkyloxy having 1 to 6 carbon atoms, such as methyloxy, ethyloxy, n-propyloxy, isopropyloxy, n-butyloxy, isobutyloxy, tert-butyloxy, n-pentyloxy, n-hexyloxy, etc.

The "lower alkylthio" includes a straight chain or branched chain alkylthio having 1 to 6 carbon atoms, such as methylthio, ethylthio, n-propylthio, isopropylthio, n-butylthio, isobutylthio, tert-butylthio, n-pentylthio, n-hexylthio, etc.

The "lower alkylcarbonyl" includes a straight chain or branched chain alkylcarbonyl having 2 to 7 carbon atoms, such as methyl-carbonyl, ethylcarbonyl, n-propylcarbonyl, isopropylcarbonyl, n-butylcarbonyl, isobutylcarbonyl, tert-butylcarbonyl, n-pentylcarbonyl, n-hexylcarbonyl, etc.

The "lower alkylcarbonyloxy" includes a straight chain or branched chain alkylcarbonyloxy having 2 to 7 carbon atoms, such as methylcarbonyloxy, ethylcarbonyloxy, n-propylcarbonyloxy, isopropyl-carbonyloxy, n-butylcarbonyloxy, isobutylcarbonyloxy, tert-butyl-carbonyloxy, n-pentylcarbonyloxy, n-hexylcarbonyloxy, etc.

The "lower alkyloxycarbonyl" includes a straight chain or branched chain alkyloxycarbonyl having 2 to 7 carbon atoms, such as methyloxycarbonyl, ethyloxycarbonyl, n-propyloxycarbonyl, isopropyl-oxycarbonyl, n-butyloxycarbonyl, isobutyloxycarbonyl, tert-butyloxy-carbonyl, n-pentyloxycarbonyl, n-hexyloxycarbonyl, etc.

The "halogen atom" is fluorine atom, chlorine atom, bromine atom and iodine atom, and preferable halogen atom is fluorine atom, chlorine atom, and bromine atom.

The "3- to 7-membered heterocyclic group" includes a saturated or unsaturated 3- to 7-membered heterocyclic group having 1 or 2 nitrogen atoms, 0 or 1 sulfur atom and 0 or 1 oxygen atom, such as aziridine, azetidine, pyrrolidine, dihydropyrrole, piperidine, tetrahydropyridine, piperazine, morpholine, thiomorpholine, azepane, tetrahydroazepine, tetrahydrodiazepine, hexahydrodiazepine, etc.

The substituent of the "optionally substituted 3- to 7-membered heterocyclic group" includes, for example, a lower alkyl, hydroxy group, a lower alkyloxy, a lower alkylcarbonyl, a lower alkylcarbonyloxy, a lower alkyloxycarbonyl, carboxyl, a halogen atom, a cyano, etc.

The "group being hydrolyzed in the living body to regenerate a carboxyl group" includes any groups being hydrolyzed in the living body to regenerate a carboxyl group such as groups being used for conversion into compounds called prodrugs. Preferable groups are groups of the formula:

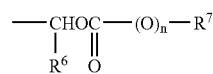

(in which R$^6$, R$^7$ and n are as defined above). Examples thereof are pivaloyloxymethyl, acetyloxymethyl, cyclohexylacetyloxymethyl, 1-methylcyclohexylcarbonyloxymethyl, ethyloxycarbonyloxy-1-ethyl, cyclohexyloxycarbonyloxy-1-ethyl, etc. Especially preferable one is pivaloyloxymethyl. In addition, other examples of the "groups being hydrolyzed in the living body to regenerate a carboxyl group" are a lower alkyl such as methyl, ethyl, etc., a lower alkyloxy-lower alkyl such as methyloxymethyl, ethyloxymethyl, 2-methyloxyethyl, 2-methyloxyethyloxymethyl, etc., and further (2-oxo-1,3-dioxol-4-yl)methyl, (5-methyl-2-oxo-1,3-dioxol-4-yl)methyl, (5-t-butyl-2-oxo-1,3-dioxol-4-yl)methyl, (5-phenyl-2-oxo-1,3-dioxol-4-yl) methyl, etc.

The protecting group for carboxyl may any conventional ones, and preferably a straight chain or branched chain alkyl having 1 to 5 carbon atoms such as methyl, ethyl, isopropyl, tert-butyl, etc., a halogenoalkyl having 1 to 5 carbon atoms such as 2-iodoethyl, 2,2,2-trichloroethyl, etc., an alkyloxymethyl having 1 to 5 carbon atoms such as methyloxymethyl, ethyloxymethyl, isobutyloxymethyl, etc., an aliphatic acyloxymethyl having 1 to 5 carbon atoms such as acetyloxymethyl, propionyloxymethyl, butyryloxymethyl, pivaloyloxymethyl, etc., a 1-(C$_1$–C$_5$)alkyloxycarbonyloxyethyl such as 1-ethyloxycarbonyloxyethyl, etc., a substituted aralkyl such as benzyl, p-methyloxybenzyl, o-nitrobenzyl, p-nitrobenzyl, etc., an alkenyl having 3 to 7 carbon atoms such as allyl, 3-methylallyl, etc., benzhydryl, phthalidyl. etc.

The protecting group for hydroxy group and amino group may be any conventional ones, and preferable ones are an alkyloxycarbonyl having 1 to 5 carbon atoms such as tert-butyloxycarbonyl, etc., a halogenoalkyloxycarbonyl having 1 to 5 carbon atoms such as 2-iodo-ethyloxycarbonyl, 2,2,2-trichloroethyloxycarbonyl, etc., an optionally substituted alkenyoxycarbonyl having 3 to 7 carbon atoms such as allyloxycarbonyl, etc., an optionally substituted aralkyloxycarbonyl such as benzyloxycarbonyl, p-methyloxybenzyloxycarbonyl, o-nitrobenzyloxycarbonyl, p-nitrobenzyloxycarbonyl, etc., a tri-lower alkylsilyl such as trimethylsilyl, triethylsilyl, tert-butyldimethylsilyl, etc.

The "aralkyl" of the "substituted aralkyl" and the "optionally substituted aralkyloxycarbonyl" includes a phenyl-lower alkyl, a naphthyl-lower alkyl, etc., and the substituent thereof includes a lower alkyloxy, nitro, etc., which substitutes on the phenyl ring or the naphthyl ring.

The pharmaceutically acceptable salt of the carbapenem compound of the present invention is a conventional non-toxic salt. Such salts include, as a salt with an intramolecular carboxylic acid, a salt with an inorganic base such as sodium, potassium, calcium, magnesium, ammonium, etc., a salt with an organic base such as triethylammonium, pyridinium, diisopropylammonium, etc. As a salt with an intramolecular base, a salt with an inorganic acid such as hydrochloric acid, sulfuric acid, phosphoric acid, etc., or a salt with an organic acid such as formic acid, acetic acid, oxalic acid, methanesulfonic acid, benzenesulfonic acid, etc. can be exemplified.

The carbapenem compound of the present invention, or a pharmaceutically acceptable salt thereof may be in the form of an anhydride thereof, a hydrate thereof, or a solvate thereof.

The secondary embodiment of the present invention concerns a medicament containing the carbapenem compound of the present invention as the active ingredient.

The carbapenem compound of the present invention exhibits a high antibacterial activity as well as an excellent absorbability when administered orally, and it also exhibits an excellent stability over dehydropeptidase-1 (DHP-1), and hence, it is proved that the carbapenem compound of the present invention make a clinically excellent antibiotic, especially an oral antibiotic.

The carbapenem compound of the present invention exhibits antibacterial activities against a wide variety of pathogenic bacteria including Gram-positive bacteria such as *Staphylococcus aureus*, *Staphylococcus epidermidis*, *Streptococcus pyogenes*, *Streptococcus pneumoniae*, *Enterococcus faecalis*, and Gram-negative bacteria such as *Escherichia coli*, the genus *Proteus*, *Kiebsiella pneumoniae*, *Haemophilus influenzae*, *Neisseria gonorrhoeae*, the genus *Branhamella*, and especially exhibits an excellent antibacterial activity against penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*.

It is well known that dehydropeptidase-I (DHP-I), a renal enzyme, can easily hydrolyze carbapenem compounds derived from natural resources, but the present compounds, which are also carbapenem compounds, are stable over DHP-I, and can be used alone, but a DHP-I inhibitor may be used together with the present compound, if necessary.

When used as an antibacterial agent in the treatment of infectious diseases caused by bacteria, the present carbapenem compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing the active ingredient with a conventional pharmaceutically acceptable carrier, excipient, binder, stabilizer, etc. by a conventional method. When administered in the form of an injection, a pharmaceutically acceptable buffering agent, solubilizer, isotonic agent, etc. may be added thereto.

The dosage of the present compound varies according to the symptoms, ages, body weights, the administration form, the frequency of the administration, etc., but it is usually in the range of 100 to 3000 mg per day for an adult, which is administered once or divided into several dosage units., Besides, the dosage of the present compound can be increased or decreased, if necessary.

The carbapenem compound of the present invention may be prepared by various conventional methods (Tetrahedron, 39, 2531–2549 (1983), Tetrahedron Letters, 31, 2853–2856 (1990), ibid. 34, 3211–3214 (1993), ibid. 36, 4563–4566 (1995), JP-B-4-40357, etc.). For instance, the following process is exemplified as one of them.

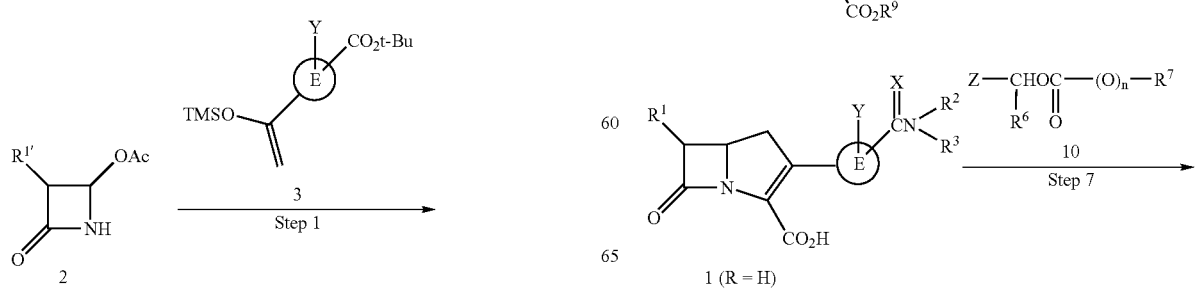

-continued

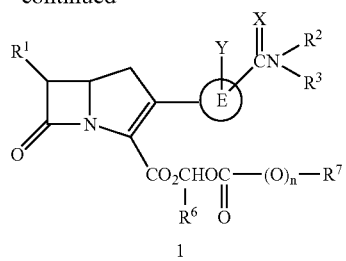

(R = a group being hydrolyzed in the living body to regenerate a carboxyl group)

(in which Ring E, $R^1$, $R^2$, $R^3$, $R^6$, $R^7$, X and Y are as defined above, $R^9$ is a protecting group for carboxyl group, $R^{1'}$ is an alkyl group having 1 to 3 carbon atoms, or an allyl group having 1 to 3 carbon atoms and being substituted by a protected hydroxy group, and Z is chlorine atom, bromine atom or iodine atom)

Step 1: Preparation of Compound 4

Compound 2 and Compound 3 are reacted in an inert solvent in the presence of an acid catalyst. The acid catalyst may be zinc chloride, zinc bromide, zinc iodide, tin tetrachloride, trifluoromethanesulfonyl trimethylsilyl ester, boron trifluoride diethyl ether complex, etc. The inert solvent may be methylene chloride, 1,2-dichloroethane, acetonitrile, monochlorobenzene, dioxane, tetrahydrofuran, benzene, toluene, etc. The reaction is carried out at a temperature of from −78° C. to +60° C., and preferably at a temperature of from −30° C. to +40° C.

The starting compound 3 may be prepared by enol-etherification of various acetophenone derivatives or acetylthiophene derivatives, which are prepared by conventional methods (e.g., according to methods disclosed in Shin-Jikken Kagaku Koza, vol. 14, Synthesis and Reaction of organic compounds [II] (1977) edited by The Chemical Society of Japan, published by Maruzene Co., Ltd., p. 751–875; ibid., No. 4 edition, Jikken Kagaku Koza, vol. 21, Organic Synthesis [III], Aldehyde Ketone Quinone (1991), by Maruzene Co., Ltd., p. 149–353).

Step 2: Preparation of Compound 6

Compound 4 and Compound 5A are heated under dehydration conditions in an inert solvent to give a corresponding hemiacetal compound. The inert solvent may be methylene chloride, 1,2-dichloroethane, monochlorobenzene, benzene, toluene, xylene, etc. The reaction is carried out at a temperature of from +50° C. to +200° C., and preferably at a temperature of from +80° C. to +150° C. In addition, according to a conventional method (e.g., a method disclosed in Journal of Organic Chemistry, 61, 7889–7894 (1996)), a corresponding hemiacetal compound is also prepared by reacting Compound 4 and Compound 5B in the presence of a base in an inert solvent, and subsequently reducing the resulting imide compound. The base may be triethylamine, diisopropylethylamine, N-methylmorpholine, etc. . . . The inert solvent for the imidation reaction may be methylene chloride, 1,2-dichloroethane, monochlorobenzene, etc. The imidation reaction is carried out at a temperature of from −50° C. to +50° C., and preferably at a temperature of from −30° C. to +30° C.

The reducing agent is preferably zinc, and the solvent for reduction is preferably a mixture of acetic acid and methylene chloride, acetic acid and 1,2-dichloroethane, acetic acid and monochlorobenzene, etc. The reduction is, carried out at a temperature of from −50° C. to +50° C., preferably at a temperature of from −30° C. to +30° C.

The resulting hemiacetal compound is subjected to chloridation with a chloride compound such as thionyl chloride, oxalyl chloride, phosphorus oxychloride, etc. to give Compound 6. The chloridation reaction is carried out in an inert solvent such as ether, tetrahydrofuran, methylene chloride, etc. in the presence of a base such as lutidine, pyridine, quinoline, diisopropylethylamine, triethylamine, etc. The reaction is carried out at a temperature of from −78° C. to +60° C., preferably at a temperature of from −30° C. to, 40° C.

Step 3: Preparation of Compound 7

Compound 6 is treated with triphenylphosphine in the presence of a base such as lutidine, pyridine, quinoline, diisopropylethylamine, triethylamine, etc. in an inert solvent such as tetrahydrofuran, dioxane, dimethoxyethane, etc. to give Compound 7. The reaction is carried out at a temperature of from 0° C. to +100° C., preferably at a temperature of from +10° C. to +70° C.

Step 4: Preparation of Compound 8

Compound 7 is treated with trifluoroacetic acid, hydrogen bromide/acetic acid, trifluoromethanesulfonic acid, etc., if necessary, in the presence of a reaction promoter such as anisole, dimethoxybenzene, etc., and converted into a carboxylic acid, which is further amidated or thioamidated by a conventional method. When $R^{1'}$ has a protecting group for hydroxyl group, said protecting group for hydroxyl group may possibly be removed simultaneously with conversion into a carboxylic acid. In such cases, the de-protected hydroxy group is protected again. The method for introduction of a protecting group is well known, for example, one disclosed in T. W. Greene: Protective Groups in Organic Synthesis, J. Wiley & Sons Inc., 1981.

Step 5: Preparation of Compound 9

The cyclization reaction of Compound 8 is carried out by heating it at a temperature of from +80° C. to 200° C. in an inert solvent such as benzene, toluene, xylene, etc. to give Compound 9.

Step 6: Preparation of Carbapenem Compound 1 (R=Hydrogen Atom)

Carbapenem compound 1 can be obtained by removing a protecting group for carboxyl group as $R^9$ of Compound 9, or when $R^{1'}$ has a protecting group of hydroxyl group, then by removing said protecting group for hydroxyl group. The removal of a protecting group is carried out by a well known method such as treatment with an acid, a base, a reducing agent, etc., for example, one disclosed in T. W. Greene: Protective Groups in Organic Synthesis, J. Wiley & Sons Inc., 1981.

Step 7: Preparation of Carbapenem Compound 1 (R=a Group Being Hydrolyzed in the Living Body to Regenerate a Carboxyl Group)

According to a conventional method, carbapenem compound 1 wherein R is a group being hydrolyzed in the living body to regenerate a carboxyl group can be obtained by introducing a group being hydrolyzed in the living body to regenerate a carboxyl group into the carbapenem compound 1 wherein R is a hydrogen atom. For instance, the carbapenem compound 1 wherein R is a group being hydrolyzed in the living body to regenerate a carboxyl group is obtained by treating the carbapenem compound 1 wherein R is a hydrogen atom, or a carboxylate thereof, with various halides represented by Compound 10 in the presence of a base such as diisopropylethylamine, triethylamine, 4-dimethylaminopyridine, potassium carbonate, sodium hydrogen carbonate, etc. if necessary. The reaction solvent may be any inert solvent and not necessarily specified, and the preferable solvent is dimethylformamide, dimethylsulfoxide, hexamethylphosphoramide, acetonitrile, dioxane, tetrahydrofuran, acetone, etc. The carboxylate may preferably be sodium salt or potassium salt, etc. The reaction is carried out at a temperature of from −78° C. to +100° C., preferably at a temperature of from −20° C. to +60° C.

In the above Steps, by using the starting Compound 5A or 5B wherein $R^9$ is a group being hydrolyzed in the living body to regenerate a carboxyl group, the carbapenem compound 1 wherein R is a group being hydrolyzed in the living body to regenerate a carboxyl group can also be prepared, after the above Steps.

After the reactions in the above Steps, the product thus obtained can be isolated by a conventional organic chemical technique, and when the product is soluble in water, then the reaction mixture is neutralized, and subjected to the column chromatography using absorbent resin, the fractions containing the desired compound are collected and lyophilized to obtain the reaction product.

The method for preparing the present carbapenem compound should not be construed to be limited to this process.

As shown in the following formula, the carbapenem compound of the present invention may contain optional isomers based on the asymmetric carbons at the 5- and 6-positions of the carbapenem nucleus.

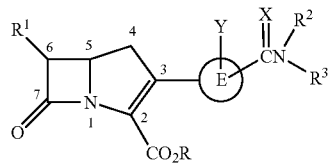

These isomers are expressed by a single formula for the sake of simplicity, and the present invention includes all of these isomers and a mixture thereof based on each asymmetric carbon atom. However, preferable isomer is compounds having an R-configuration at the 5-carbon atom ((5R,6R) or (5R,6S)), and more preferable one is a compound having a configuration of the formula:

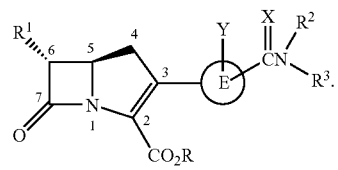

Moreover, when $R^1$ is 1-hydroxyethyl, the present carbapenem compound may have isomers having an R-configuration or an S-configuration at the 8-position, as shown in the following formula:

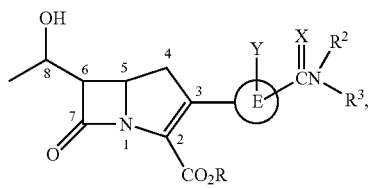

and the preferable one is ones having an R-configuration at the 8-position.

The substitution position of the amide group on the benzene ring or the thiophene ring at the 3-position may be any position. When Ring E is a benzene ring, the preferable substitution position is meta-position or papa-position.

Representative compounds of the carbapenem compounds of the present invention are exemplified by the following compounds 1 to 112.

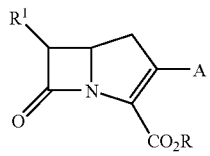

| Comp. No. | $R^1$ | R | A |
|---|---|---|---|
| 1 | —CH(OH)CH$_3$ | —CH$_2$OCOt-Bu | 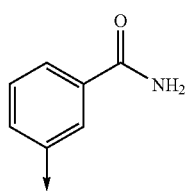 |

-continued
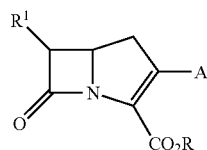
| Comp. No. | R¹ | R | A |
|---|---|---|---|
| 2 | —CH(OH)CH₃ | —CH₂OAc | 3-(C(O)NH₂)-C₆H₄— |
| 3 | —CH(OH)CH₃ | —CH₂OCOCH₂-cyclohexyl | 3-(C(O)NH₂)-C₆H₄— |
| 4 | —CH(OH)CH₃ | —CH₂OCO-(1-Me-cyclohexyl) | 3-(C(O)NH₂)-C₆H₄— |
| 5 | —CH(OH)CH₃ | —CH(Me)OCO₂Et | 3-(C(O)NH₂)-C₆H₄— |
| 6 | —CH(OH)CH₃ | —CH(Me)OCO₂-cyclohexyl | 3-(C(O)NH₂)-C₆H₄— |
| 7 | —CH(OH)CH₃ | —CH₂OCOt-Bu | 3-(C(O)NHMe)-C₆H₄— |
| 8 | —CH(OH)CH₃ | —CH₂OCOt-Bu | 3-(C(O)NMe₂)-C₆H₄— |

-continued
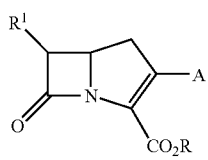
| Comp. No. | R¹ | R | A |
|---|---|---|---|
| 9 | —CH(OH)CH₃ | —CH(Me)OCO₂Et | 3-(C(O)NHMe)-phenyl |
| 10 | —CH(OH)CH₃ | —CH₂OAc | 4-(C(O)NHMe)-phenyl |
| 11 | —CH(OH)CH₃ | —CH₂OCOCH₂-cyclohexyl | 4-(C(O)NHMe)-phenyl |
| 12 | —CH(OH)CH₃ | —CH₂OCO-(1-Me-cyclohexyl) | 4-(C(O)NHMe)-phenyl |
| 13 | —CH(OH)CH₃ | —CH(Me)OCO₂Et | 4-(C(O)NHMe)-phenyl |
| 14 | —CH(OH)CH₃ | —CH(Me)OCO₂-cyclohexyl | 4-(C(O)NHMe)-phenyl |
| 15 | —CH(OH)CH₃ | CH₂OCOt-Bu | 4-(C(O)NH₂)-phenyl |
| 16 | —CH(OH)CH₃ | —CH₂OCOt-Bu | 4-(C(O)NMe₂)-phenyl |

-continued
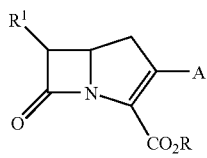
| Comp. No. | R¹ | R | A |
|---|---|---|---|
| 17 | —CH(OH)CH₃ | —CHOCO₂Et<br>\|<br>Me | 4-carbamoylphenyl |
| 18 | —CH(OH)CH₃ | —CH₂OCOt-Bu | 2-Me-4-carbamoylphenyl |
| 19 | —CH(OH)CH₃ | —CH₂OCOt-Bu | 2,5-diMe-4-carbamoylphenyl |
| 20 | —CH(OH)CH₃ | —CH₂OCOt-Bu | 2-Cl-4-carbamoylphenyl |
| 21 | —CH(OH)CH₃ | —CH₂OCOt-Bu | 2-F-4-carbamoylphenyl |
| 22 | —CH(OH)CH₃ | —CH₂OCOt-Bu | 2-Br-4-carbamoylphenyl |
| 23 | —CH(OH)CH₃ | —CHOCO₂Et<br>\|<br>Me | 2-F-4-carbamoylphenyl |
| 24 | —CH(OH)CH₃ | —H | 4-carbamoylphenyl |

-continued

![structure: carbapenem core with R¹ at 6-position, A at 3-position, CO₂R at 2-position]

| Comp. No. | R¹ | R | A |
|---|---|---|---|
| 25 | —CH(OH)CH₃ | —CH(Me)OCO₂Et | 2-Cl, 4-(C(O)NH₂) phenyl |
| 26 | —CH(OH)CH₃ | —CH₂OCOt-Bu | 2-CN, 4-(C(O)NH₂) phenyl |
| 27 | —CH(OH)CH₃ | —CH₂OCOCH₂-cyclohexyl | 3-(C(O)NHMe) phenyl |
| 28 | —CH(OH)CH₃ | —CH₂OCO-(1-methylcyclohexyl) | 3-(C(O)NHMe) phenyl |
| 29 | —CH(OH)CH₃ | —CH₂OAc | 3-(C(O)NHMe) phenyl |
| 30 | —CH(OH)CH₃ | —CH(Me)OCO₂-(piperidinyl) | 3-(C(O)NHMe) phenyl |
| 31 | —CH(OH)CH₃ | —CH₂OCOt-Bu | 2-OMe, 4-(C(O)NH₂) phenyl |
| 32 | —CH(OH)CH₃ | —H | 4-(C(O)NHEt) phenyl |

-continued

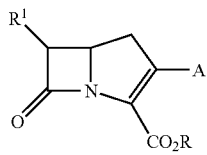

| Comp. No. | R¹ | R | A |
|---|---|---|---|
| 33 | —CH(OH)CH₃ | —CH₂OCOt-Bu | 2-(AcOCH₂)-4-(carbamoyl)phenyl |
| 34 | —CH(OH)CH₃ | —CH₂OAc | 4-(carbamoyl)phenyl |
| 35 | —CH(OH)CH₃ | —CH₂OCOCH₂-cyclohexyl | 4-(carbamoyl)phenyl |
| 36 | —CH(OH)CH₃ | —CH₂OCO-(1-methylcyclohexyl) | 4-(carbamoyl)phenyl |
| 37 | —CH(OH)CH₃ | —CH(Me)OCO₂-cyclohexyl | 4-(carbamoyl)phenyl |
| 38 | —CH(OH)CH₃ | —CH₂OCOt-Bu | 2-methyl-5-(carbamoyl)phenyl |
| 39 | —CH(OH)CH₃ | —CH₂OCOt-Bu | 2,4-dimethyl-5-(carbamoyl)phenyl |
| 40 | —CH(OH)CH₃ | —H | 4-(N,N-dimethylcarbamoyl)phenyl |

-continued
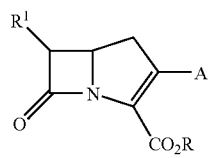
| Comp. No. | R¹ | R | A |
|---|---|---|---|
| 41 | —CH(OH)CH₃ | —CH₂OCOt-Bu | 2-Cl, 4-yl benzamide |
| 42 | —CH(OH)CH₃ | —CH₂OCOt-Bu | 2-F, 4-yl benzamide |
| 43 | —CH(OH)CH₃ | —CH₂OCOt-Bu | 2-Br, 4-yl benzamide |
| 44 | —CH(OH)CH₃ | —CH(Me)OCO₂Et | 2-F, 4-yl benzamide |
| 45 | —CH(OH)CH₃ | —CH₂OCOt-Bu | 2-CH₂OMe, 4-yl benzamide |
| 46 | —CH(OH)CH₃ | —CH₂OCOt-Bu | 2-CN, 4-yl benzamide |
| 47 | —CH(OH)CH₃ | —CH₂OCOt-Bu | 2-OMe, 4-yl benzamide |

-continued
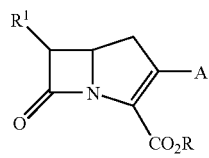
| Comp. No. | R¹ | R | A |
|---|---|---|---|
| 48 | —CH(OH)CH₃ | —H | 3-carbamoylphenyl (benzamide, meta-linked) |
| 49 | —CH(OH)CH₃ | —CH₂OCOt-Bu | 2-(AcOCH₂)-5-linked benzamide |
| 50 | —CH(OH)CH₃ | —CH₂OCOt-Bu | 2-(MeOCH₂)-5-linked benzamide |
| 51 | —CH(OH)CH₃ | —CH₂OCOt-Bu | 3-(N-ethylcarbamoyl)phenyl |
| 52 | —CH(OH)CH₃ | —CH₂OCOt-Bu | 2-carbamoylphenyl (ortho-linked benzamide) |
| 53 | —CH(OH)CH₃ | —CH₂OCOt-Bu | 5-Me-2-linked benzamide |
| 54 | —CH(OH)CH₃ | —CH₂OCOt-Bu | 4-MeO-2-linked benzamide |

-continued

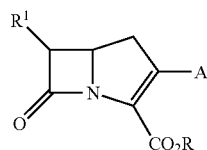

| Comp. No. | R¹ | R | A |
|---|---|---|---|
| 55 | —CH(OH)CH₃ | —CH₂OCOt-Bu | 3-(C(O)NHCH₂CH₂OH)-phenyl |
| 56 | —CH(OH)CH₃ | —H | 3-(C(O)NHMe)-phenyl |
| 57 | —CH(OH)CH₃ | —CH₂OCOt-Bu | 4-(aziridine-1-carbonyl)phenyl |
| 58 | —CH(OH)CH₃ | —CH₂OCOt-Bu | 4-(azetidine-1-carbonyl)phenyl |
| 59 | —CH(OH)CH₃ | —CH₂OCOt-Bu | 3-(pyrrolidine-1-carbonyl)phenyl |
| 60 | —CH(OH)CH₃ | —CH₂OCOt-Bu | 4-(piperidine-1-carbonyl)phenyl |
| 61 | —CH(OH)CH₃ | —CH₂OCOt-Bu | 4-(azepane-1-carbonyl)phenyl |
| 62 | —CH(OH)CH₃ | —CH₂OCOt-Bu | 4-(4-hydroxypiperidine-1-carbonyl)phenyl |

-continued

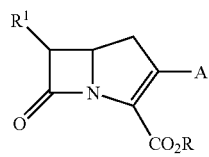

| Comp. No. | R¹ | R | A |
|---|---|---|---|
| 63 | —CH(OH)CH₃ | —CH₂OCOt-Bu | 4-(4-methylpiperazine-1-carbonyl)phenyl |
| 64 | —CH(OH)CH₃ | —H | 3-(N,N-dimethylcarbamoyl)phenyl |
| 65 | —CH(OH)CH₃ | —CH₂OCOt-Bu | 4-(4-methyl-1,4-diazepane-1-carbonyl)phenyl |
| 66 | —CH(OH)CH₃ | —CH₂OCOt-Bu | 4-(morpholine-4-carbonyl)phenyl |
| 67 | —CH(OH)CH₃ | —CH₂OCOt-Bu | 4-(thiomorpholine-4-carbonyl)phenyl |
| 68 | —CH(OH)CH₃ | —CH₂OCOt-Bu | 4-(2,5-dihydropyrrole-1-carbonyl)phenyl |
| 69 | —CH(OH)CH₃ | —CH₂OCOt-Bu | 4-(3,6-dihydro-2H-pyridine-1-carbonyl)phenyl |
| 70 | —CH₂CH₃ | —CH₂OCOt-Bu | 3-carbamoylphenyl |

-continued
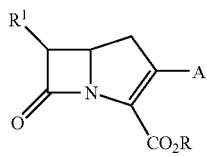
| Comp. No. | R¹ | R | A |
|---|---|---|---|
| 71 | —C(OH)(CH₃)₂ | —CH₂OCOt-Bu | 3-carbamoylphenyl |
| 72 | —CH(CH₃)₂ | —CH₂OCOt-Bu | 3-carbamoylphenyl |
| 73 | —CH(OH)CH₃ | —CH₂OCOt-Bu | 5-carbamoylthiophen-3-yl |
| 74 | —CH(OH)CH₃ | —CH₂Ac | 5-(N-ethylcarbamoyl)thiophen-2-yl |
| 75 | —CH(OH)CH₃ | —CH₂OCOCH₂-cyclohexyl | 5-carbamoylthiophen-2-yl |
| 76 | —CH(OH)CH₃ | —CH₂OCO-(1-methylcyclohexyl) | 5-carbamoylthiophen-2-yl |
| 77 | —CH(OH)CH₃ | —CH(Me)OCO₂Et | 5-carbamoylthiophen-2-yl |

-continued
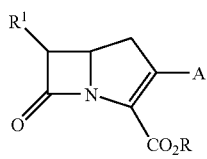
| Comp. No. | R¹ | R | A |
|---|---|---|---|
| 78 | —CH(OH)CH₃ | —CHOCO₂-cyclohexyl, Me | 5-(C(O)NH₂)-thiophen-2-yl |
| 79 | —CH(OH)CH₃ | —CH₂OCOt-Bu | 5-(C(O)NHMe)-thiophen-3-yl |
| 80 | —CH(OH)CH₃ | —CH₂OCOt-Bu | 5-(C(O)NMe₂)-thiophen-2-yl |
| 81 | —CH(OH)CH₃ | —CHOCO₂Et, Me | 5-(C(O)NHMe)-thiophen-2-yl |
| 82 | —CH(OH)CH₃ | —CH₂Ac | 5-(C(O)NHMe)-thiophen-3-yl |
| 83 | —CH(OH)CH₃ | —CH₂OCOCH₂-cyclohexyl | 5-(C(O)NH₂)-thiophen-3-yl |
| 84 | —CH(OH)CH₃ | —CH₂OCO-(1-Me-cyclohexyl) | 5-(C(O)NH₂)-thiophen-3-yl |
| 85 | —CH(OH)CH₃ | —CHOCO₂Et, Me | 5-(C(O)NHMe)-thiophen-3-yl |

-continued

[Structure: carbapenem core with R¹ at 6-position, CO₂R at 3-position, and A substituent at 2-position]

| Comp. No. | R¹ | R | A |
|---|---|---|---|
| 86 | —CH(OH)CH₃ | —CH(Me)OCO₂-cyclohexyl | 5-thienyl-3-C(O)NHMe |
| 87 | —CH(OH)CH₃ | —CH₂OCOt-Bu | 5-thienyl-3-C(O)NH₂ |
| 88 | —CH(OH)CH₃ | —CH₂Ac | 5-thienyl-3-C(O)NMe₂ |
| 89 | —CH(OH)CH₃ | —CH(Me)OCO₂Et | 5-thienyl-3-C(O)NMe₂ |
| 90 | —CH(OH)CH₃ | —CH₂OCOt-Bu | 3-Me-5-thienyl-2-C(O)NH₂ |
| 91 | —CH(OH)CH₃ | —CH₂OAc | 3,4-diMe-5-thienyl-2-C(O)NH₂ |
| 92 | —CH(OH)CH₃ | —CH₂OCOt-Bu | 3-Cl-5-thienyl-2-C(O)NH₂ |
| 93 | —CH(OH)CH₃ | —CH₂OCOt-Bu | 3-OMe-5-thienyl-2-C(O)NH₂ |
| 94 | —CH(OH)CH₃ | —CH₂OCOt-Bu | 3-CN-5-thienyl-2-C(O)NH₂ |

-continued

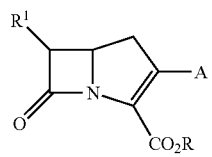

| Comp. No. | R¹ | R | A |
|---|---|---|---|
| 95 | —CH(OH)CH₃ | —CHOCO₂Et<br>    \|<br>    Me | 2-(methoxymethyl)-3-carbamoyl-thiophen-5-yl |
| 96 | —CH(OH)CH₃ | —H | 3-carbamoyl-thiophen-5-yl |
| 97 | —CH(OH)CH₃ | —CH₂OCOt-Bu | 3-(thiocarbamoyl)phenyl |
| 98 | —CH(OH)CH₃ | —CH₂OCOt-Bu | 4-(thiocarbamoyl)phenyl |
| 99 | —CH(OH)CH₃ | —CH₂OCOCH₂-cyclohexyl | 3-(thiocarbamoyl)phenyl |
| 100 | —CH(OH)CH₃ | —CH₂OCO-(1-methylcyclohexyl) | 4-(thiocarbamoyl)phenyl |
| 101 | —CH(OH)CH₃ | —CHOCO₂Et<br>    \|<br>    Me | 3-(thiocarbamoyl)phenyl |
| 102 | —CH(OH)CH₃ | —CHOCO₂-cyclohexyl<br>    \|<br>    Me | 4-(thiocarbamoyl)phenyl |

-continued
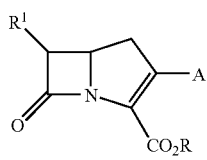
| Comp. No. | R¹ | R | A |
|---|---|---|---|
| 103 | —CH(OH)CH₃ | —CH₂OCOt-Bu | 3-(C(=S)NHMe)-phenyl |
| 104 | —CH(OH)CH₃ | —H | 3-(C(=S)NMe₂)-phenyl |
| 105 | CH(OH)CH₃ | —CH₂OCOt-Bu | 3-[C(=O)-N(piperazine)-N'-acetyl]-phenyl |
| 106 | CH(OH)CH₃ | —CH₂OCOt-Bu | 4-[C(=O)NH-(3-COOH-phenyl)]-phenyl |
| 107 | CH(OH)CH₃ | —CH₂OCOt-Bu | 3-[C(=O)NH-(4-OH-phenyl)]-phenyl |
| 108 | CH(OH)CH₃ | —CH₂OCOt-Bu | 4-[C(=O)NH-(2-OH-phenyl)]-phenyl |
| 109 | CH(OH)CH₃ | —CH₂OCOt-Bu | 4-[C(=O)NH-(2-OMe-phenyl)]-phenyl |

-continued

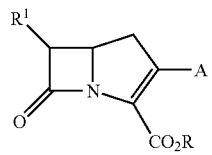

| Comp. No. | R¹ | R | A |
|---|---|---|---|
| 110 | CH(OH)CH$_3$ | —CH$_2$OCOt-Bu | ![structure] |
| 111 | CH(OH)CH$_3$ | —CH$_2$OCOt-Bu | ![structure] |
| 112 | CH(OH)CH$_3$ | —CH$_2$OCOt-Bu | ![structure] |

These exemplified compounds have stereoisomers as explained above, and there may also be stereoisomers based on R⁶. When R² and R³ combine each other together with the nitrogen atom to form an optionally substituted 3- to 7-membered heterocyclic group, there may be additional stereoisomers. The above exemplified compounds include all of these isomers as well.

EXAMPLES

The present invention is illustrated in more detail by Examples, but should not be construed to be limited thereto.

The following abbreviations are used in Examples as described hereinafter.

| | |
|---|---|
| Ph: | Phenyl group |
| Me: | Methyl group |
| n-Pr: | n-Propyl group |
| i-Pr: | i-Propyl group |
| t-Bu: | tert-Butyl group |
| Ac: | Acetyl group |
| ALOC: | Allyloxycarbonyl group |
| TMS: | Trimethylsilyl group |
| TBDMS: | tert-Butyl(dimethyl)silyl group |
| PNB: | p-Nitrobenzyl group |
| THF: | Tetrahydrofuran |

Example 1

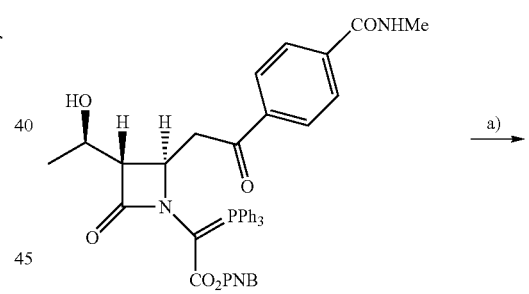 a)

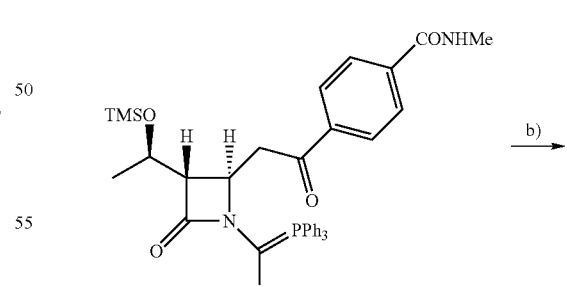 b)

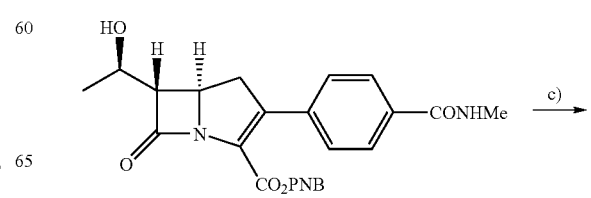 c)

-continued

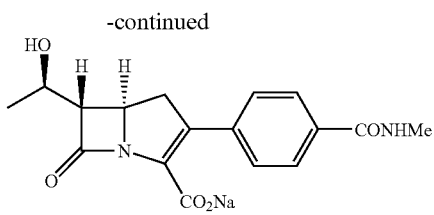

Step a)

To a solution of 4-nitrobenzyl [(2R,3S)-3-[(1R)-1-hydroxyethyl]-2-(2-{4-[(methylamino)carbonyl]phenyl}-2-oxoethyl)-4-oxo-1-azetidinyl]-(triphenylphosphoranylidene)acetate (844 mg) in THF (20 ml) was added N,O-bis(trimethylsilyl)acetamide (1.38 g) and 2,6-di-tert-butyl-p-cresol (25 mg) at room temperature, and the mixture was heated with stirring at bath temperature of 80° C. for 2 hours. The solvent was evaporated under reduced pressure to give 4-nitrobenzyl ((2R,3S)-2-(2-{4-[(methyl amino)carbonyl]phenyl}-2-oxoethyl)-4-oxo-3-{(1R)-1-[(trimethylsilyl)oxy]-ethyl}-1-azetidinyl)(triphenylphosphoranylidene)acetate, which was used in the subsequent step without further purification.

Step b)

To 4-nitrobenzyl ((2R,3S)-2-(2-{4-[(methylamino)carbonyl]phenyl}-2-oxoethyl)-4-oxo-3-{(1R)-1-[(trimethylsilyl)oxy]ethyl}-1-azetidinyl)(triphenylphosphoranylidene)acetate obtained in the above Step a) was added toluene (70 ml), and the mixture was heated with stirring at bath temperature of 120° C. for 2 hours. The solvent was evaporated under reduced pressure, and the resulting residue was dissolved again in ethyl acetate (100 ml). To the solution was added 0.1 N hydrochloric acid (0.5 ml) under ice-cooling, and the mixture was vigorously stirred. After the starting materials were consumed, an aqueous sodium hydrogen carbonate solution was added to the reaction mixture for neutralization, and the mixture was separated. The organic layer was washed with a saturated brine, and dried over anhydrous magnesium sulfate. The solvent was evaporated under reduced pressure, and the resulting residue was purified by silica gel column chromatography (chloroform/acetone) to give 4-nitrobenzyl (5R,6S)-6-[(1R)-1-hydroxyethyl]-3-{4-[(methylamino)carbonyl]phenyl}-7-oxo-1-azabicyclo[3.2.0]-hept-2-ene-2-carboxylate (204 mg).

$^1$H NMR (400 MHz, CDCl$_3$/CD$_3$OD=8/1) δ 1.36 (3H, d, J=6.3 Hz), 2.98 and 2.99 (combined 3H, each s), 3.18–3.41 (3H, m), 4.16–4.26 (1H, m), 4.35 (1H, dt, J=2.8 Hz and 9.4 Hz), 5.15–5.40 (2H, m), 7.39 (2H, d, J=8.5 Hz), 7.45 (2H, d, J=8.8 Hz), 7.74 (2H, d, J=8.5 Hz), 8.16. (2H, d, J=8.8 Hz).

Step c)

4-Nitrobenzyl (5R,6S)-6-[(1R)-1-hydroxyethyl]-3-{4-[(methylamino)carbonyl]phenyl}-7-oxo-1-azabicyclo[3.2.0]hept-2-ene-2-carboxylate (60 mg) obained in the above Step b) was dissolved in THF (6 ml) and ion-exchange water (4.7 ml), and thereto was added 0.1 N aqueous sodium hydrogen carbonate solution (1.3 ml). To the mixture was added 10% palladium on carbon (120 mg), and the mixture was subjected to hydrogenolysis for 30 minutes under atmospheric pressure at room temperature. The catalyst was removed by filtration, and washed with water, and chloroform was added to the filtrate, and extracted and separated (three times). The organic solvent in the aqueous layer was removed under reduced pressure, and the resultant was purified by polymer chromatography (CHP-20P). The fractions eluted with 0–2% aqueous THF solution were combined and lyophilized to give (5R,6S)-6-[(1R)-1-hydroxyethyl]-3-{4-[(methylamino)carbonyl]-phenyl}-7-oxo-1-azabicyclo[3.2.0]hept-2-ene-2-carboxylic acid sodium salt (18 mg).

$^1$H NMR (400 MHz, D$_2$O) δ 1.23 (3H, d, J=6.4 Hz), 2.83 (3H, s), 2.93–3.10 (1H, m), 3.29–3.43 (1H, m), 3.45 (1H, dd, J=2.8 Hz and 5.9 Hz), 4.07–4.33 (2H, m), 7.35 (2H, d, J=8.5 Hz), 7.60 (2H, d, J=8.5 Hz).

Example 2

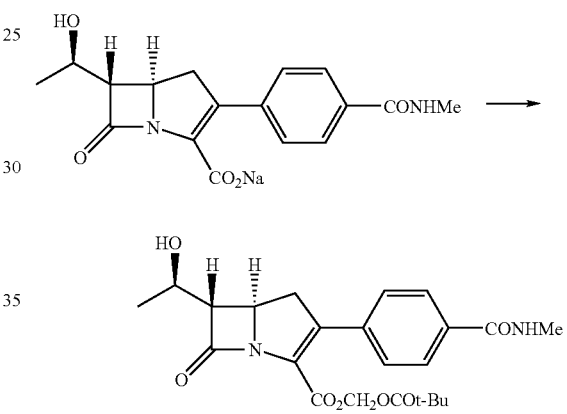

A solution of (5R,6S)-6-[(1R)-1-hydroxyethyl]-3-{4-[(methylamino)carbonyl]phenyl}-7-oxo-1-azabicyclo [3.2.0]hept-2-ene-2-carboxylic acid sodium salt (50 mg) in dry dimethylformamide (1 ml) was cooled with ice, and thereto was added pivaloyloxymethyl iodide (53 mg). The mixture was stirred at the same temperature for 1 hour. To the reaction solution were added ethyl acetate and ice-water, and separated. The organic layer was washed successively with a saturated brine (four times), an aqueous sodium hydrogen carbonate solution, an aqueous sodium thiosulfate solution, and a saturated brine, and dried over anhydrous magnesium sulfate. The solvent was evaporated under reduced pressure, and the residue was purified by silica gel thin layer chromatography (chloroform/methanol=9/1) to give [(2,2-dimethyl-propanoyl)oxy]methyl (5R,6S)-6-[(1R)-1-hydroxyethyl]-3-{4-[(methylamino)carbonyl]phenyl}-7-oxo-1-azabicyclo[3.2.0]hept-2-ene-2-carboxylate (27 mg).

$^1$H NMR (400 MHz, CDCl$_3$) δ 1.18 (9H, s), 1.37 (3H, d, J=6.3 Hz), 3.02 and 3.03 (combined 3H, each s), 3.15–3.41 (3H, m), 4.20–4.39 (2H, m), 5.70–5.90 (2H, m), 6.19. (1H, d., J=4.8 Hz), 7.39 (2H, d, J=8.4 Hz), 7.72 (2H, d, J=8.5 Hz).

Example 3

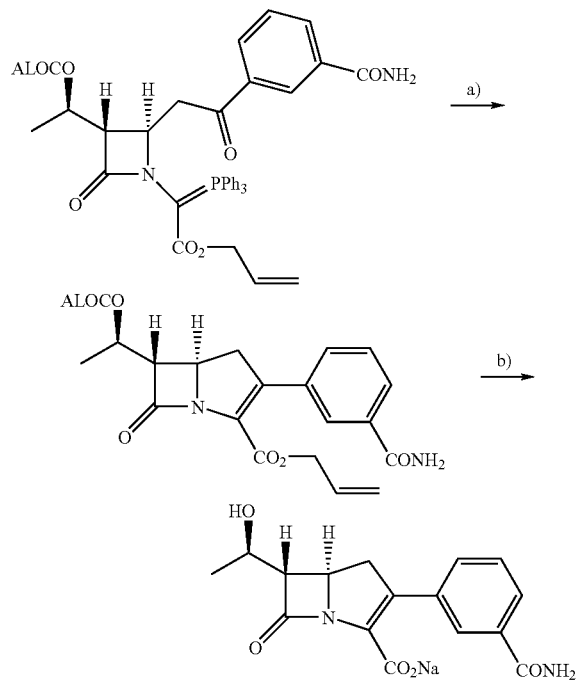

Step a)

To allyl ((2R,3S)-3-((1R)-1-{[(allyloxy)carbonyl]oxy}ethyl)-2-{2-[3-(aminocarbonyl)phenyl]-2-oxoethyl}-4-oxo-1-azetidinyl) (triphenylphosphoranylidene)acetate (324 mg) and 2,6-di-tert-butyl-p-cresol (10 mg) was added toluene (30 ml), and the mixture was heated with stirring at bath temperature of 100° C. for 2 hours, and then further heated with stirring at 130° C. for 2 hours. The mixture was purified by silica gel thin layer chromatography (ethyl acetate) to give allyl (5R,6S)-6-((1R)-1-{[(allyloxy)carbonyl]oxy}ethyl)-3-[3-(aminocarbonyl)phenyl]-7-oxo-1-azabicyclo[3.2.0]hept-2-ene-2-carboxylate (251 mg).

$^1$H NMR (400 MHz, CDCl$_3$) δ 1.49 (3H, d, J=6.3 Hz), 3.19–3.37 (2H, m), 3.43 (1H, dd, J=2.8 Hz and 8.3 Hz), 4.31 (1H, dt, J=2.9 Hz and 9.7 Hz), 4.58–4.77 (4H, m), 5.11–5.44 (5H, m), 5.80–6.02 (2H, m), 7.74–7.80 (1H, m), 7.86–7.92 (1H, m).

Step b)

Allyl (5R,6S)-6-((1R)-1-{[(allyloxy)carbonyl]oxy}ethyl)-3-[3-(aminocarbonyl)phenyl]-7-oxo-1-azabicyclo[3.2.0]hept-2-ene-2-carboxylate (80 mg) obtained in the above Step a) and aniline (339 mg) were dissolved in monochlorobenzene (4 ml), and thereto was added tetrakistriphenylphosphine palladium (11 mg) under ice-cooling. The mixture was stirred at the same temperature for 1 hour, and thereto were added 0.1 N aqueous sodium hydrogen carbonate solution (10 ml) and chloroform, and the mixture was separated. Then, chloroform was added to the aqueous layer, and the mixture was washed and separated twice. The organic solvent contained in the aqueous layer was removed under reduced pressure, and the resultant was purified by polymer chromatography (CHP-20P). The fractions eluted with water were combined, and lyophilized to give (5R,6S)-3-[3-(aminocarbonyl)phenyl]-6-[(1R)-1-hydroxyethyl]-7-oxo-1-azabicyclo[3.2.0]hept-2-ene-2-carboxylic acid sodium salt (8 mg).

$^1$H NMR (400 MHz, D$_2$O) δ 1.23 (3H, d, J=6.4 Hz), 2.99–3.09 (1H, m), 3.34–3.44 (1H, m), 3.46 (1H, dd, J=2.8 Hz and 6.0 Hz), 4.13–4.29 (2H, m), 7.36–7.44. (1H, m), 7.46–7.52 (1H, m), 7.60–7.67 (2H, m).

Example 4

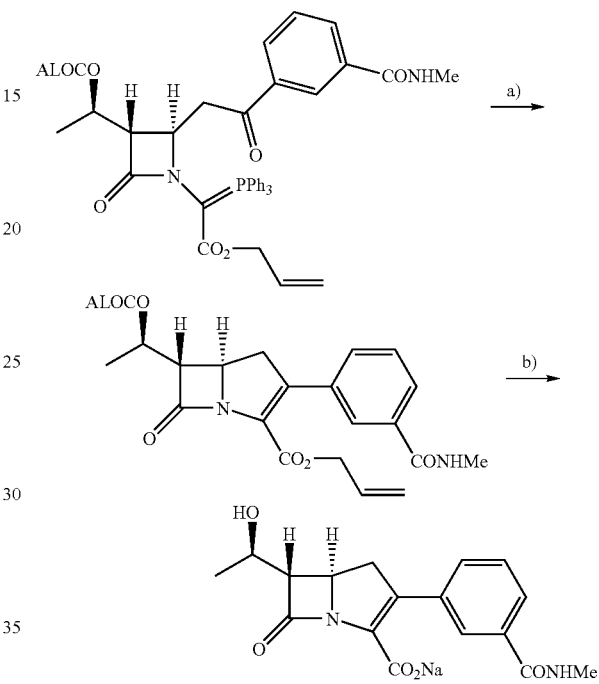

Step a)

Allyl (5R,6S)-6-((1R)-1-{[(allyloxy)carbonyl]oxy}ethyl)-3-{3-[(methylamino)carbonyl]phenyl}-7-oxo-1-azabicyclo[3.2.0]hept-2-ene-2-carboxylate (214 mg) was obtained from allyl [(2R,3S)-3-((1R)-1-{[(allyloxy) carbonyl]oxy}ethyl)-2-(2-{3-[(methylamino) carbonyl]phenyl}-2-oxoethyl)-4-oxo-1-azetidinyl](triphenylphosphoranylidene)acetate (312 mg) in a similar manner to Example 3-a).

$^1$H NMR (400 MHz, CDCl$_3$) δ 1.49 (3H, d, J=6.3 Hz), 2.97–3.06 (3H, m), 3.19–3.37 (2H, m), 3.43 (1H, dd, J=2.8 Hz and 8.3 Hz), 4.30 (1H, dt, J=2.9 Hz and 9.4 Hz), 4.57–4.77 (4H, m), 5.11–5.43 (5H, m), 5.80–6.01 (2H, m), 7.51–7.59 (2H, m), 7.78–7.84 (1H, m).

Step b)

(5R,6S)-6-[(1R)-1-Hydroxyethyl]-3-{3-[(methylamino)carbonyl]-phenyl}-7-oxo-1-azabicyclo[3.2.0]hept-2-ene-2-carboxylic acid sodium salt (20 mg) was obtained from allyl (5R,6S)-6-((1R)-1-{[(allyloxy)carbonyl]oxy}ethyl)-3-{3-[(methylamino)carbonyl]phenyl}-7-oxo-1-azabicyclo[3.2.0]hept-2-ene-2-carboxylate (70 mg) obtained in Step a) in a similar manner to Example 3-b).

$^1$H NMR (400 MHz, D$_2$O) δ 1.23 (3H, d, J=6.4 Hz), 2.83 (3H, s), 2.97–3.07 (1H, m), 3.33–3.43 (1H, m), 3.45 (1H, dd, J=2.8 Hz and 6.0 Hz), 4.13–4.29 (2H, m), 7.34–7.42 (1H, m), 7.43–7.49 (1H, m), 7.53–7.60 (2H, m).

Example 5

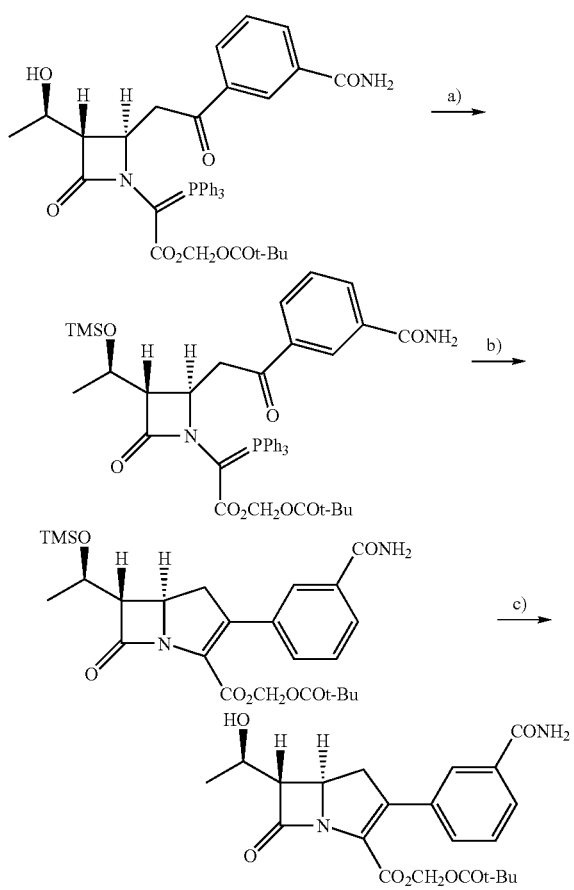

Step a)

{[2-{(2R,3S)-2-{2-[3-(Aminocarbonyl)phenyl]-2-oxoethyl}-3-[(1R)-1-hydroxyethyl]-4-oxo-1-azetidinyl}-2-(triphenylphosphoranylidene)acetyl]-oxy}methyl pivalate. (34.7 mg) and chlorotrimethylsilane (21 mg) were dissolved in dry THF (1.5 ml), and thereto was added dropwise triethylamine (20 mg) under ice-cooling. After the starting materials were consumed, the reaction solution was diluted with ethyl acetate, and poured into cold aqueous sodium hydrogen carbonate solution. The mixture was extracted and separated, and the organic layer was washed with brine, and dried over anhydrous sodium sulfate. The solvent was evaporated under reduced pressure to give {[2-((2R,3S)-2-{2-[3-(aminocarbonyl)phenyl]-2-oxoethyl}-4-oxo-3-{(1R)-1-[(trimethylsilyl)oxy]ethyl}-1-azetidinyl)-2-(triphenylphosphoranylidene)acetyl]-oxy}methyl pivalate, which was used in the subsequent reaction without further purification.

Step b)

[(2,2-Dimethylpropanoyl)oxy]methyl (5R,6S)-3-[3-(aminocarbonyl)phenyl]-7-oxo-6-{(1R)-1-[(trimethylsilyl)oxy]ethyl}-1-azabicyclo [3.2.0]-hept-2-ene-2-carboxylate (11 mg) was obtained from {[2-((2R,3S)-2-{2-[3-(aminocarbonyl)phenyl]-2-oxoethyl}-4-oxo-3-{(1R)-1-[(trimethylsilyl)oxy]ethyl}-1-azetidinyl)-2-(triphenylphosphoranylidene)acetyl]oxy}methyl pivalate obtained in Step a) in a similar manner to Example 3-a).

$^1$H NMR (400 MHz, CDCl$_3$) δ 0.15 (9H, s), 1.18 (9H, s), 1.29 (3H, d, J=6.2 Hz), 3.17–3.27 (2H, m), 3.28–3.38 (1H, m), 4.18–4.29 (2H, m), 5.80 (2H, s), 7.40–7.52 (2H, m), 7.76–7.85 (2H, m).

Step c)

[(2,2-Dimethylpropanoyl)oxy]methyl (5R,6S)-3-[3-(aminocarbonyl)phenyl]-7-oxo-6-{(1R)-1-[(trimethylsilyl)oxy]ethyl}-1-azabicyclo[3.2.0]-hept-2-ene-2-carboxylate (11 mg) obtained in Step b) was dissolved in ethyl acetate (2 ml) and THF (2 ml), and thereto was added 0.1N hydrochloric acid under ice-cooling to adjust the pH value thereof to the range of from pH 2 to pH 3. The mixture was vigorously stirred for 20 minutes, and the reaction solution was diluted with ethyl acetate, and poured into a cold aqueous sodium hydrogen carbonate solution. The mixture was extracted and separated, and the organic layer was dried over anhydrous magnesium sulfate, and evaporated under reduced pressure. The residue was purified by silica gel thin layer chromatography (ethyl acetate/acetone=4/1) to give [(2,2-dimethylpropanoyl)oxy]methyl (5R,6S)-3-[3-(aminocarbonyl)phenyl]-6-[(1R)-1-hydroxyethyl]-7-oxo-1-azabicyclo[3.2.0]hept-2-ene-2-carboxylate (9 mg).

$^1$H NMR (400 MHz, CDCl$_3$) δ 1.17. (9H, s), 1.36 (3H, d, J=6.3 Hz), 3.17–3.42 (3H, m), 4.20–4.38 (2H, m), 5.80 (2H, s), 7.40–7.52 (2H, m), 7.77–7.87 (2H, m).

Example 6

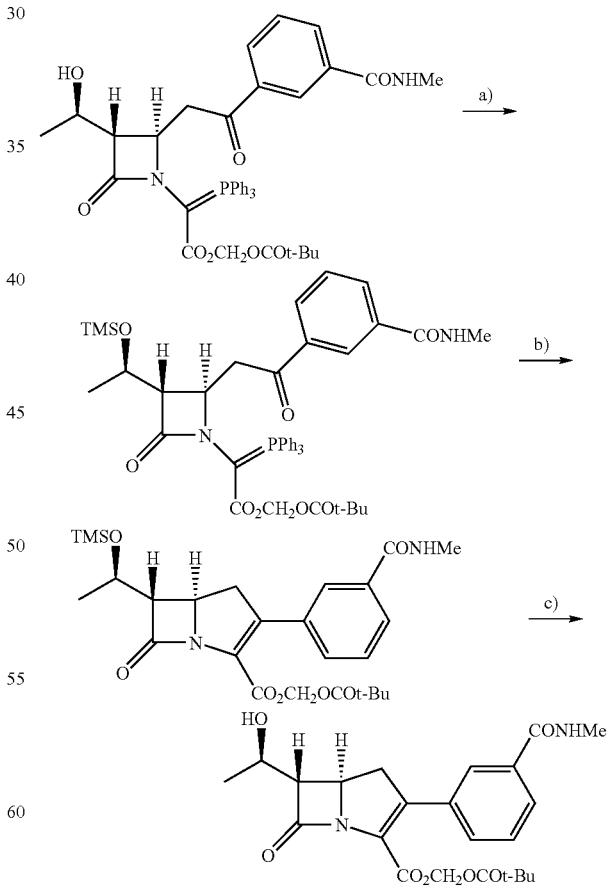

(2,2-Dimethylpropanoyl)oxy]methyl (5R,6S)-6-[(1R)-1-hydroxyethyl]-3-{3-[(methylamino)carbonyl]phenyl}-7-oxo-1-azabicyclo[3.2.0]-hept-2-ene-2-carboxylate (1.9 mg)

was obtained from {[2-[(2R,3S)-3-[(1R)-1-hydroxyethyl]-2-(2-{3-[(methylamino)carbonyl]phenyl}-2-oxoethyl)-4-oxo-1-azetidinyl]-2-(triphenylphosphoranylidene)acetyl]oxy}methyl pivalate (32 mg) in a similar manner to Example 5.

$^1$H NMR (400 MHz, CDCl$_3$) δ 1.18 (9H, s), 1.38 (3H, d, J=6.3 Hz), 3.02 and 3.03 (combined 3H, each s), 3.19–3.39 (3H, m), 4.23–4.37 (2H, m), 5.79 (2H, s), 7.39–7.48 (2H, m), 7.71–7.81 (2H, m).

Example 7

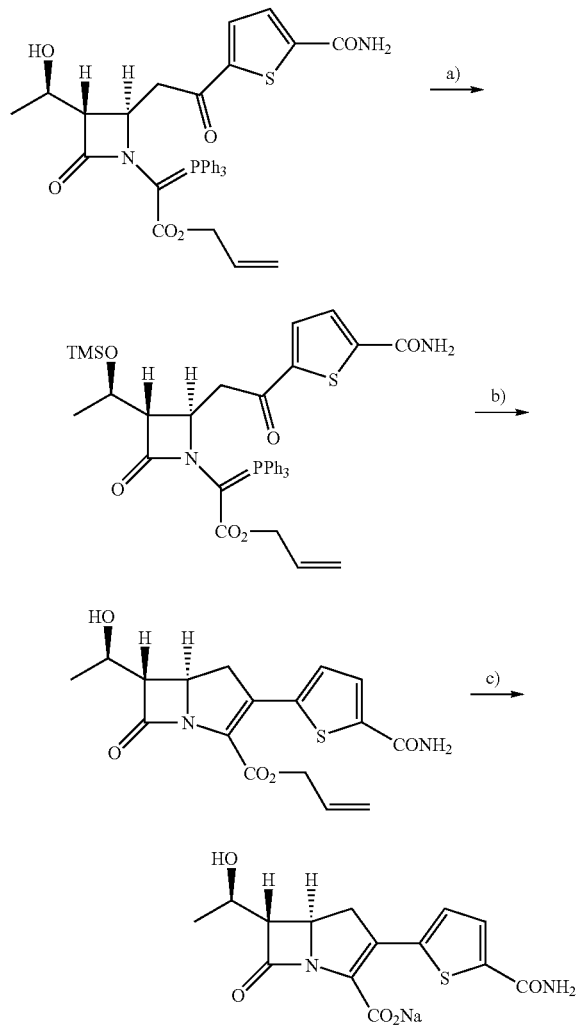

(5R,6S)-3-[5-(Aminocarbonyl)-2-thienyl]-6-[(1R)-1-hydroxyethyl]-7-oxo-1-azabicyclo[3.2.0]hept-2-ene-2-carboxylic acid sodium salt (9 mg) was obtained from allyl {(2R,3S)-2-{2-[5-(aminocarbonyl)-2-thienyl]-2-oxoethyl}-3-[(1R)-1-hydroxyethyl]-4-oxo-1-azetidinyl}(triphenylphosphoranylidene)acetate in a similar manner to Example 1 and Example 3.

$^1$H NMR (400 MHz, D$_2$O) δ 1.20 (3H, d, J=6.4 Hz), 3.13–3.34 (2H, m), 3.42 (1H, dd, J=3.0 Hz and 5.9 Hz), 4.10–4.25 (2H, m), 7.12 (1H, d, J=4.0 Hz), 7.51 (1H, d, J=4.1 Hz).

Example 8

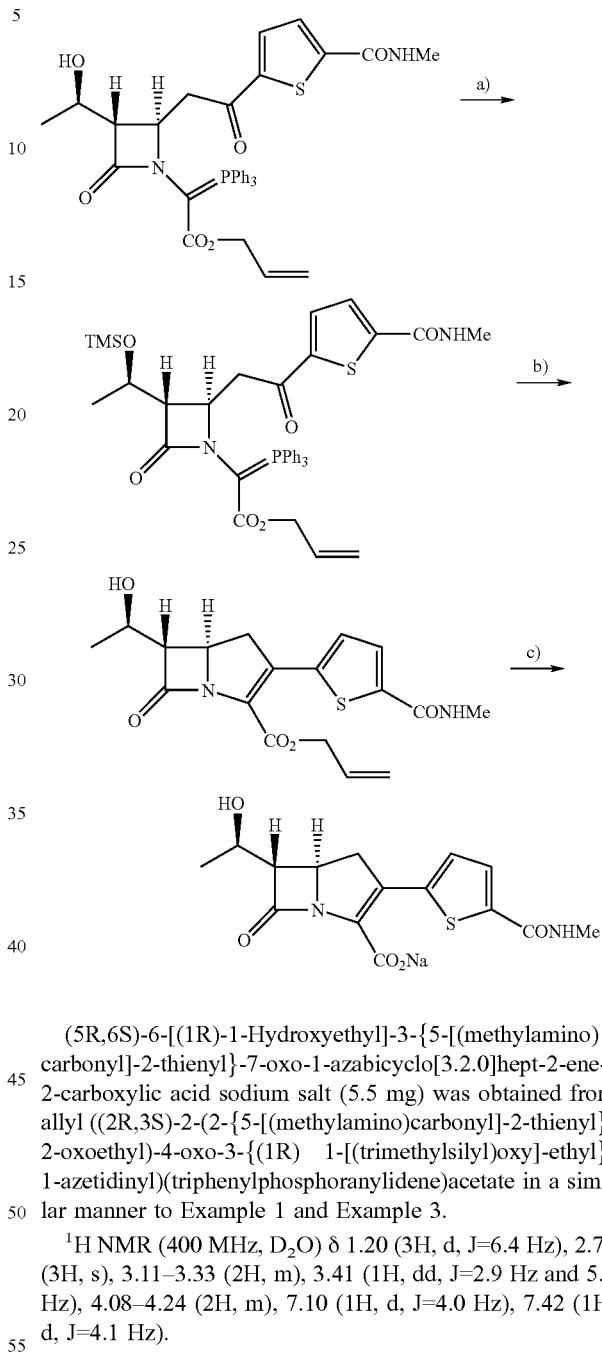

(5R,6S)-6-[(1R)-1-Hydroxyethyl]-3-{5-[(methylamino)carbonyl]-2-thienyl}-7-oxo-1-azabicyclo[3.2.0]hept-2-ene-2-carboxylic acid sodium salt (5.5 mg) was obtained from allyl ((2R,3S)-2-(2-{5-[(methylamino)carbonyl]-2-thienyl}-2-oxoethyl)-4-oxo-3-{(1R) 1-[(trimethylsilyl)oxy]-ethyl}-1-azetidinyl)(triphenylphosphoranylidene)acetate in a similar manner to Example 1 and Example 3.

$^1$H NMR (400 MHz, D$_2$O) δ 1.20 (3H, d, J=6.4 Hz), 2.78 (3H, s), 3.11–3.33 (2H, m), 3.41 (1H, dd, J=2.9 Hz and 5.8 Hz), 4.08–4.24 (2H, m), 7.10 (1H, d, J=4.0 Hz), 7.42 (1H, d, J=4.1 Hz).

Example 9

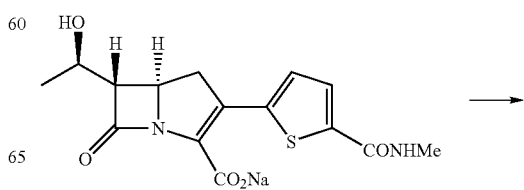

-continued

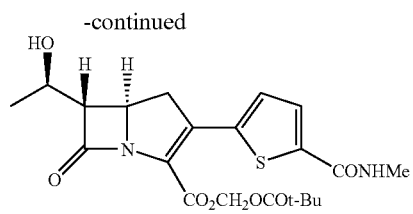

[(2,2-Dimethylpropanoyl)oxy]methyl (5R,6S)-6-[(1R)-1-hydroxyethyl]-3-{5-[(methyl amino)carbonyl]-2-thienyl}-7-oxo-1-azabicyclo-[3.2.0]hept-2-ene-2-carboxylate (7.9 mg) was obtained from (5R,6S)-6-[(1R)-1-hydroxyethyl]-3-{5-[(methylamino)carbonyl]-2-thienyl}-7-oxo-1-azabicyclo[3.2.0]hept-2-ene-2-carboxylic acid sodium salt (11 mg) in a similar manner to Example 2.

$^1$H NMR (400 MHz, CDCl$_3$) δ 1.23 (9H, s), 1.37 (3H, d, J=6.3 Hz), 2.99 and 3.00 (combined 3H, each s), 3.25 (1H, dd, J=2.8 Hz and 6.8 Hz), 3.31–3.53 (2H, m), 4.22–4.33 (2H, m), 5.89–6.07 (2H, m), 7.47–7.54 (2H, m).

Example 10

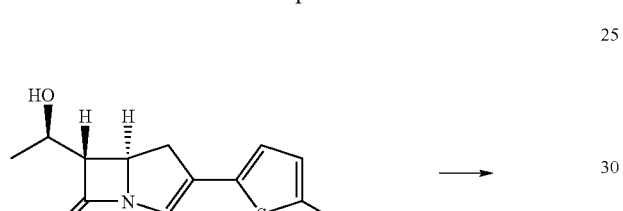

(5R,6S)-6-[(1R)-1-Hydroxyethyl]-3-{5-[(methylamino)carbonyl]-2-thienyl}-7-oxo-1-azabicyclo[3.2.0]hept-2-ene-2-carboxylate (2 mg) was obtained from (5R,6S)-6-[(1R)-1-hydroxyethyl]-3-{5-[(methylamino)carbonyl]-2-thienyl}-7-oxo-1-azabicyclo[3.2.0]hept-2-ene-2-carboxylic acid sodium salt (7 mg) in a similar manner to Example 2.

$^1$H NMR (400 MHz, CDCl$_3$) δ 1.38 (3H, d, J=6.3 Hz), 2.15 (3H, s), 3.00 and 3.01 (combined 3H, each s), 3.25 (1H, dd, J=2.8 Hz and 6.8 Hz), 3.31–3.55 (2H, m), 4.22–4.33 (2H, m), 5.87–6.02 (2H, m), 7.44–7.63 (2H, m).

Example 11

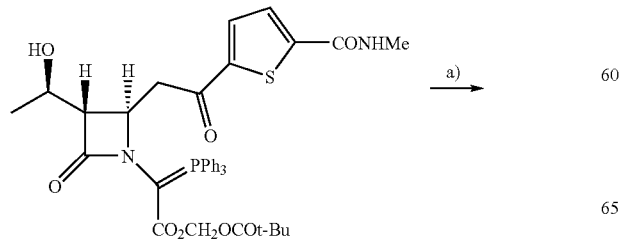

-continued

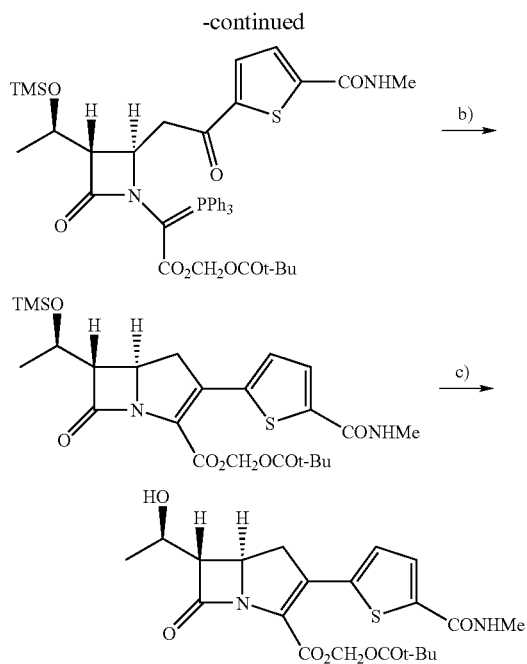

[(2,2-Dimethylpropanoyl)oxy]methyl (5R,6S)-6-[(1R)-1-hydroxyethyl]-3-{5-[(methylamino)carbonyl]-2-thienyl}-7-oxo-1-azabicyclo [3.2.0]-hept-2-ene-2-carboxylate (28 mg) was obtained from {[2-[(2R,3S)-3-[(1R)-1-hydroxyethyl]-2-(2-{5-[(methylamino)carbonyl]-2-thienyl}-2-oxoethyl)-4-oxo-1-azetidinyl]-2-(triphenylphosphoranylidene)acetyl]oxy}methyl pivalate (110 mg) in a similar manner to Example 5. The spectrum data were identical to those obtained in Example 9.

Example 12

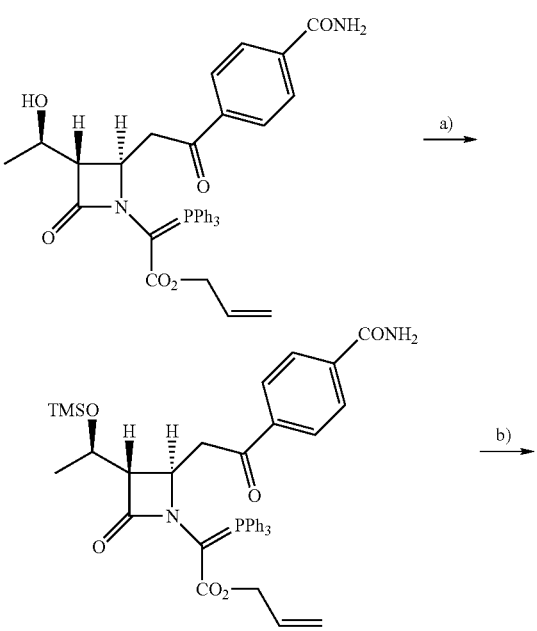

-continued

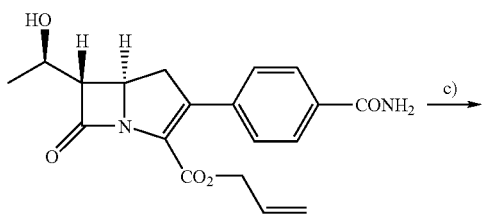

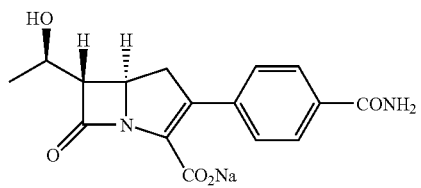

(5R,6S)-3-[4-(Aminocarbonyl)phenyl]-6-[(1R)-1-hydroxyethyl]-7-oxo-1-azabicyclo[3.2.0]hept-2-ene-2-carboxylic acid sodium salt was obtained from allyl {(2R,3S)-2-{2-[4-(aminocarbonyl)phenyl]-2-oxoethyl}-3-[(1R)-1-hydroxyethyl]-4-oxo-1-azetidinyl}(triphenylphosphoranylidene)acetate in a similar manner to Example 1 and Example 3.

$^1$H NMR (400 MHz, D$_2$O) δ 1.23 (3H, d, J=6.4 Hz), 2.78–2.93 (1H, m), 3.34–3.44 (1H, m), 3.46 (1H, dd, J=2.7 Hz and 5.8 Hz), 4.12–4.30 (2H, m), 7.37 (2H, d, J=8.4 Hz), 7.68 (2H, d, J=8.4 Hz).

Example 13

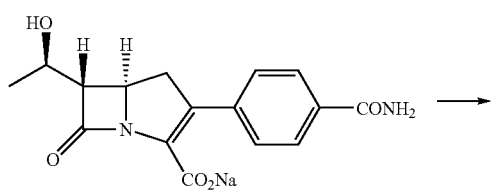

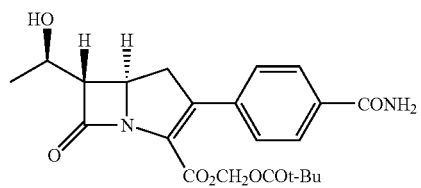

[(2,2-Dimethylpropanoyl)oxy]methyl (5R,6S)-3-[4-(aminocarbonyl)phenyl]-6-[(1R)-1-hydroxyethyl]-7-oxo-1-azabicyclo[3.2.0]hept-2-ene-2-carboxylate was obtained from (5R,6S)-3-[4-(aminocarbonyl)phenyl]-6-[(1R)-0.1-hydroxyethyl]-7-oxo-1-azabicyclo[3.2.0]hept-2-ene-2-carboxylic acid sodium salt in a similar manner to Example 2.

$^1$H NMR (400 MHz, CDCl$_3$) δ 1.18 (9H, s), 1.38 (3H, d, J=6.3 Hz), 3.16–3.42 (3H, m), 4.21–4.39 (2H, m), 5.73–5.88 (2H, m), 7.42 (2H, d, J=8.4 Hz), 7.79 (2H, d, J=8.4 Hz).

Example 14

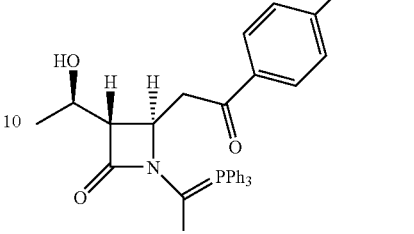

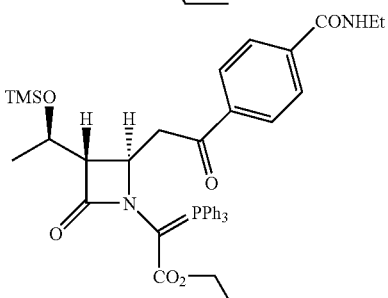

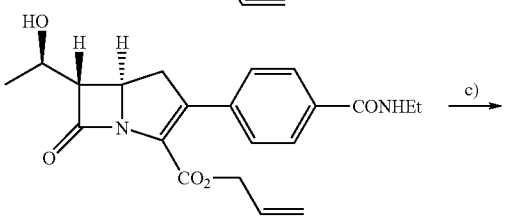

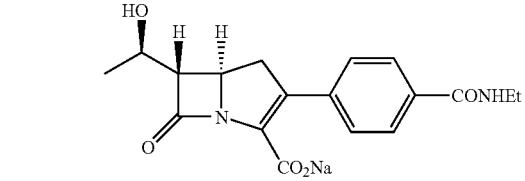

(5R,6S)-3-[4-(Ethylaminocarbonyl)phenyl]-6-[(1R)-1-hydroxyethyl]-7-oxo-1-azabicyclo[3.2.0]hept-2-ene-2-carboxylic acid sodium salt was obtained from allyl {(2R,3S)-2-{2-[4-(ethylaminocarbonyl)phenyl]-2-oxoethyl}-3-[(1R)-1-hydroxyethyl]-4-oxo-1-azetidinyl}(triphenylphosphoranylidene)acetate in a similar manner to Example 12.

$^1$H NMR (400 MHz, D$_2$O) δ 1.12 (3H, t, J=7.3 Hz), 1.23 (3H, d, J=6.4 Hz), 2.94–3.06 (1H, m), 3.25–3.41 (3H, m), 3.44 (1H, dd, J=2.8 Hz and 5.9 Hz), 4.13–4.26 (2H, m), 7.34 (2H, d, J=8.4 Hz), 7.59 (2H, d, J=8.4 Hz).

Example 15

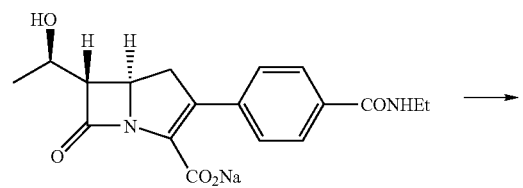

-continued

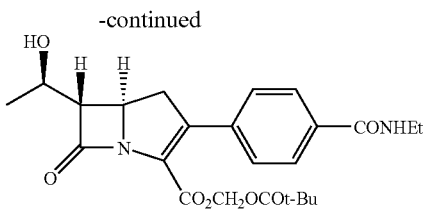

[(2,2-Dimethylpropanoyl)oxy]methyl (5R,6S)-3-[4-(ethylaminocarbonyl)phenyl]-6-[(1R)-1-hydroxyethyl]-7-oxo-1-azabicyclo[3.2.0]hept-2-ene-2-carboxylate was obtained from (5R,6S)-3-[4-(ethylaminocarbonyl)phenyl]-6-[(1R)-1-hydroxyethyl]-7-oxo-1-azabicyclo[3.2.0]hept-2-ene-2-carboxylic acid sodium salt in a similar manner to Example 2.

$^1$H NMR (400 MHz, CDCl$_3$) δ 1.18 (9H, s), 1.26 (3H, t, J=7.3 Hz), 1.37 (3H, d, J=6.3 Hz), 3.15–3.41 (3H, m), 3.43–3.57 (2H, m), 4.22–4.38 (2H, m), 5.72–5.89 (2H, m), 6.12 (1H, broad s), 7.39 (2H, d, J=8.5 Hz), 7.73 (2H, d, J=8.4 Hz).

Example 16

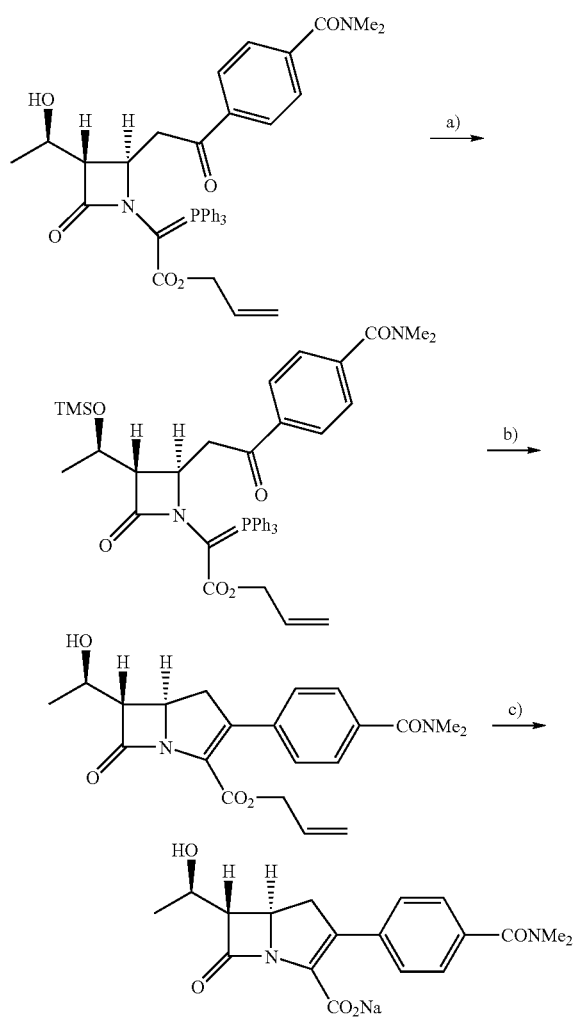

(5R,6S)-3-[4-(Dimethylaminocarbonyl)phenyl]-6-[(1R)-1-hydroxyethyl]-7-oxo-1-azabicyclo[3.2.0]hept-2-ene-2-carboxylic acid sodium salt was obtained from allyl {(2R,3S)-2-{2-[4-(dimethylaminocarbonyl)phenyl]-2-oxoethyl}-3-[(1R)-1-hydroxyethyl]-4-oxo-1-azetidinyl}-(triphenylphosphoranylidene)acetate in a similar manner to Example 12 except that sodium 2-ethylhexanoate was used instead of aniline in Step c).

$^1$H NMR (400 MHz, D$_2$O) δ 1.23 (3H, d, J=6.4 Hz), 2.94 (3H, s), 2.96–3.08 (1H, m), 3.01 (3H, s), 3.33–3.43 (1H, m), 3.46 (1H, dd, J=2.8 Hz and 6.0 Hz), 4.11–4.29 (2H, m), 7.27–7.42 (4H, m).

Example 17

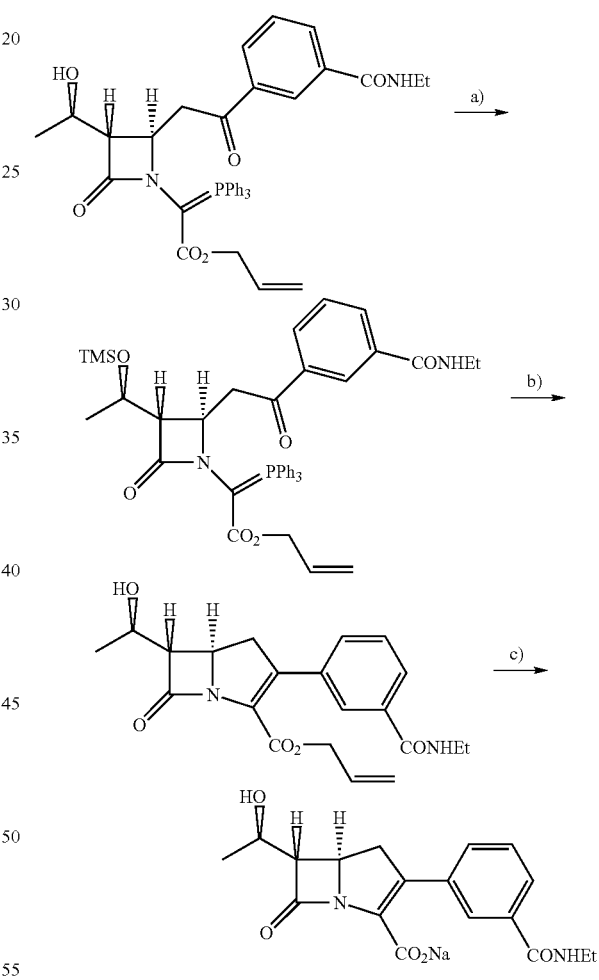

(5R,6S)-3-{3-[(Ethylamino)carbonyl]phenyl}-6-[(1R)-1-hydroxyethyl]-7-oxo-1-azabicyclo[3.2.0]hept-2-ene-2-carboxylic acid sodium salt was obtained from allyl {(2R,3S)-2-(2-{3-[(ethylamino)carbonyl]phenyl}-2-oxoethyl)-3-[(1R)-1-hydroxyethyl]-4-oxaazetidin-1-yl}(triphenylphosphoranylidene)acetate in a similar manner to Example 16.

$^1$H NMR (400 MHz, D$_2$O) δ 1.13 (t, 3H, J=7.3 Hz), 1.23 (d, 3H, J=6.4 Hz), 3.02–3.06 (m, 1H), 3.29–3.47 (m, 4H), 4.13–4.28 (m, 2H), 7.36–7.56 (m, 4H).

Example 18

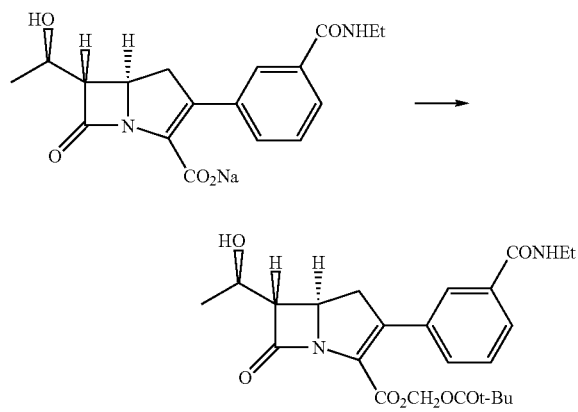

[(2,2-Dimethylpropanoyl)oxy]methyl (5R,6S)-3-{3-[(ethylamino)carbonyl]phenyl}-6-[(1R)-1-hydroxyethyl]-7-oxo-1-azabicyclo[3.2.0]hept-2-ene-2-carboxylate was obtained from (5R,6S)-3-{3-[(ethylamino)carbonyl]phenyl}-6-[(1R)-1-hydroxyethyl]-7-oxo-1-azabicyclo[3.2.0]hept-2-ene-2-carboxylic acid sodium salt in a similar manner to Example 2.

$^1$H NMR (400 MHz, CDCl$_3$) δ 1.17 (s, 9H), 1.25 (dt, 3H, J=7.2 and 2.0 Hz), 1.37 (d, 3H, J=6.3 Hz), 3.20–3.36 (m, 3H), 3.47–3.54 (m, 2H), 4.25–4.34 (m, 2H), 5.76–5.81 (m, 2H), 6.41 (br-s, 1H), 7.41–7.44 (m, 1H), 7.73–7.76 (m, 1H).

Example 19

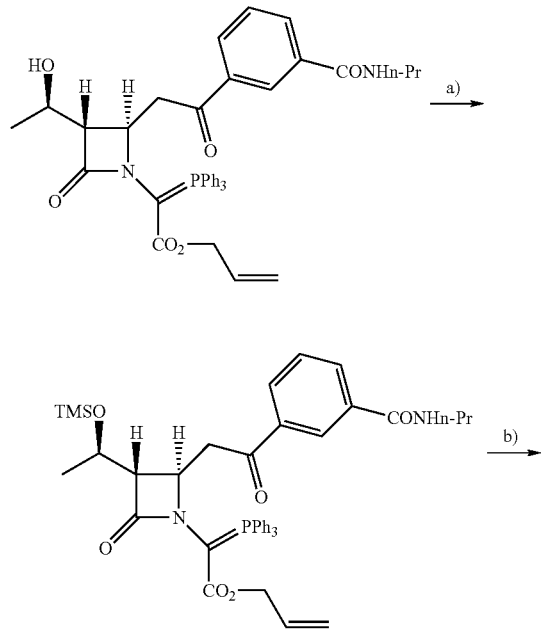

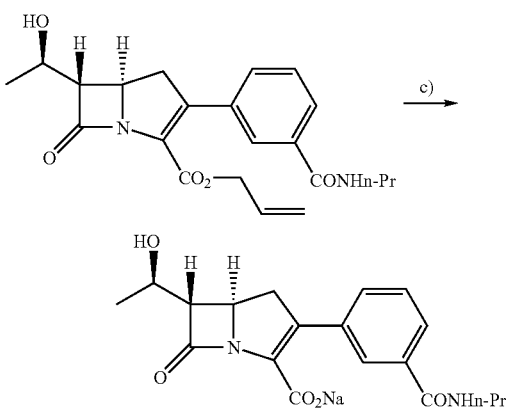

(5R,6S)-6-[(1R)-1-Hydroxyethyl]-7-oxo-3-{3-[(propylamino)carbonyl]phenyl}-1-azabicyclo[3.2.0]hept-2-ene-2-carboxylic acid sodium salt was obtained from allyl [(3S,4R)-3-[(1R)-1-hydroxyethyl]-2-oxo-4-(2-oxo-2-{3-[(propylamino)carbonyl]phenyl}ethyl)azetidin-1-yl]-(triphenylphosphoranylidene)acetate in a similar manner to Example 16.

$^1$H NMR (400 MHz, D$_2$O) δ 0.86 (t, 3H, J=7.4 Hz), 1.23 (d, 3H, J=6.4 Hz), 1.51–1.56 (m, 2H), 2.99–3.06 (m, 1H), 3.26 (t, 2H, J=7.0 Hz), 3.36–3.46 (m, 2H), 4.17–4.24 (m, 2H), 7.36–7.40 (m, 1H), 7.44–7.47 (m, 1H), 7.55–7.56 (m, 2H).

Example 20

[(2,2-Dimethylpropanoyl)oxy]methyl (5R,6S)-6-[(1R)-1-hydroxyethyl]-7-oxo-3-{3-[(propylamino)carbonyl]phenyl}-1-azabicyclo[3.2.0]-hept-2-ene-2-carboxylate was obtained from (5R,6S)-6-[(1R)-1-hydroxyethyl]-7-oxo-3-{3-[(propylamino)carbonyl]phenyl}-1-azabicyclo[3.2.0]-hept-2-ene-2-carboxylic acid sodium salt in a similar manner to Example 2.

$^1$H NMR (400 MHz, CDCl$_3$) δ 0.99 (t, 3H, J=7.4 Hz), 1.17 (s, 9H), 1.37 (d, 3H, J=6.3 Hz), 1.63–1.70 (m, 2H), 3.20–3.36 (m, 3H), 3.40–3.45 (m, 2H), 4.25–4.34 (m, 2H), 5.76–5.81 (m, 2H), 6.42 (br-s, 1H), 7.40–7.45 (m, 2H), 7.73–7.75 (m, 2H).

Example 21

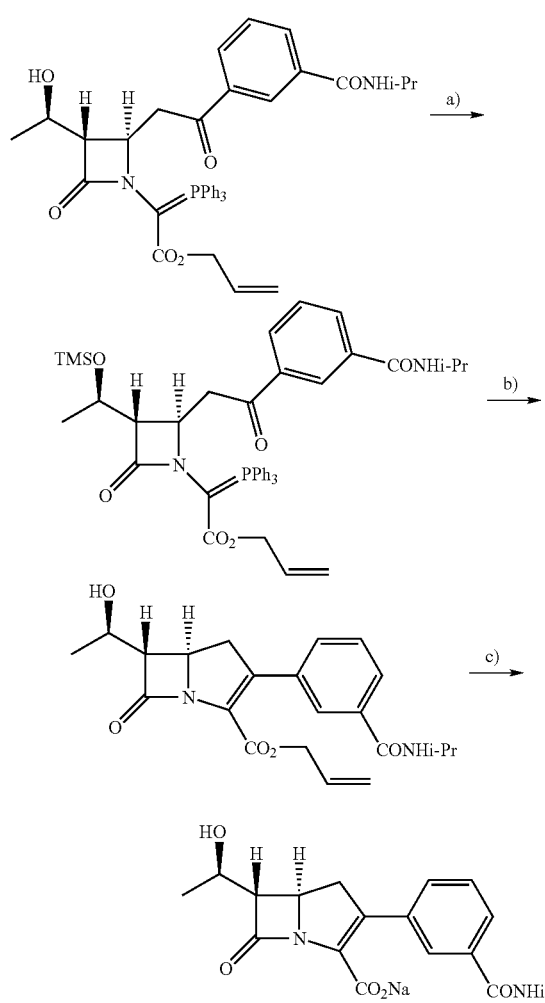

(5R,6S)-6-[(1R)-1-Hydroxyethyl]-3-{3-[(isopropylamino)carbonyl]-phenyl}-7-oxo-1-azabicyclo [3.2.0]hept-2-ene-2-carboxylic acid sodium salt was obtained from allyl [(2R,3S)-3-[(1R)-1-hydroxyethyl]-2-(2-{3-[(isopropylamino)carbonyl]phenyl}-2-oxoethyl)-4-oxoazetidin-1-yl]-(triphenylphosphoranylidene)acetate in a similar manner to Example 16.

$^1$H NMR (400 MHz, $D_2O$) δ 1.56 (d, 6H, J=6.6 Hz), 2.23 (d, 3H, J=6.4 Hz), 2.99–3.06 (m, 1H), 3.56–3.42 (m, 2H), 4.03–4.07 (m, 1H), 4.17–4.26 (m, 2H), 7.35–7.39 (m, 1H), 7.44–7.46 (m, 1H), 7.52–7.54 (m, 2H).

Example 22

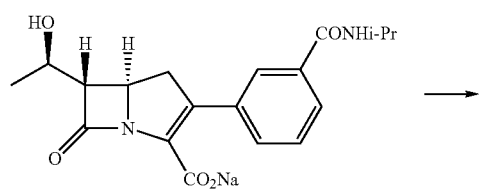

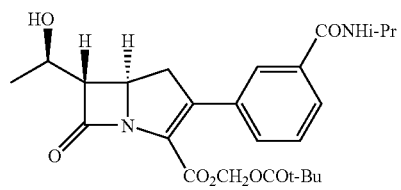

[(2,2-Dimethylpropanoyl)oxy]methyl (5R,6S)-6-[(1R)-1-hydroxyethyl]-3-{3-[(isopropylamino)carbonyl]phenyl}-7-oxo-1-azabicyclo[3.2.0]-hept-2-ene-2-carboxylate was obtained from (5R,6S)-6-[(1R)-1-hydroxyethyl]-3-{3-[(isopropylamino)carbonyl]phenyl}-7-oxo-1-azabicyclo[3.2.0]-hept-2-ene-2-carboxylic acid sodium salt in a similar manner to Example 2.

$^1$H NMR (400 MHz, $CDCl_3$) δ 1.16 (s, 9H), 1.27 (d, 6H, J=6.6 Hz), 1.37 (d, 3H, J=6.3 Hz), 2.96–3.36 (m, 3H), 4.24–4.34 (m, 3H), 5.75 (d, 1H, J=5.5 Hz), 5.82 (d, 1H, J=5.5 Hz), 6.13 (br-d, 1H, J=8.0 Hz), 7.41–7.45 (m, 2H), 7.69–7.73 (m, 2H).

Example 23

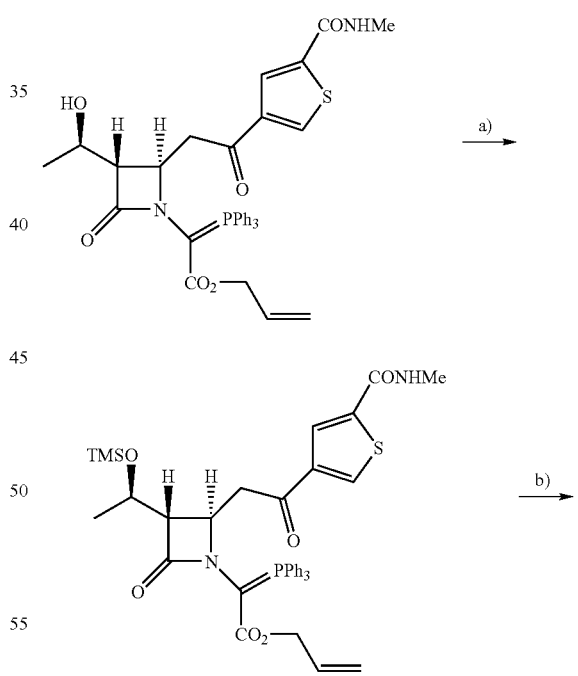

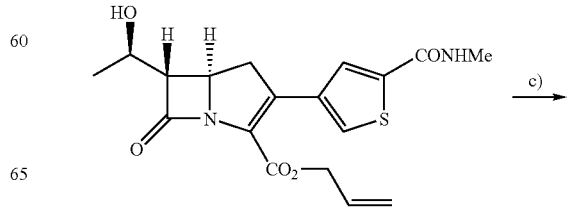

-continued

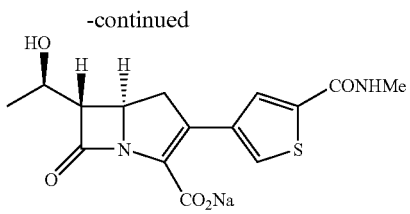

(5R,6S)-6-[(1R)-1-Hydroxyethyl]-3-{5-[(methylamino)carbonyl]-thien-3-yl}-7-oxo-1-azabicyclo[3.2.0]hept-2-ene-2-carboxylic acid sodium salt was obtained from allyl [(2R,3S)-3-[(1R)-1-hydroxyethyl]-2-(2-{5-[(methylamino)carbonyl]thien-3-yl}-2-oxoethyl)-4-oxoazetidin-1-yl]-(triphenylphosphoranylidene)acetate in a similar manner to Example 16.

$^1$H NMR (400 MHz, $D_2O$) δ 1.22 (d, 3H, J=6.4 Hz), 2.81 (s, 3H), 3.04–3.11 (m, 1H), 3.24–3.41 (m, 1H), 3.39–3.41 (m, 1H), 4.15–4.18 (m, 2H), 7.54 (d, 1H, J=1.4 Hz), 7.70 (d, 1H, J=1.4 Hz).

Example 24

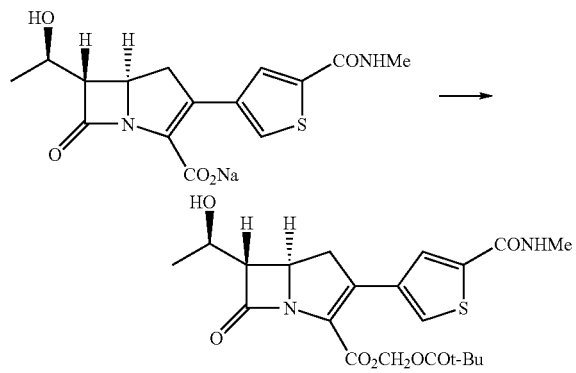

[(2,2-Dimethylpropanoyl)oxy]methyl (5R,6S)-6-[(1R)-1-hydroxyethyl]-3-{5-[(methylamino)carbonyl]thien-3-yl}-7-oxo-1-azabicyclo[3.2.0]-hept-2-ene-2-carboxylate was obtained from (5R,6S)-6-[(1R)-1-hydroxyethyl]-3-{5-[(methylamino)carbonyl]thien-3-yl}-7-oxo-1-azabicyclo-[3.2.0]hept-2-ene-2-carboxylic acid sodium salt in a similar manner to Example 2.

$^1$H NMR (400 MHz, $CDCl_3$) δ 1.23 (s, 9H), 1.36 (d, 3H, J=6.3 Hz), 3.01 (d, 3H, J=4.8 Hz), 3.22–3.24 (m, 1H), 3.34. (d, 2H, J=9.4 Hz), 4.22–4.30 (m, 2H), 5.88–5.92 (m, 2H), 6.91 (br-d, 1H, J=4.5 Hz), 7.65 (d, 1H, J=1.3 Hz), 7.87 (d, 1H, J=1.3 Hz).

Example 25

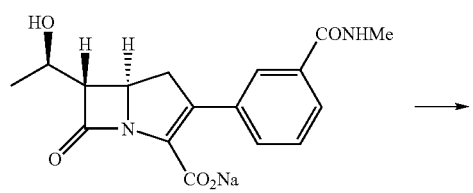

-continued

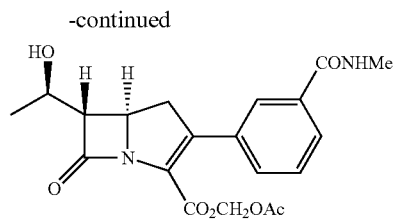

(Acetyloxy)methyl (5R,6S)-6-[(1R)-1-hydroxyethyl]-3-{3-[(methylamino)carbonyl]phenyl}-7-oxo-1-azabicyclo[3.2.0]hept-2-ene-2-carboxylate was obtained from (5R,6S)-6-[(1R)-1-hydroxyethyl]-3-{3-[(methylamino)carbonyl]phenyl}-7-oxo-1-azabicyclo[3.2.0]hept-2-ene-2-carboxylic acid sodium salt in a similar manner to Example 2.

$^1$NMR (400 MHz, $CDCl_3$) δ 1.35 (d, 3H, J=6.3 Hz), 2.08 (s, 3H), 2.30 (br-s, 1H), 3.00 (d, 3H, J=4.8 Hz), 3.20–3.35 (m, 3H), 4.21–4.33 (m, 2H), 5.77 (s, 2H), 6.49 (br-d, 1H, J=4.3 Hz), 7.40–7.48 (m, 2H), 7.73–7.76 (m, 2H).

Example 26

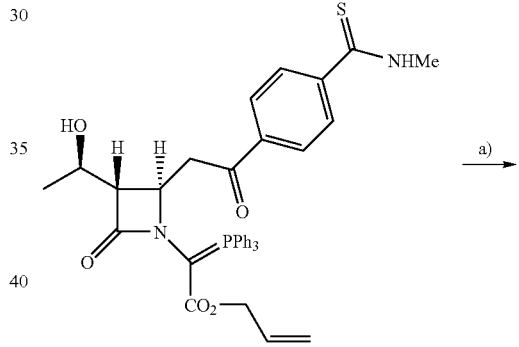

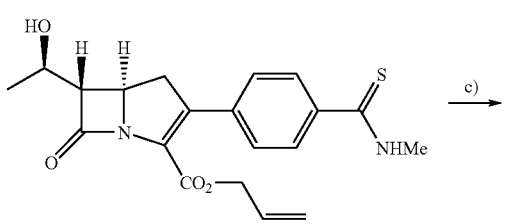

-continued

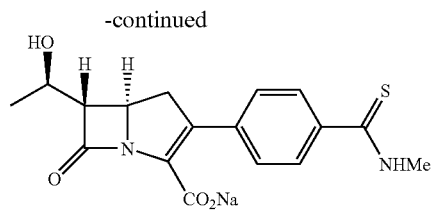

(5R,6S)-3-[4-(Methylaminothiocarbonyl)phenyl]-6-[(1R)-1-hydroxyethyl]-7-oxo-1-azabicyclo[3.2.0]hept-2-ene-2-carboxylic acid sodium salt was obtained from allyl {(2R,3S)-2-{2-[4-(methylaminothiocarbonyl)phenyl]-2-oxoethyl}-3-[(1R)-1-hydroxyethyl]-4-oxo-1-azetidinyl}-(triphenylphosphoranylidene)acetate in a similar manner to Example 12.

Example 27

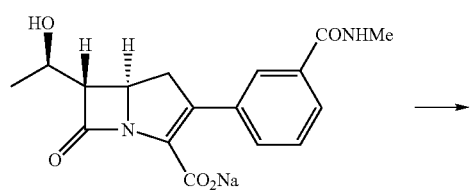

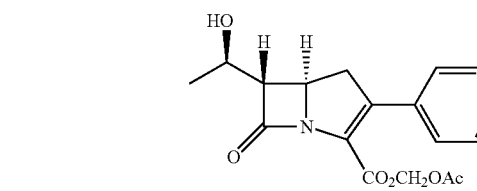

[(2,2-Dimethylpropanoyl)oxy]methyl (5R,6S)-3-[4-(methylaminothiocarbonyl)phenyl]-6-[(1R)-1-hydroxyethyl]-7-oxo-1-azabicyclo[3.2.0]-hept-2-ene-2-carboxylate was obtained from (5R,6S)-3-[4-(methylaminothiocarbonyl)phenyl]-6-[(1R)-1-hydroxyethyl]-7-oxo-1-azabicyclo[3.2.0]-hept-2-ene-2-carboxylic acid sodium salt in a similar manner to Example 2.

Example 28

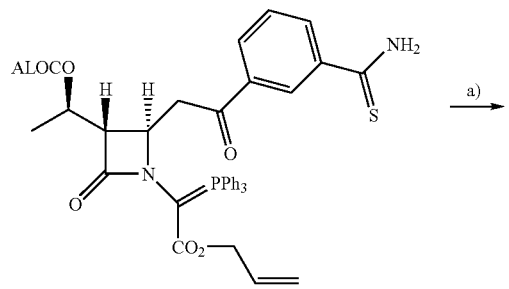

-continued

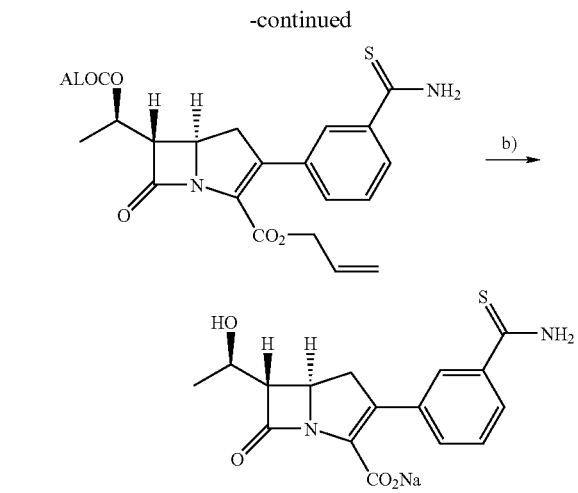

(5R,6S)-3-[3-(Aminothiocarbonyl)phenyl]-6-[(1R)-1-hydroxyethyl]-7-oxo-1-azabicyclo[3.2.0]hept-2-ene-2-carboxylic acid sodium salt was obtained from allyl ((2R,3S)-3-((1R)-1-{[(allyloxy)carbonyl]oxy}ethyl)-2-{2-[3-(aminothiocarbonyl)phenyl]-2-oxoethyl}-4-oxo-1-azetidinyl) (triphenylphosphoranylidene)acetate in a similar manner to Example 3.

Example 29

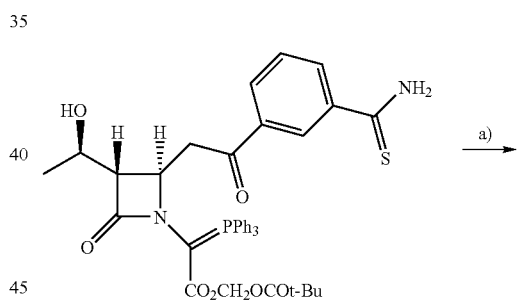

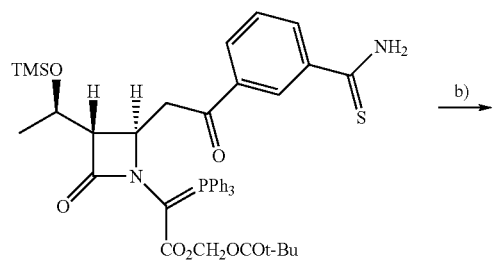

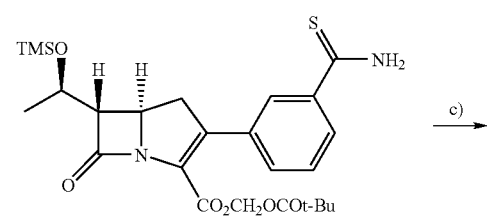

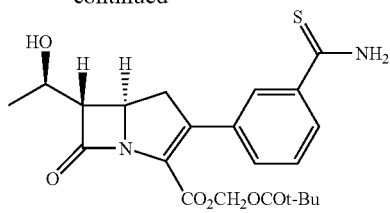

[(2,2-Dimethylpropanoyl)oxy]methyl (5R,6S)-3-[3-(aminothiocarbonyl)phenyl]-6-[(1R)-1-hydroxyethyl]-7-oxo-1-azabicyclo[3.2.0]hept-2-ene-2-carboxylate was obtained from {[2-{(2R,3S)-2-{2-[3-(aminothiocarbonyl)phenyl]-2-oxoethyl}-3-[(1R)-1-hydroxyethyl]-4-oxo-1-azetidinyl}-2-(triphenylphosphoranylidene)acetyl]oxy}methyl pivalate in a similar manner to Example 5.

Example 30

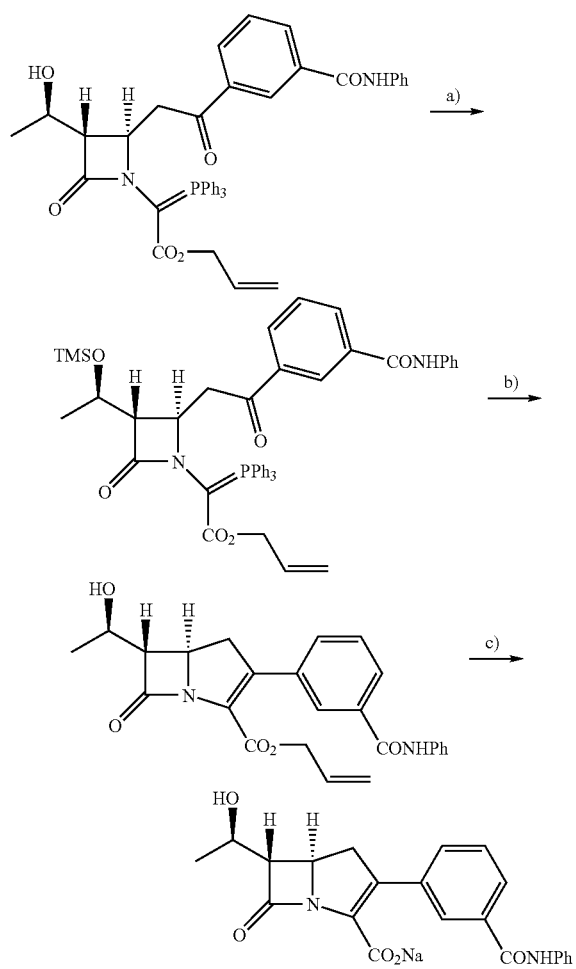

(5R,6S)-3-[3-(Anilinocarbonyl)phenyl]-6-[(1R)-1-hydroxyethyl]-7-oxo-1-azabicyclo[3.2.0]hept-2-ene-2-carboxylic acid sodium salt was obtained from allyl {(2R,3S)-2-{2-[3-(anilinocarbonyl)phenyl]-2-oxoethyl}-3-[(1R)-1-hydroxyethyl]-4-oxoazetidine-1-yl}(triphenylphosphoranylidene)acetate in a similar manner to Example 16.

$^1$H NMR (400 MHz, D$_2$O) δ 1.22 (d, 3H, J=6.4 Hz), 2.98–3.05 (m, 1H), 3.35–3.45 (m, 2H), 4.16–4.25 (m, 2H), 7.20–7.24 (m, 1H), 7.37–7.51 (m, 6H), 7.66–7.68 (m, 2H).

Example 31

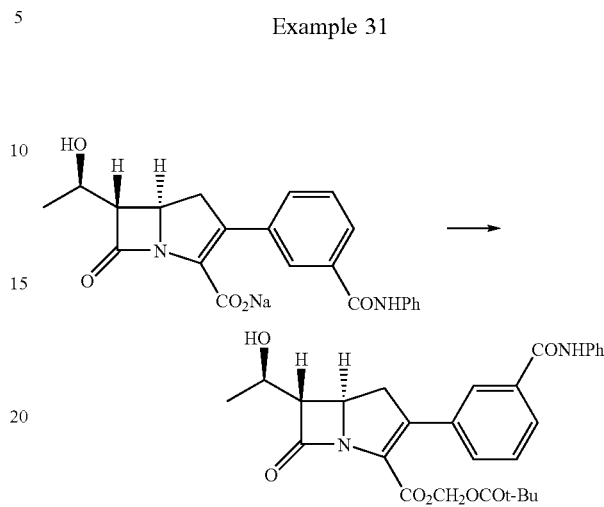

[(2,2-Dimethylpropanoyl)oxy]methyl (5R,6S)-3-[3-(anilinocarbonyl)phenyl]-6-[(1R)-1-hydroxyethyl]-7-oxo-1-azabicyclo[3.2.0]-hept-2-ene-2-carboxylate was obtained from (5R,6S)-3-[3-(anilinocarbonyl)phenyl]-6-[(1R)-1-hydroxyethyl]-7-oxo-1-azabicyclo[3.2.0]hept-2-ene-2-carboxylic acid sodium salt in a similar manner to Example 2.

$^1$H NMR (400 MHz, CDCl$_3$) δ 1.12 (s, 9H), 1.36 (d, 3H, J=6.3 Hz), 3.20–3.37 (m, 3H), 4.25–4.35 (m, 2H), 5.78 (d, 1H, J=5.5 Hz), 5.84 (d, 1H, J=5.5 Hz), 7.16 (t, 1H, J=7.4 Hz), 7.35–7.39 (m, 2H), 7.44–7.68 (m, 4H), 7.83–7.85 (m, 2H), 8.25 (br-s, 1H).

Example 32

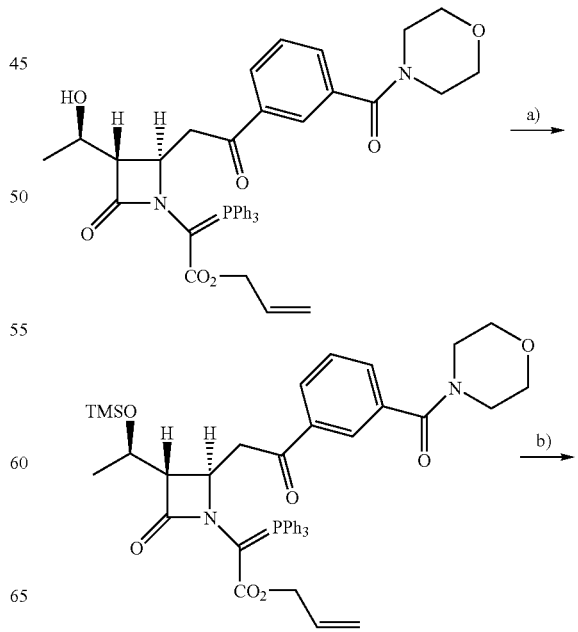

-continued

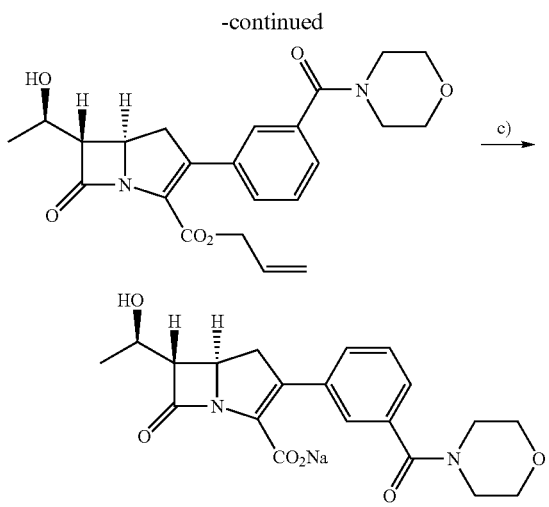

(5R,6S)-6-[(1R)-1-Hydroxyethyl]-3-[3-(morpholin-4-yl-carbonyl)-phenyl]-7-oxo-1-azabicyclo[3.2.0]hept-2-ene-2-carboxylic acid sodium salt was obtained from allyl ((2R,3S)-3-[(1R)-1-hydroxyethyl]-2-{2-[3-(morpholin-4-ylcarbonyl)phenyl]-2-oxoethyl}-4-oxoazetidin-1-yl)(triphenylphosphoranylidene)acetate in a similar manner to Example 16.

$^1$H NMR (400 MHz, D$_2$O) δ 1.22 (d, 3H, J=6.4 Hz), 2.98–3.05 (m, 1H), 3.34–3.45 (m, 4H), 3.61–3.76 (m, 6H), 4.16–4.26 (m, 2H), 7.25–7.28 (m, 2H), 7.38–7.39 (m, 2H).

Example 33

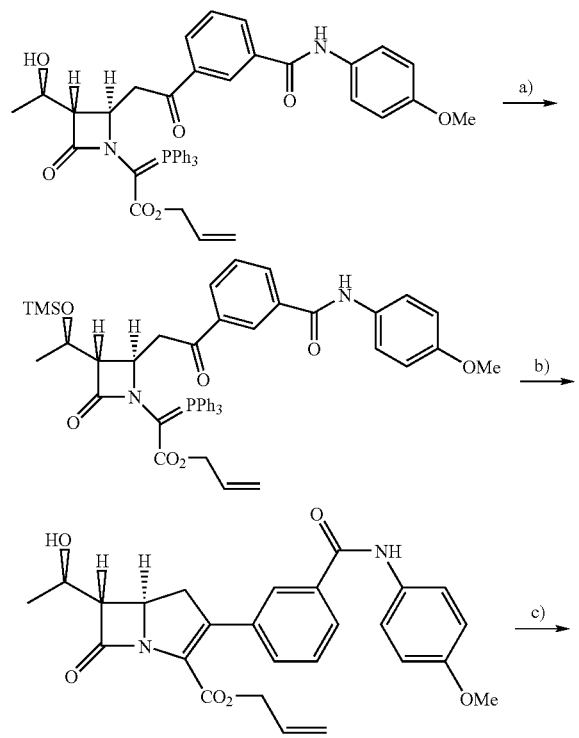

-continued

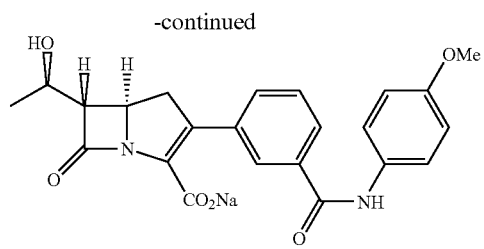

(5R,6S)-6-[(1R)-1-Hydroxyethyl]-3-(3-{[(4-methoxyphenyl)amino]-carbonyl}phenyl)-7-oxo-1-azabicyclo[3.2.0]hept-2-ene-2-carboxylic acid sodium salt was obtained from allyl {(2R,3S)-3-[(1R)-1-hydroxyethyl]-2-[2-(3-{[(4-methoxyphenyl)amino]carbonyl}phenyl)-2-oxoethyl]-4-oxoazetidin-1-yl}(triphenylphosphoranylidene)acetate in a similar manner to Example 16.

$^1$H NMR (400 MHz, D$_2$O) δ 1.21 (d, 3H, J=6.4 Hz), 2.95–3.01 (m, 1H), 3.31–3.41 (m, 2H), 3.74 (s, 3H), 4.14–4.22 (m, 2H), 6.43 (d, 2H, J=8.9 Hz), 7.33 (d, 2H, J=8.9 Hz), 7.37–7.48 (m, 2H), 7.61–7.63 (m, 2H).

Example 34

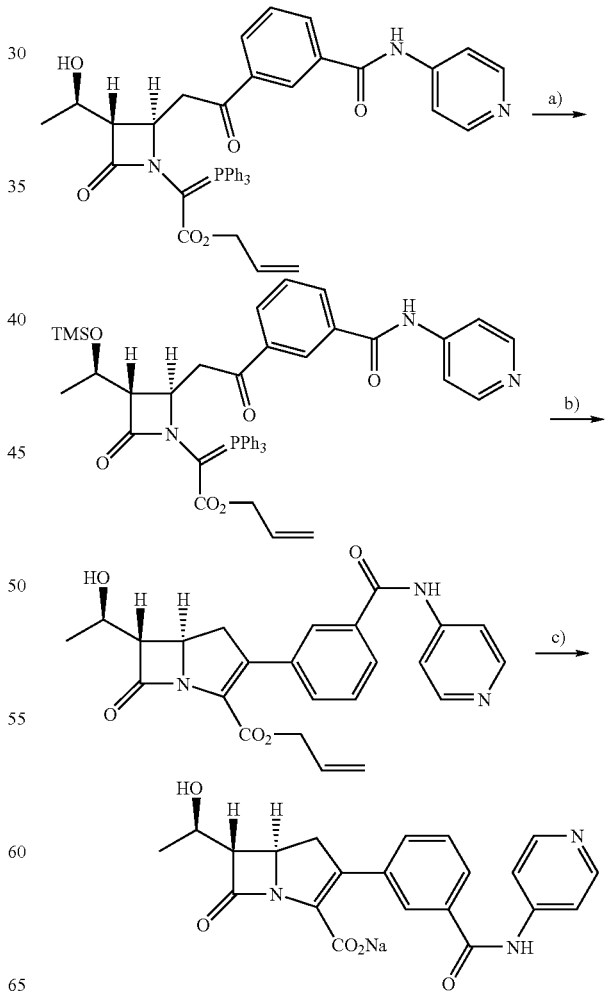

(5R,6S)-6-[(1R)-1-Hydroxyethyl]-7-oxo-3-{3-[(pyridin-4-ylamino)carbonyl]phenyl}-1-azabicyclo[3.2.0]hept-2-ene-2-carboxylic acid sodium salt was obtained from allyl [(3S,4R)-3-[(1R)-1-hydroxyethyl]-2-oxo-4-(2-oxo-2-{3-[(pyridin-4-ylamino)carbonyl]phenyl}ethyl)azetidin-1-yl](triphenylphosphoranylidene)acetate in a similar manner to Example 16.

$^1$H NMR (400 MHz, D$_2$O) δ 1.21 (d, 3H, J=6.4 Hz), 2.96–3.03 (m, 1H), 3.33–3.39 (m, 1H), 3.42–3.44 (m, 1H), 4.13–4.24 (m, 2H), 7.38–7.42 (m, 1H), 7.47–7.50 (m, 1H), 7.57 (dd, 2H, J=5.0, 1.6 Hz), 7.64–7.66 (m, 2H), 8.37 (dd, 2H, J=5.0, 1.6 Hz).

Example 35

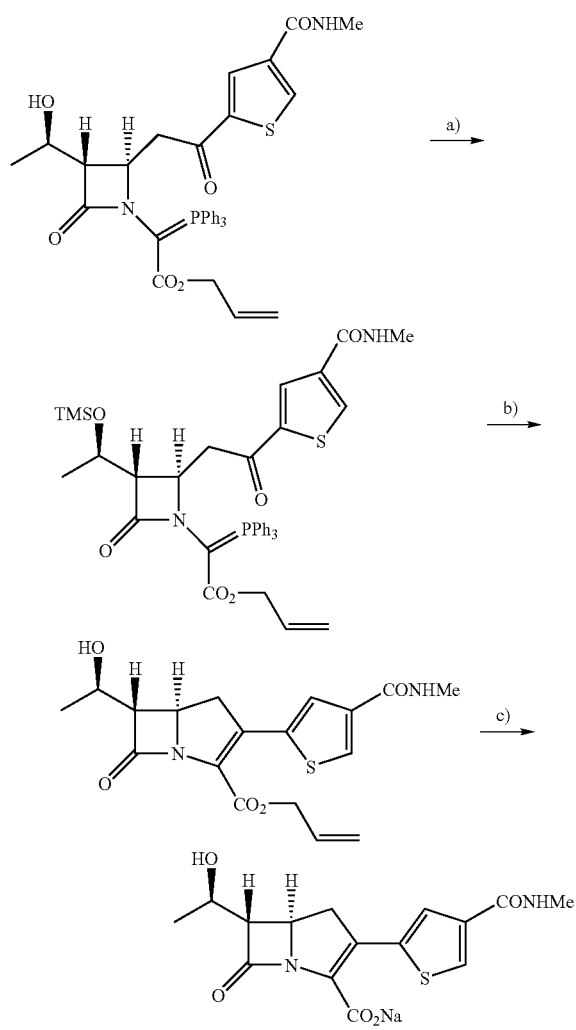

(5R,6S)-6-[(1R)-1-Hydroxyethyl]-3-{4-[(methylamino)carbonyl]-thien-2-yl}-7-oxo-1-azabicyclo[3.2.0]hept-2-ene-2-carboxylic acid sodium salt was obtained from allyl [(2R,3S)-3-[(1R)-1-hydroxyethyl]-2-(2-{4-[(methylamino)carbonyl]thien-2-yl}-2-oxoethyl)-4-oxoazetidin-1-yl](triphenylphosphoranylidene)acetate in a similar manner to Example 16.

$^1$H NMR (400 MHz, D$_2$O) δ 1.22 (d, 3H, J=6.4 Hz), 2.79 (s, 3H), 3.16–3.30 (m, 2H), 3.38–3.40 (m, 1H), 4.13–4.19 (m, 2H), 7.33 (d, 1H, J=1.5 Hz), 7.86 (d, 1H, J=1.5 Hz).

Example 36

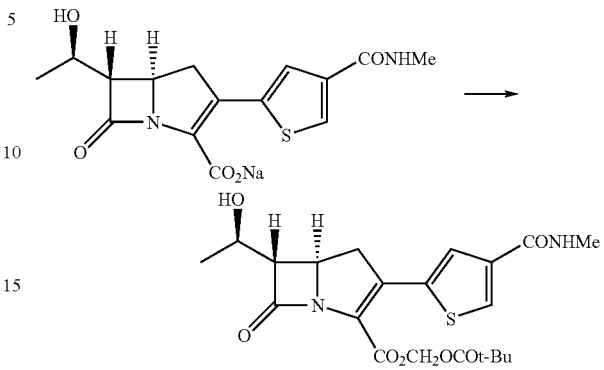

[(2,2-Dimethylpropanoyl)oxy]methyl (5R,6S)-6-[(1R)-1-hydroxyethyl]-3-{4-[(methylamino)carbonyl]thien-2-yl}-7-oxo-1-azabicyclo[3.2.0]-hept-2-ene-2-carboxylate was obtained from (5R,6S)-6-[(1R)-1-hydroxyethyl]-3-{4-[(methylamino)carbonyl]thien-2-yl}-7-oxo-1-azabicyclo[3.2.0]-hept-2-ene-2-carboxylic acid sodium salt in a similar manner to Example 2.

$^1$H NMR (400 MHz, CDCl$_3$) δ 1.23 (s, 9H), 1.36 (d, 3H, J=6.3 Hz), 2.99 (d, 3H, J=4.8 Hz), 3.22–3.24 (m, 1H), 3.33–3.50 (m, 2H), 4.23–4.28 (m, 2H), 5.91 (d, 1H, J=5.6 Hz), 5.98 (d, 1H, J=5.6 Hz), 6.51–6.52 (m, 1H), 7.87 (d, 1H, J=1.3 Hz), 8.01 (d, 1H, J=1.3 Hz).

Example 37

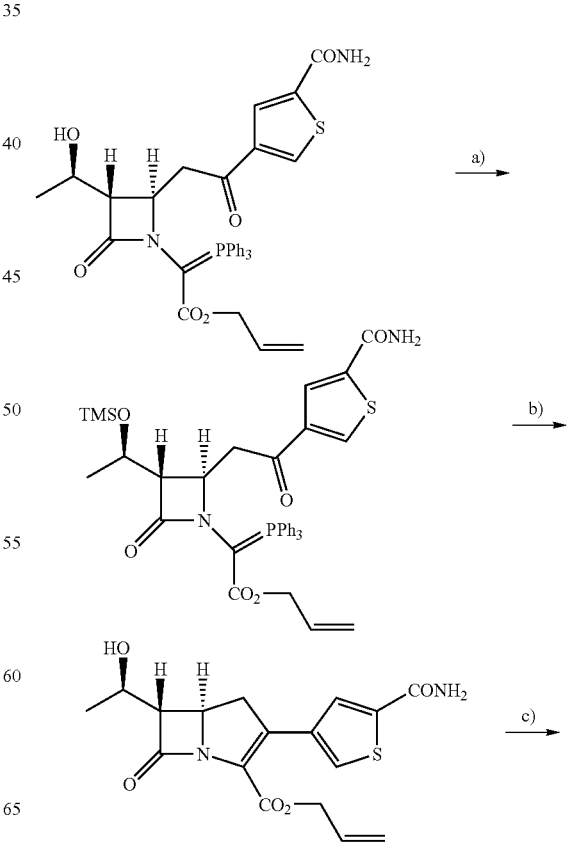

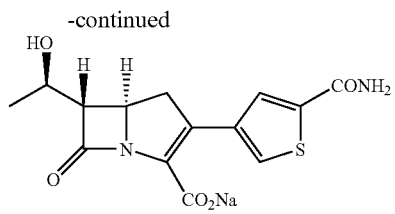

(5R,6S)-3-[5-(Aminocarbonyl) thien-3-yl]-6-[(1R)-1-hydroxyethyl]-7-oxo-1-azabicyclo[3.2.0]hept-2-ene-2-carboxylic acid sodium salt was obtained from allyl {(2R,3S)-2-{2-[5-(aminocarbonyl)thien-3-yl]-2-oxoethyl}-3-[(1R)-1-hydroxyethyl]-4-oxoazetidin-1-yl}(triphenylphosphoranylidene)acetate in a similar manner to Example 16.

$^1$H NMR (400 MHz, D$_2$O) δ 1.21 (d, 3H, J=6.4 Hz), 3.03–3.10 (m, 1H), 3.22–3.29 (m, 1H), 3.38–3.40 (m, 1H), 4.13–4.20 (m, 2H), 7.58 (d, 1H, J=1.4 Hz), 7.77 (d, 1H, J=1.4 Hz).

Example 38

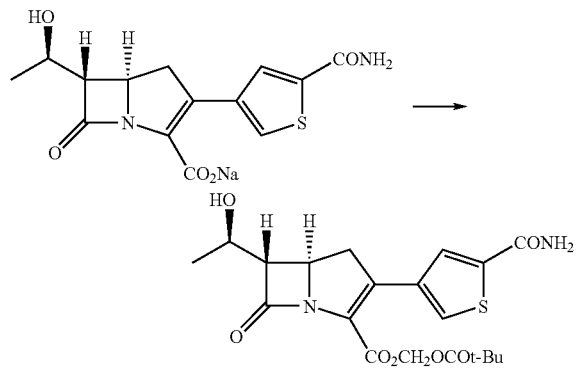

[(2,2-Dimethylpropanoyl)oxy]methyl (5R,6S)-3-[5-(aminocarbonyl)thien-3-yl]-6-[(1R)-1-hydroxyethyl]-7-oxo-1-azabicyclo[3.2.0]hept-2-ene-2-carboxylate was obtained from (5R,6S)-3-[5-(aminocarbonyl)thien-3-yl]-6-[(1R)-1-hydroxyethyl]-7-oxo-1-azabicyclo[3.2.0]hept-2-ene-2-carboxylic acid sodium salt in a similar manner to Example 2.

$^1$H NMR (400 MHz, CDCl$_3$) δ 1.22 (s, 9H), 1.37 (d, 3H, J=6.3 Hz), 1.96 (br-d, 1H, J=4.3 Hz), 3.22–3.25 (m, 1H), 3.34 (d, 2H, J=9.4 Hz), 4.23–4.29 (m, 2H), 5.88 (d, 1H, J=5.6 Hz), 5.91 (d, 1H, J=5.6 Hz), 7.72 (d, 1H, J=1.3 Hz), 7.95 (d, 1H, J=1.3 Hz).

Example 39

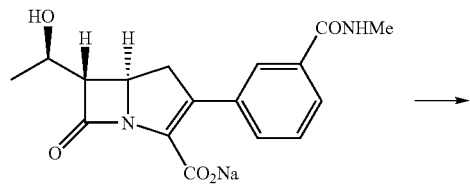

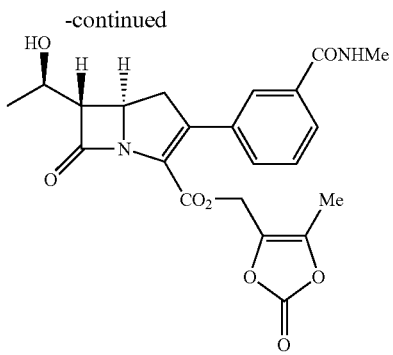

(5-Methyl-2-oxo-1,3-dioxol-4-yl)methyl (5R,6S)-6-[(1R)-1-hydroxyethyl]-3-{3-[(methylamino)carbonyl]phenyl}-7-oxo-1-azabicyclo [3.2.0]-hept-2-ene-2-carboxylate (42 mg) was obtained from (5R,6S)-6-[(1R)-1-hydroxyethyl]-3-{3-[(methyl amino)carbonyl]phenyl}-7-oxo-1-azabicyclo[3.2.0]hept-2-ene-2-carboxylic acid sodium salt (72 mg) in a similar manner to Example 2.

$^1$H NMR (400 MHz, CDCl$_3$) δ 1.38 (3H, d, J=6.3 Hz), 2.13 (3H, s), 3.02 and 3.04 (combined 3H, each s), 3.20–3.40 (3H, m), 4.22–4.38 (2H, m), 4.76–4.94 (2H, m), 6.30 (1H, broad s), 7.35–7.47 (2H, m), 7.63–7.70 (1H, m), 7.75–7.79 (1H, m).

Example 40

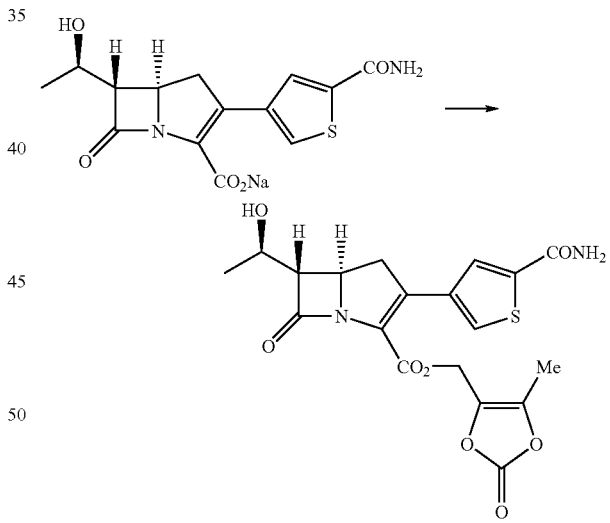

(5-Methyl-2-oxo-1,3-dioxol-4-yl)methyl (5R,6S)-3-[5-(aminocarbonyl)thien-3-yl]-6-[(1R)-1-hydroxyethyl]-7-oxo-1-azabicyclo[3.2.0]-hept-2-ene-2-carboxylate (58.5 mg) was obtained from (5R,6S)-3-[5-(aminocarbonyl)thien-3-yl]-6-[(1R)-1-hydroxyethyl]-7-oxo-1-azabicyclo-[3.2.0]hept-2-ene-2-carboxylic acid sodium salt (102 mg) in a similar manner to Example 2.

$^1$H NMR (400 MHz, CD$_3$OD) δ 1.30 (3H, d, J=6.3 Hz), 2.19 (3H, s), 3.35–3.43 (2H, m), 4.08–4.17 (1H, m), 4.21–4.29. (1H, m), 5.02–5.12 (2H, m), 7.99. (1H, d, J=1.4 Hz), 8.12, (1H, d, J=1.4 Hz).

Reference Example 1

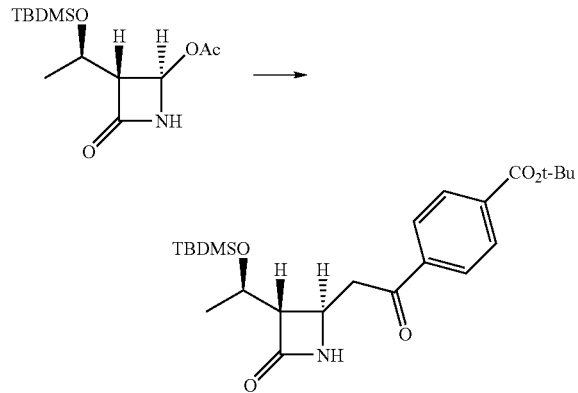

To a solution of (2R,3R)-3-((11R)-1-{[tert-butyl(dimethyl) silyl]oxy}-ethyl)-4-oxo-2-azetidinyl acetate (14.37 g) and tert-butyl 4-{[(trimethylsilyl)oxy]vinyl}benzoate (about 50 mmol) in dry methylene chloride (90 ml) was added zinc iodide (15.96 g, 50 mmol) at room temperature, and the mixture was reacted overnight at the same temperature. The reaction solution was diluted with chloroform and an aqueous sodium hydrogen carbonate solution, and extracted and separated. The organic layer was washed successively with an aqueous sodium thiosulfate solution, a saturated brine, and dried over anhydrous magnesium sulfate. The solvent was evaporated under reduced pressure, and the residue was purified by silica gel column chromatography (chloroform/ethyl acetate) to give tert-butyl 4-{[(2R,3S)-3-((1R)-1-{[tert-butyl(dimethyl)silyl]oxy}ethyl)-4-oxo-2-azetidinyl]acetyl}benzoate, (5.32 g).

$^1$H NMR (400 MHz, CDCl$_3$) δ 0.08 (3H, s), 0.09 (3H, s), 0.88 (9H, s), 1.26 (3H, d, J=6.2 Hz), 1.62 (9H, s), 2.90 (1H, dd, J=2.3 Hz and 5.3 Hz), 3.13–3.25 (1H, m), 3.43–3.53 (1H, m), 4.08–4.18 (1H, m), 4.18–4.28 (1H, m), 6.13 (1H, s), 7.97 (2H, d, J=8.2 Hz), 8.09. (2H, d, J=8.3 Hz).

Reference Example 2

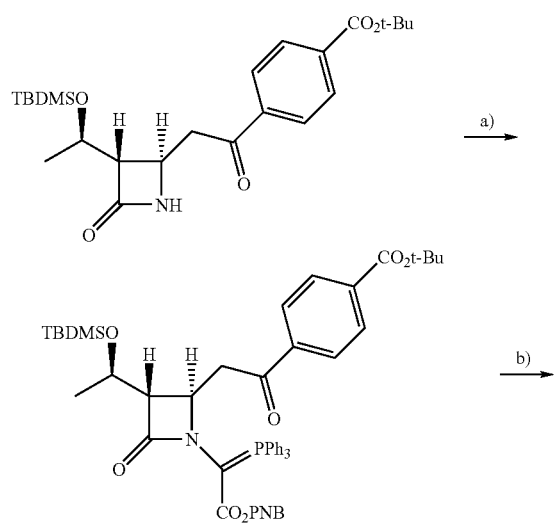

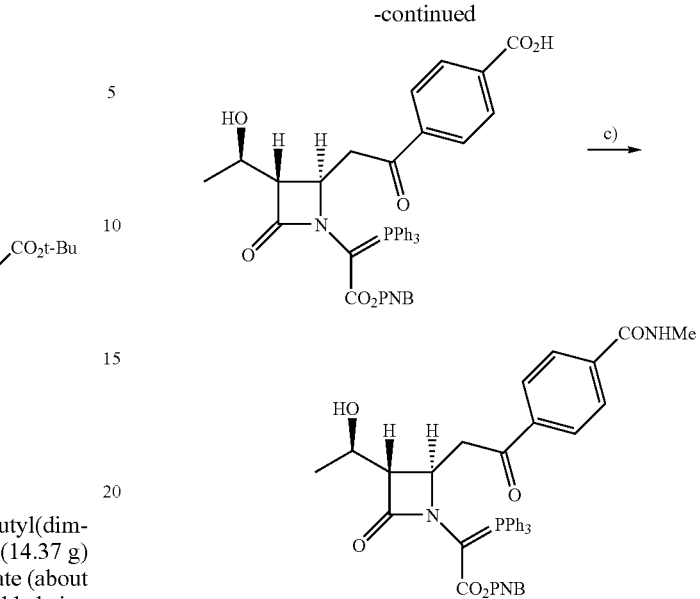

Step a)

p-Nitrobenzyl glyoxylate monohydrate (1.477 g) was dissolved in toluene (50 ml), and the mixture was subjected to azeotropic dehydration under heating with reflux. The resultant was cooled to room temperature once, and then thereto was added tert-butyl 4-{[(2R,3S)-3-((1R)-1-{[tert-butyl(dimethyl) silyl]oxy}ethyl)-4-oxo-2-azetidinyl]acetyl}benzoate (2.238 g), and dissolved it, and the mixture was subjected to azeotropic dehydration under stirring with reflux. After the starting materials were consumed, the solvent was evaporated under reduced pressure. The residue was dissolved in dry THF (20 ml), and thereto, was added 2,6-lutidine (809 mg), and the mixture was cooled to −20 to −30° C. To the mixture was added dropwise thionyl chloride (898 mg) at the same temperature. The insoluble materials were separated by filtration, and washed with dry THF. The filtrate was concentrated under reduced pressure at a temperature below. 35° C. The residue was dissolved in dry 1,4-dioxane (100 ml), and thereto were added triphenylphosphine (2.83 g) and 2,6-lutidine (1.179 g). The mixture was stirred at room temperature for one hour, and further stirred with heating at a bath temperature of 60° C. for 3.5 hours. The mixture was cooled to room temperature, and thereto were added ethyl acetate and cold aqueous citric acid solution, and the mixture was extracted and separated. The organic layer was washed successively with cold aqueous citric acid solution (twice), a saturated brine, an aqueous sodium hydrogen carbonate solution, and a saturated brine, dried over anhydrous magnesium sulfate, and the solvent was evaporated under reduced pressure. The residue was purified by silica gel column chromatography (hexane/ethyl acetate) to give tert-butyl 4-({(2R,3S)-3-((1R)-1-{[tert-butyl (dimethyl) silyl]oxy}ethyl)-1-[2-[(4-nitrobenzyl)oxy]-2-oxo-1-(triphenylphosphoranylidene)ethyl]-4-oxo-2-azetidinyl}acetyl)benzoate (2.870 g).

IR (KBr) 1746, 1716, 1688, 1625, 1522, 835, 774, 751, 719 cm$^{-1}$

Step b)

To tert-butyl 4-({(2R,3S)-3-((1R)-1-{[tert-butyl(dimethyl)silyl]oxy}-ethyl)-1-[2-[(4-nitrobenzyl)oxy]-2-oxo-1-(triphenylphosphoranylidene)ethyl]-4-oxo-2-azetidinyl}acetyl)benzoate (2.703 g, 3.00 mmol) obtained in Step a) was added trifluoroacetic acid (9 ml) under ice-cooling and dissolved it, and the mixture was further stirred at room temperature for 30 minutes. The solvent was evaporated under reduced pressure, and the residue was dissolved again in chloroform/toluene, and concentrated again under reduced pressure. To the residue was added hexane/diethyl ether, and the mixture was subjected to decantation (three times), and the resulting solid was collected by filtration, washed with hexane, and dried under reduced pressure to give 4-({(2R,3S)-3-[(1R)-1-hydroxyethyl]-1-[2-[(4-nitrobenzyl)oxy]-2-oxo-1-(triphenylphosphoranylidene)ethyl]-4-oxo-2-azetidinyl}acetyl)benzoic acid (2.187 g).

IR (KBr) 3428 (broad), 1719, 1680, 1523, 750, 721 cm$^{-1}$

Step c)

4-({(2R,3S)-3-[(1R)-1-Hydroxyethyl]-1-[2-[(4-nitrobenzyl)oxy]-2-oxo-1-(triphenylphosphoranylidene)ethyl]-4-oxo-2-azetidinyl}acetyl)benzoic acid (2.137 g) obtained in Step b) was dissolved in dry THF (24 ml), and thereto was added dropwise a solution of triethylamine (354 mg) in dry THF (3 ml) at −30° C. Subsequently, to the mixture was added dropwise a solution of ethyl chloroformate (348 mg) in dry THF (3 ml). In addition, to the mixture was added dropwise a solution of triethylamine (354 mg) in THF (3 ml), and further thereto was added dropwise a solution of monomethylamine in 40% methanol (249 mg). The mixture was warmed to about 0° C., and to the reaction solution were added ethyl acetate and ice-water. The mixture was extracted and separated, and the organic layer was washed successively with an aqueous sodium hydrogen carbonate solution, brine, diluted hydrochloric acid and an aqueous sodium hydrogen carbonate solution, dried over anhydrous magnesium sulfate, and the solvent was removed under reduced pressure to give 4-nitrobenzyl [(2R,3S)-3-[(1R)-1-hydroxyethyl]-2-(2-{4-[(methylamino)carbonyl]phenyl}-2-oxoethyl)-4-oxo-1-azetidinyl](triphenylphosphoranylidene)acetate (1.909 g).

IR (KBr) 3388 (broad), 1742, 1649, 1607, 1521, 753, 720 cm$^{-1}$

Reference Example 3

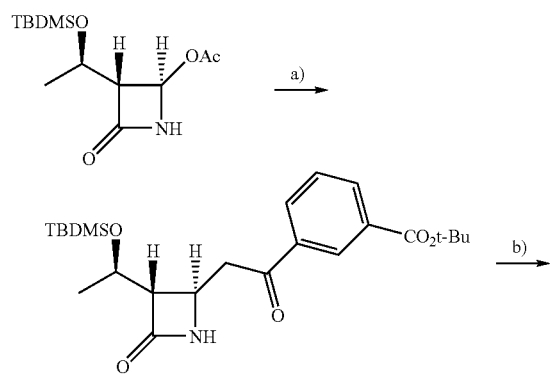

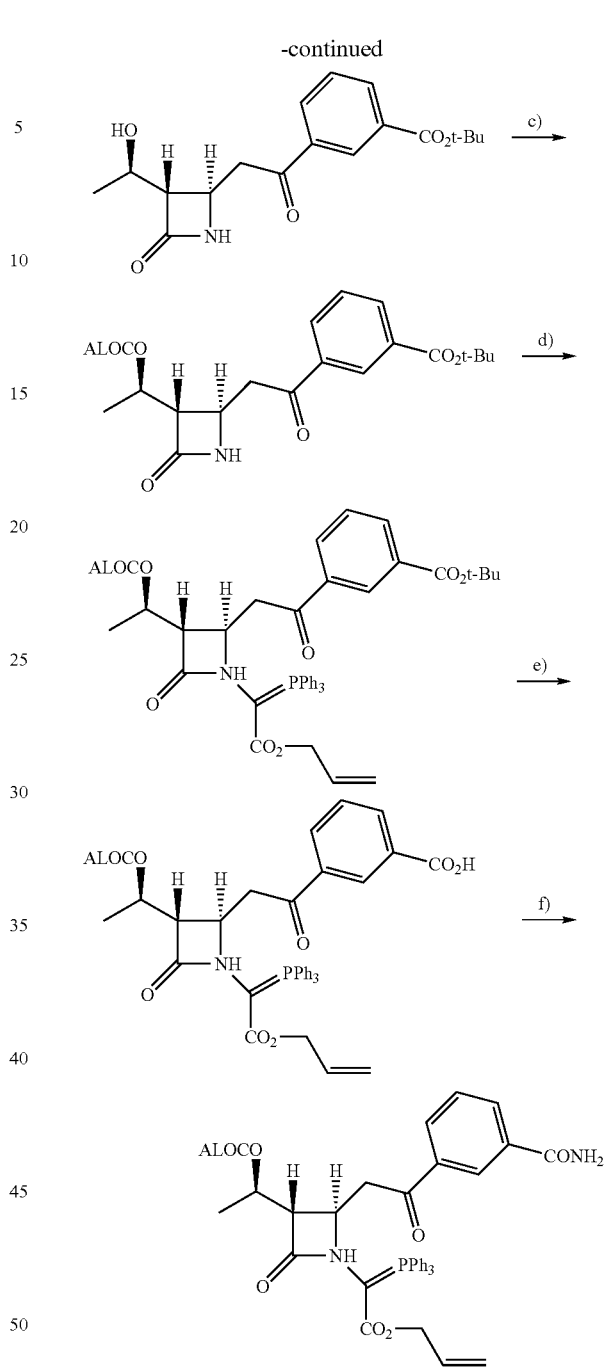

Step a)

tert-Butyl 3-{[(2R,3S)-3-((1R)-1-{[tert-butyl(dimethyl)silyl]oxy}-ethyl)-4-oxo-2-azetidinyl]acetyl}benzoate (7.831 g) was obtained from (2R,3R)-3-((1R)-1-{[tert-butyl(dimethyl)silyl]oxy}ethyl)-4-oxo-2-azetidinyl acetate (11.78 g) in a similar manner to Reference Example 1.

$^1$H NMR (400 MHz, CDCl$_3$) δ 0.08 (3H, s), 0.09 (3H, s), 0.88 (9H, s), 1.26 (3H, d, J=6.2 Hz), 1.62 (9H, s), 2.91 (1H, dd, J=2.3 Hz and 5.2 Hz), 3.14–3.28 (1H, m), 3.45–3.57 (1H, m), 4.10–4.19 (1H, m), 4.19–4.29 (1H, m), 6.13 (1H, s), 7.52–7.61 (1H, m), 8.08–8.15 (1H, m), 8.18–8.26 (1H, m), 8.49–8.55 (1H, m).

Step b)

tert-Butyl 3-{[(2R,3S)-3-((1R)-1-{[tert-butyl(dimethyl)silyl]oxy}-ethyl)-4-oxo-2-azetidinyl]acetyl}benzoate (2.24 g) obtained in Step a) was dissolved in THF (20 ml), and thereto was added dropwise acetic acid (2.9 ml) at room temperature, and further thereto was added dropwise a solution of tetra-n-butylammonium fluoride (4.58 g) in THF (18 ml). The mixture was stirred at the same temperature for 3 days, and the reaction solution was diluted with ethyl acetate. The mixture was poured into a cold aqueous sodium hydrogen carbonate solution, and the mixture was extracted and separated. The organic layer was washed with brine, dried over anhydrous magnesium sulfate, and the solvent was evaporated under reduced pressure to give tert-butyl 3-({(2R,3S)-3-[(1R)-1-hydroxyethyl]-4-oxo-2-azetidinyl}acetyl)benzoate, which was used in the subsequent reaction without further purification.

Step c)

tert-Butyl 3-({(2R,3S)-3-[(1R)-1-hydroxyethyl]-4-oxo-2-azetidinyl}-acetyl)benzoate obtained in Step b) and 4-dimethylaminopyridine (1.34 g) were dissolved in dry methylene chloride (20 ml), and thereto was added dropwise allyl chloroformate (1.21 g) under ice-cooling. The mixture was warmed gradually to room temperature, and stirred for 5 hours. The reaction solution was diluted with ethyl acetate, and the mixture was poured into cold aqueous potassium hydrogen sulfate solution. The mixture was extracted and separated, and the organic layer was washed successively with an aqueous potassium hydrogen sulfate solution, brine, an aqueous sodium hydrogen carbonate solution, and brine, and dried over anhydrous magnesium sulfate. The solvent was removed under reduced pressure, and the resulting residue was purified by silica gel column chromatography (hexane/ethyl acetate) to give tert-butyl 3-{[(2R,3S)-3-((1R)-1-{[(allyloxy)carbonyl]oxy}ethyl)-4-oxo-2-azetidinyl]acetyl}benzoate (1.126 g).

$^1$H NMR (400 MHz, CDCl$_3$) δ 1.49 (3H, d, J=6.3 Hz), 1.63 (9H, s), 3.10 (1H, dd, J=2.3 Hz and 8.2 Hz), 3.16–3.28 (1H, m), 3.52–3.62 (1H, m), 4.07–4.16 (1H, m), 4.57–4.70 (2H, m), 5.09–5.20 (1H, m), 5.22–5.41 (2H, m), 5.87–6.00 (1H, m), 6.20 (1H, s), 7.52–7.60 (1H, m), 8.07–8.14 (1H, m), 8.18–8.25 (1H, m), 8.47–8.54 (1H, m).

Step d)

tert-Butyl 3-({(2R,3S)-3-((1R)-1-{[(allyloxy)carbonyl]oxy}ethyl)-1-[2-(allyloxy)-2-oxo-1-(triphenylphosphoranylidene)ethyl]-4-oxo-2-azetidinyl}acetyl)benzoate, (945 mg) was obtained from tert-butyl 3-{[(2R,3S)-3-((1R)-1-{[(allyloxy)carbonyl]oxy}ethyl)-4-oxo-2-azetidinyl]-acetyl}benzoate (1.026 g) obtained in Step c) in a similar manner to Reference Example 2-a).

IR (KBr) 1749, 1715, 1687, 755, 693 cm$^{-1}$

Step e)

3-({(2R,3S)-3-((1R)-1-{[(Allyloxy)carbonyl]oxy}ethyl)-1-[2-(allyloxy)-2-oxo-1-(triphenylphosphoranylidene)ethyl]-4-oxo-2-azetidinyl}acetyl)benzoic acid was obtained from tert-butyl 3-({(2R,3S)-3-((1R)-1-{[(allyloxy)carbonyl]oxy}ethyl)-1-[2-(allyloxy)-2-oxo-1-(triphenylphosphoranylidene)ethyl]-4-oxo-2-azetidinyl}acetyl)benzoate (889 mg) obtained in Step d) in a similar manner to Reference Example 2-b, which was used in the subsequent reaction without further purification.

Step f)

Allyl ((2R,3S)-3-((1R)-1-{[(allyloxy)carbonyl]oxy}ethyl)-2-{2-[3-(aminocarbonyl)phenyl]-2-oxoethyl}-4-oxo-1-azetidinyl)(triphenylphosphoranylidene)acetate (324 mg) was obtained from a half amount of 3-({(2R,3S)-3-((1R)-1-{[(allyloxy)carbonyl]oxy}ethyl)-1-[2-(allyloxy)-2-oxo-1-(triphenylphosphoranylidene)ethyl]-4-oxo-2-azetidinyl}acetyl)benzoic acid obtained in Step e) and a 28% aqueous ammonia solution in a similar manner to Reference Example 2-c).

IR (CHCl$_3$) 3413, 1746, 1679, 1614, 1260 cm$^{-1}$

Reference Example 4

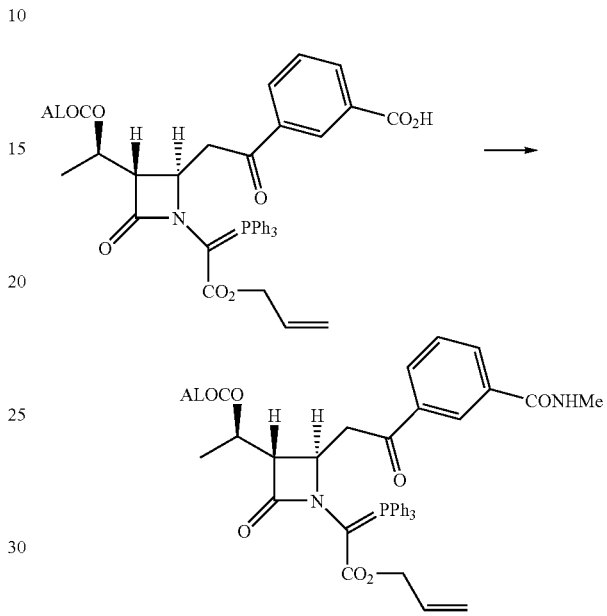

Allyl [(2R,3S)-3-((1R)-1-{[(allyloxy)carbonyl]oxy}ethyl)-2-(2-{3-[(methylamino)carbonyl]phenyl}-2-oxoethyl)-4-oxo-1-azetidinyl]-(triphenylphosphoranylidene)acetate was obtained from a solution of 3-({(2R,3S)-3-((1R)-1-{[(allyloxy)carbonyl]oxy}ethyl)-1-[2-(allyloxy)-2-oxo-1-(triphenylphosphoranylidene)ethyl]-4-oxo-2-azetidinyl}acetyl)benzoic acid and monomethylamine in 40% methanol in a similar manner to Reference Example 2-c).

IR (CHCl$_3$) 1746, 1661 cm$^{-1}$

Reference Example 5

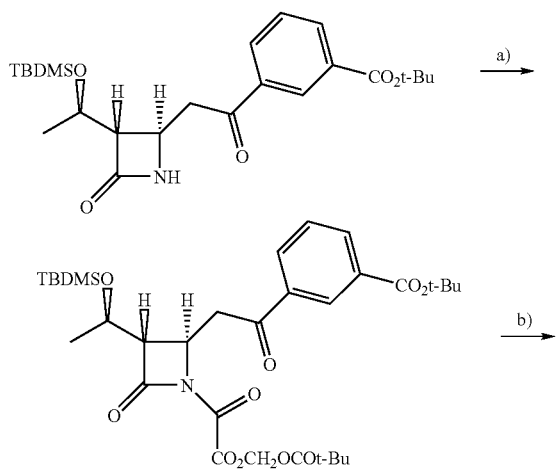

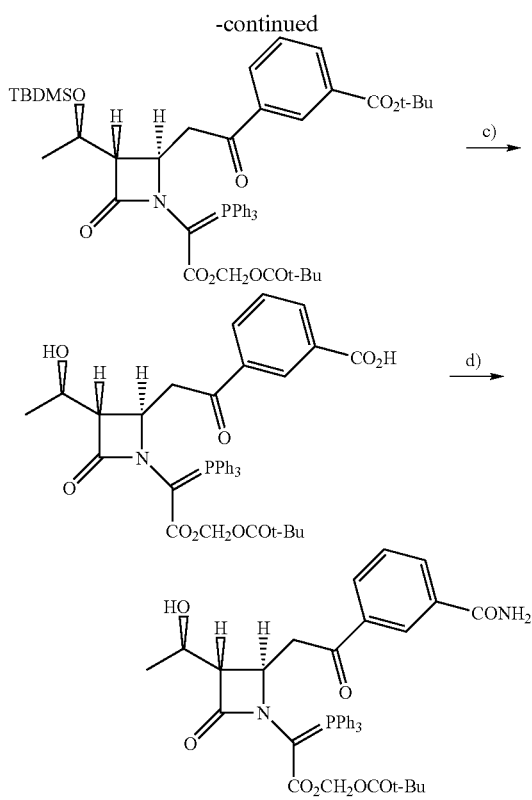

Step a)

tert-Butyl 3-{[(2R,3S)-3-((1R)-1-{[tert-butyl(dimethyl) silyl]oxy}-ethyl)-4-oxo-2-azetidinyl]acetyl}benzoate (2.24 g) and triethylamine (1.11 g) were dissolved in dry methylene chloride (10 ml), and thereto was added dropwise a solution of [(2-chloro-2-oxoacetyl)oxy]methyl pivalate (10 mmol) in dry methylene chloride (10 ml) under ice-cooling. The reaction was quenched by addition of saturated aqueous ammonium chloride solution. The mixture was extracted with ethyl acetate, and separated. The organic layer was washed successively with an aqueous sodium hydrogen carbonate solution and brine, dried over anhydrous magnesium sulfate, and the solvent was removed under reduced pressure. The residue was purified by silica gel column chromatography (hexane/ethyl acetate) to give tert-butyl 3-({(2R,3S)-3-((1R)-1-{[tert-butyl(dimethyl) silyl] oxy}ethyl)-1-[{[(2,2-dimethylpropanoyl)oxy]methoxy} (oxo)acetyl]-4-oxo-2-azetidinyl}acetyl)benzoate (3.152 g).

$^1$H NMR (400 MHz, CDCl$_3$) δ 0.03 (3H, s), 0.08 (3H, s), 0.85 (9H, s), 1.24 (9H, s), 1.29 (3H, d, J=6.4 Hz), 1.62 (9H, s), 3.15–3.31 (1H, m), 3.35–3.53 (1H, m), 3.89–4.04 (1H, m), 4.28–4.47 (1H, m), 4.77–5.41 (1H, m), 5.92 (2H, s), 7.49–7.64 (1H, m), 8.05–8.18 (1H, m), 8.18–8.30 (1H, m), 8.52 (1H, broad s).

Step b)

tert-Butyl 3-({(2R,3S)-3-((1R)-1-{[tert-butyl(dimethyl) silyl]oxy}-ethyl)-1-[{[(2,2-dimethylpropanoyl)oxy]methoxy}(oxo)acetyl]-4-oxo-2-azetidinyl}acetyl)benzoate (1.90 g) was dissolved in acetic acid (10 ml) and methylene chloride (10 ml), and thereto was added zinc powder (5.88 g) under ice-cooling. The mixture was vigorously stirred at the same temperature for 15 minutes, and the reaction solution was filtered on cerite and washed with chloroform. The filtrate and washings were combined, and washed with a cold aqueous sodium hydrogen carbonate solution (three times) and brine (once), and dried over anhydrous magnesium sulfate. The solvent was removed under reduced pressure to give a corresponding hemiacetal compound (1.923 g), which was further treated in a similar manner to Reference Example 2-a) to give tert-butyl 3-({(2R,3S)-3-((1R)-1-{[tert-butyl(dimethyl)silyl]oxy}ethyl)-1-[2-{[(2,2-dimethylpropanoyl)oxy]methoxy}-2-oxo-1-(triphenylphosphoranylidene)ethyl]-4-oxo-2-azetidinyl}acetyl)benzoate (1.706 g).

IR (KBr) 1748, 1718, 1689, 1641, 834, 753, 693 cm$^{-1}$

Step c)

3-({(2R,3S)-1-[2-{[(2,2-Dimethylpropanoyl)oxy]methoxy}-2-oxo-1-(triphenylphosphoranylidene)ethyl]-3-[(1R)-1-hydroxyethyl]-4-oxo-2-azetidinyl}acetyl)benzoic acid was obtained from tert-butyl 3-({(2R,3S)-3-((1R)-1-{[tert-butyl(dimethyl) silyl]oxy}ethyl)-1-[2-{[(2,2-dimethylpropanoyl)oxy]methoxy}-2-oxo-1-(triphenylphosphoranylidene)ethyl]-4-oxo-2-azetidinyl}acetyl)benzoate (1.50 g) in a similar manner to Reference Example 2-b), which was used in the subsequent reaction without further purification.

Step d)

{[2-{(2R,3S)-2-{2-[3-(Aminocarbonyl)phenyl]-2-oxoethyl}-3-[(1R)-1-hydroxyethyl]-4-oxo-1-azetidinyl}-2-(triphenylphosphoranylidene)acetyl]oxy}methyl pivalate was obtained from 3-({(2R,3S)-1-[2-{[(2,2-dimethylpropanoyl)oxy]methoxy}-2-oxo-1-(triphenylphosphoranylidene) ethyl]-3-[(1R)-1-hydroxyethyl]-4-oxo-2-azetidinyl}acetyl)benzoic acid in a similar manner to Reference Example 2-c).

IR (CHCl$_3$) 1744, 1676 cm$^{-1}$

Reference Example 6

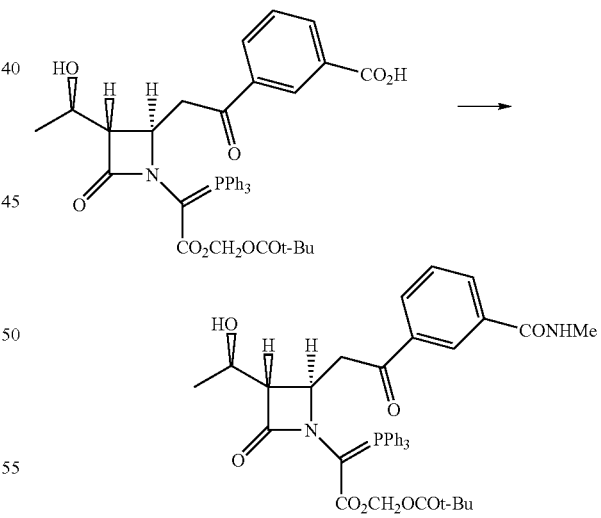

{[2-[(2R,3S)-3-[(1R)-1-Hydroxyethyl]-2-(2-{3-[(methylamino)carbonyl]phenyl}-2-oxoethyl]-4-oxo-1-azetidinyl]-2-(triphenylphosphoranylidene)acetyl]oxy}methyl pivalate was obtained from 3-({(2R,3S)-1-[2-{[(2,2-dimethylpropanoyl)oxy]methoxy}-2-oxo-1-(triphenylphosphoranylidene)ethyl]-3-[(1R)-1-hydroxyethyl]-4-oxo-2-azetidinyl}acetyl)benzoic acid in a similar manner to Reference Example 2-c).

IR (CHCl$_3$) 1745, 1660 cm$^{-1}$

Reference Example 7

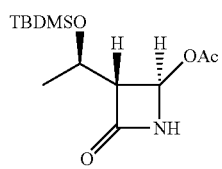

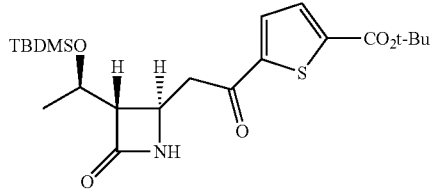

Tert-Butyl 5-{[(2R,3S)-3-((1R)-1-{[tert-butyl(dimethyl) silyl]oxy}-ethyl)-4-oxo-2 azetidinyl]acetyl}-2-thiophenecarboxylate was obtained from (2R,3R)-3-((1R)-1-{[tert-butyl(dimethyl) silyl]oxy}ethyl)-4-oxo-2-azetidinyl acetate in a similar manner to Reference Example 1.

$^1$H NMR (400 MHz, CDCl$_3$) δ 0.07 (3H, s), 0.08 (3H, s), 0.88 (9H, s), 1.24 (3H, d, J=6.2 Hz), 1.59 (9H, s), 2.89. (1H, dd, J=2.3 Hz and 5.2 Hz), 3.07–3.18 (1H, m), 3.34–3.43 (1H, m), 4.08–4.16 (1H, m), 4.17–4.27 (1H, m), 6.08 (1H, s), 7.61–7.73 (2H, m).

Reference Example 8

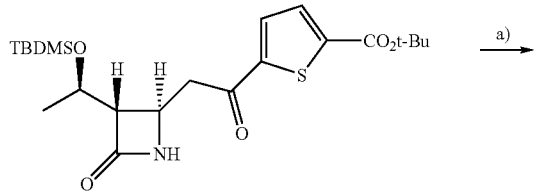

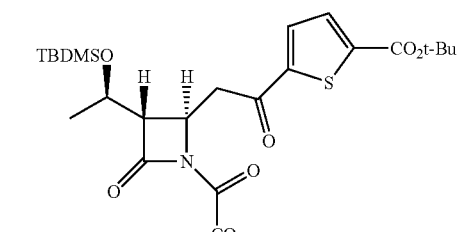

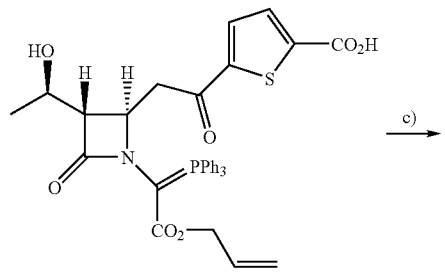

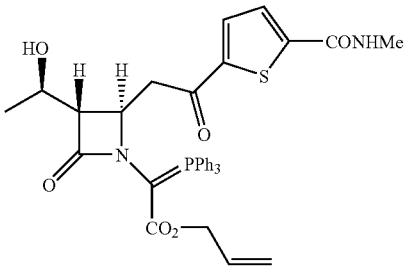

Allyl ((2R,3S)-2-(2-{5-[(methylamino)carbonyl]-2-thienyl}-2-oxoethyl)-4-oxo-3-{(1R)-1-l[(tri methylsilyl)oxy] ethyl}-1-azetidinyl)(triphenylphosphoranylidene)acetate was obtained from tert-butyl 5-{[(2R,3S)-3-((1R)-1-{[tert-butyl(dimethyl) silyl]oxy}ethyl)-4-oxo-2-azetidinyl]acetyl}-2-thiophenecarboxylate in a similar manner to Reference Example 2. This product was used in Example 8 without further purification.

Reference Example 9

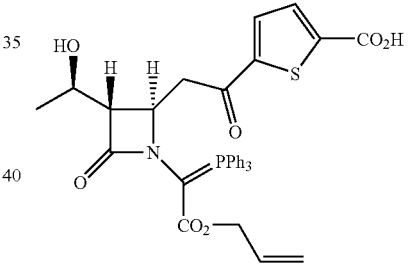

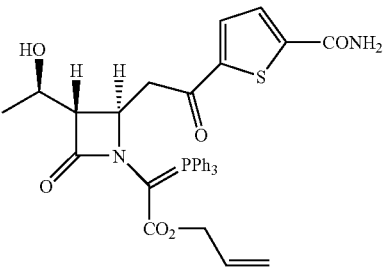

Allyl {(2R,3S)-2-{2-[5-(aminocarbonyl)-2-thienyl]-2-oxoethyl}-3-[(1R)-1-hydroxyethyl]-4-oxo-1-azetidinyl}(triphenylphosphoranylidene)acetate was obtained from 5-({(2R,3S)-1-[2-(allyloxy)-2-oxo-1-(triphenylphosphoranylidene)ethyl]-3-[(1R)-1-hydroxyethyl]-4-oxo-2-azetidinyl}-acetyl)-2-thiophenecarboxylate in a similar manner to Reference Example 2-c). This product was used in Example 7 without further purification.

Reference Example 10

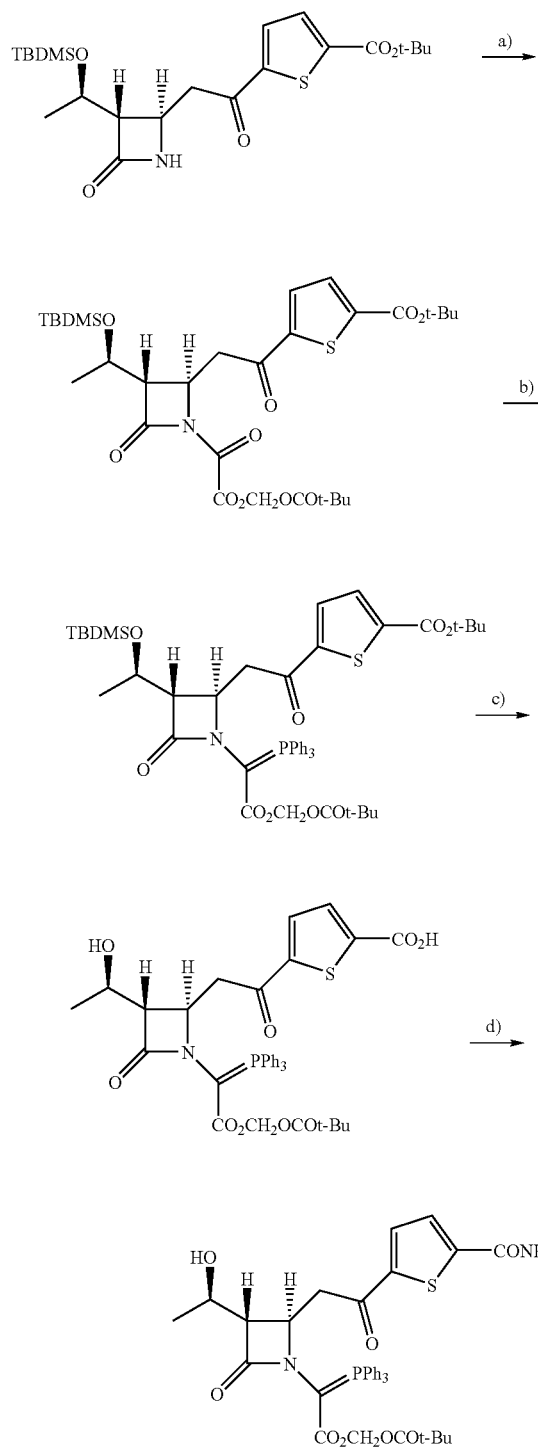

{2-[(2R,3S)-3-[(1R)-1-Hydroxyethyl]-2-(2-{5-[(methylamino)carbonyl]-2-thienyl}-2-oxoethyl)-4-oxo-1-azetidinyl]-2-(triphenylphosphoranylidene)acetyl]oxy}methyl pivalate was obtained from tert-butyl 5-{[(2R,3S)-3-((1R)-1-{[tert-butyl(dimethyl)silyl]oxy}ethyl)-4-oxo-2-azetidinyl]acetyl}-2-thiophenecarboxylate in a similar manner to Reference Example 5.

IR (CHCl$_3$) 3690 (broad), 1744, 1660, 1537 cm$^{-1}$

Reference Example 11

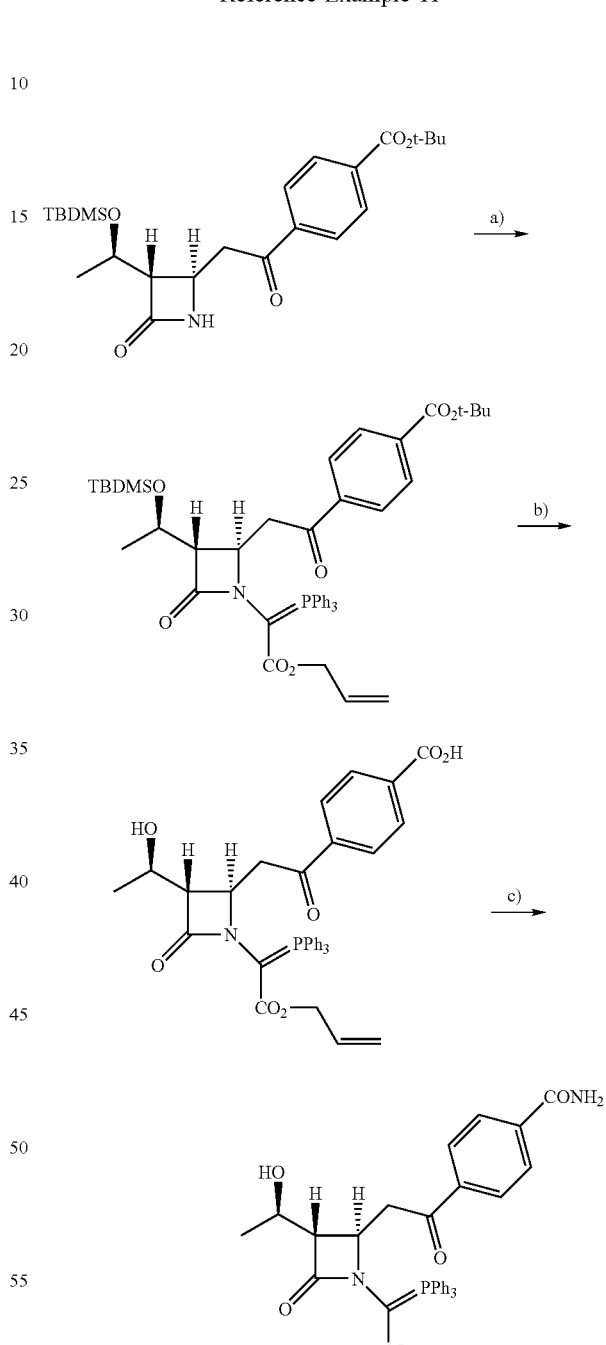

Allyl {(2R,3S)-2-{2-[4-(aminocarbonyl)phenyl]-2-oxoethyl}-3-[(1R)-1-hydroxyethyl]-4-oxo-1-azetidinyl}(triphenylphosphoranylidene)acetate was obtained from tert-butyl 4-{[(2R,3S)-3-((1R)-1-{[tert-butyl(dimethyl)silyl]oxy}ethyl)-4-oxo-2-azetidinyl]acetyl}benzoate in a similar manner to Reference Example 2.

IR (KBr) 3418 (broad), 1744, 1675, 1619, 1202, 751, 720, 692 cm$^{-1}$

Reference Example 12

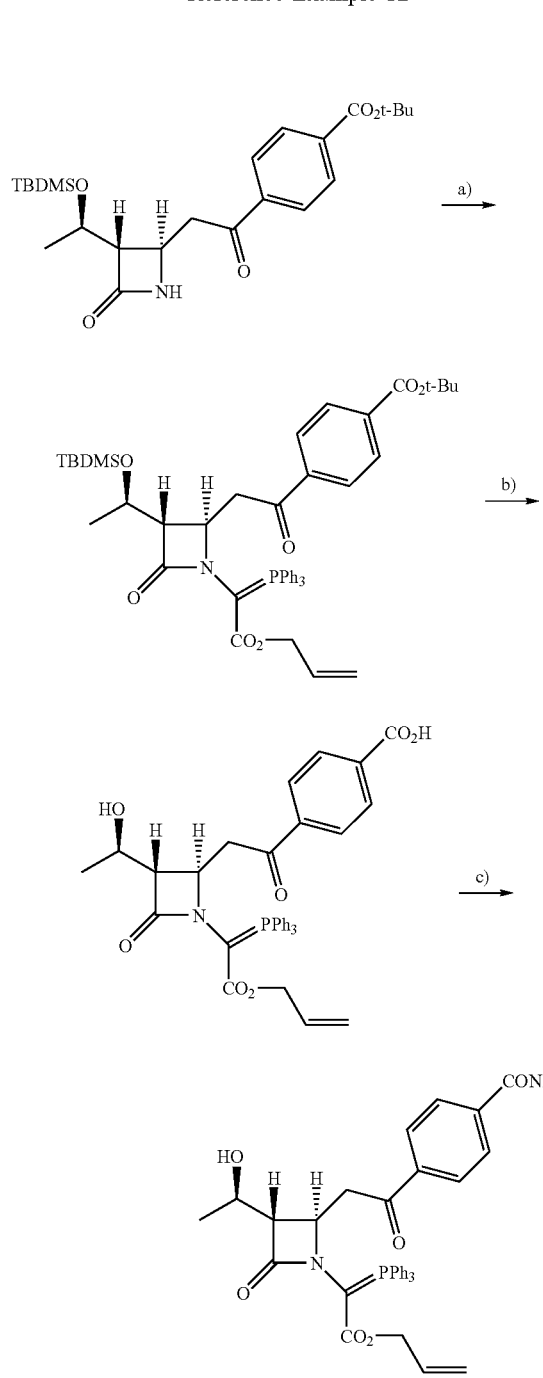

Allyl {(2R,3S)-2-{2-[4-(ethylaminocarbonyl)phenyl]-2-oxoethyl}-3-[(1R)-1-hydroxyethyl]-4-oxo-1-azetidinyl}(triphenylphosphoranylidene)acetate was obtained from tert-butyl 4-{[(2R,3S)-3-((1R)-1-{[tert-butyl(dimethyl)silyl]oxy}ethyl)-4-oxo-2-azetidinyl]acetyl}benzoate in a similar manner to Reference Example 2.

IR (KBr) 3408 (broad), 1733, 1641, 1106, 754, 720, 693 cm$^{-1}$

Reference Example 13

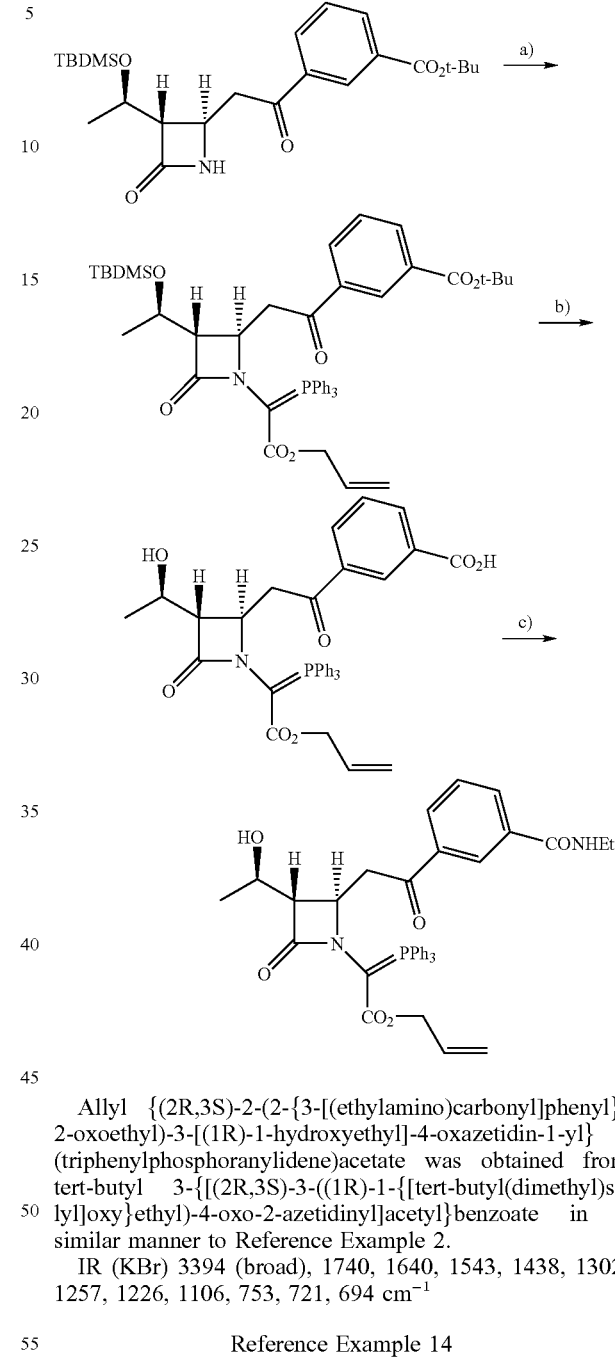

Allyl {(2R,3S)-2-(2-{3-[(ethylamino)carbonyl]phenyl}-2-oxoethyl)-3-[(1R)-1-hydroxyethyl]-4-oxazetidin-1-yl}(triphenylphosphoranylidene)acetate was obtained from tert-butyl 3-{[(2R,3S)-3-((1R)-1-{[tert-butyl(dimethyl)silyl]oxy}ethyl)-4-oxo-2-azetidinyl]acetyl}benzoate in a similar manner to Reference Example 2.

IR (KBr) 3394 (broad), 1740, 1640, 1543, 1438, 1302, 1257, 1226, 1106, 753, 721, 694 cm$^{-1}$ Reference Example 14

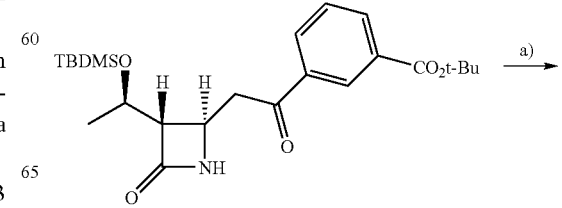

-continued

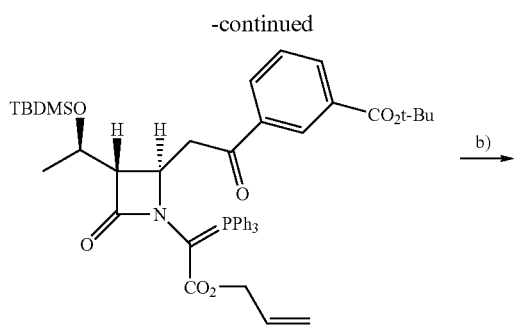

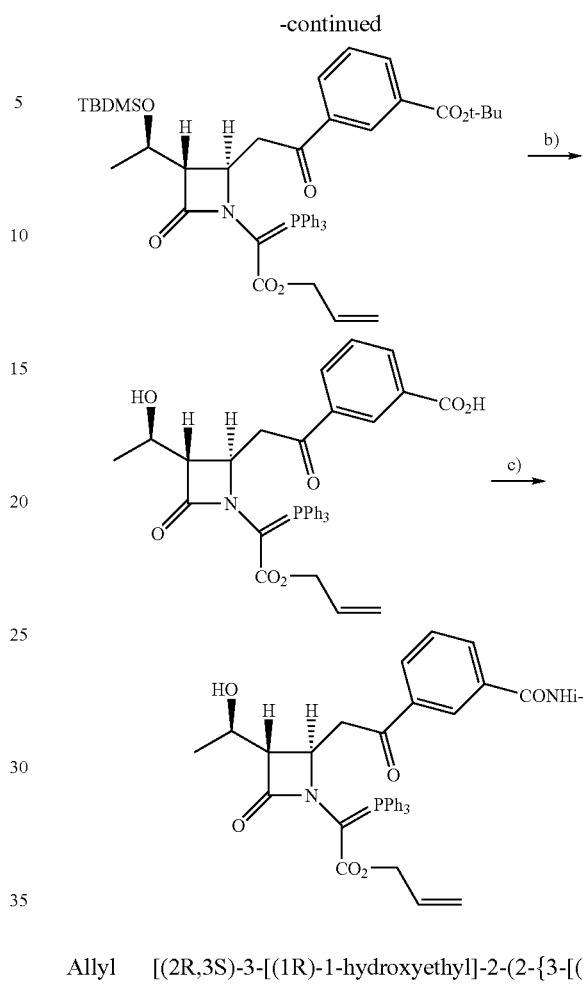

Allyl [(3S,4R)-3-[(1R)-1-hydroxyethyl]-2-oxo-4-(2-oxo-2-{3-[(propylamino)carbonyl]phenyl}ethyl)azetidin-1-yl](triphenylphosphoranylidene)acetate was obtained from tert-butyl 3-{[(2R,3S)-3-((1R)-1-{[tert-butyl(dimethyl)silyl]oxy}ethyl)-4-oxo-2-azetidinyl]acetyl}benzoate in a similar manner to Reference Example 2.

IR (KBr) 3372 (broad), 2969, 2931, 1735, 1640, 1542, 1438, 1304, 1255, 1227, 1107, 752, 720, 694 cm$^{-1}$ Reference Example 15

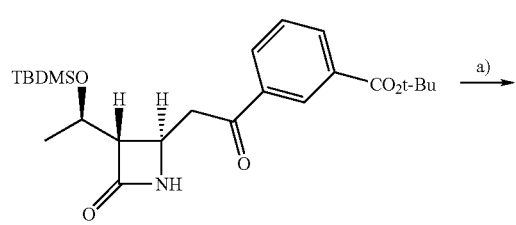

Allyl [(2R,3S)-3-[(1R)-1-hydroxyethyl]-2-(2-{3-[(isopropylamino) carbonyl]phenyl}-2-oxoethyl)-4-oxoazetidin-1-yl] (triphenylphosphoranylidene)acetate was obtained from tert-butyl 3-{[(2R,3S)-3-((1R)-1-{[tert-butyl(dimethyl) silyl]oxy}ethyl)-4-oxo-2-azetidinyl]acetyl}-benzoate in a similar manner to Reference Example 2.

IR (KBr) 3340 (broad), 2975, 2932, 1739, 1636, 1540, 1438, 1256, 1228, 1107, 753, 719, 693 cm$^{-1}$ Reference Example 16

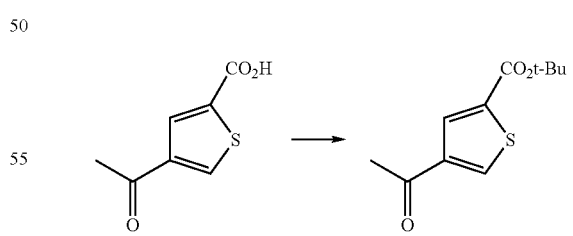

4-Acetylthiophene-2-carboxylic acid, which was obtained according to the literature (Bull., Chem. Soc. Jpn., 56, 2463 (1983)), was esterified by the well-known method disclosed in the literature (J. Org. Chem., 47, 1962 (1982)) to give tert-butyl 4-acetylthiophene-2-carboxylate.

$^1$H NMR (400 MHz, CDCl$_3$) δ 1.58 (s, 9H), 2.53 (s, 3H), 8.06 (d, 1H, J=1.2 Hz), 8.15 (d, 1H, J=1.2 Hz).

Reference Example 17

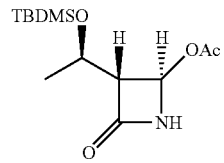

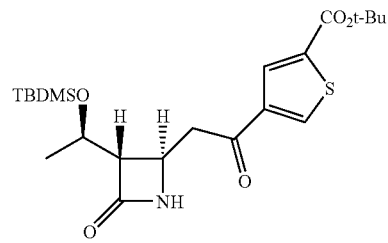

tert-Butyl 4-{[(2R,3S)-3-((1R)-1-{[tert-butyl(dimethyl)silyl]oxy}-ethyl)-4-oxoazetidin-2-yl]acetyl}thiophene-2-carboxylate was obtained from tert-butyl 4-{[(trimethylsilyl)oxy]vinyl}thiophene-2-carboxylate, which was obtained from tert-butyl 4-acetylthiophene-2-carboxylate by the well-known method disclosed in the literature (Synthesis, 1977, 91), and (2R,3R)-3-((1R)-1-{[tert-butyl(dimethyl)silyl]oxy}ethyl)-4-oxo-2-azetidinyl acetate in a similar manner to Reference Example 1.

IR (KBr) 2968, 2930, 1760, 1712, 1686, 1534, 1370, 1275, 1256, 1157, 836, 778 cm$^{-1}$

Reference Example 18

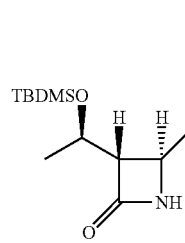

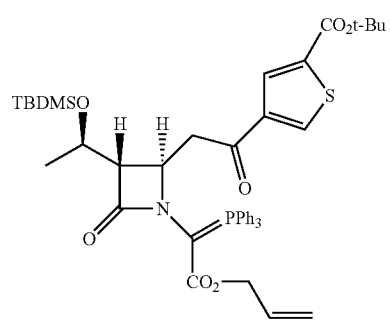

-continued

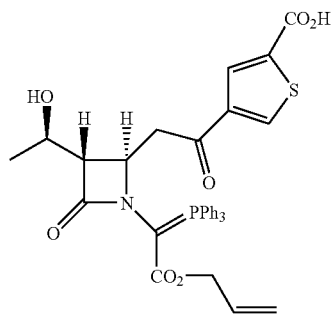

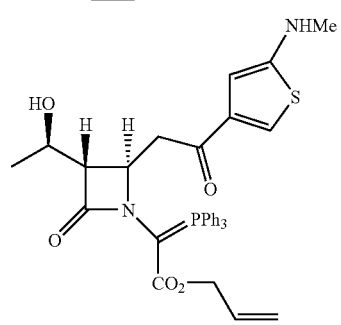

Allyl [(2R,3S)-3-[(1R)-1-hydroxyethyl]-2-(2-{5-[(methylamino)carbonyl]thien-3-yl}-2-oxoethyl)-4-oxoazetidin-1-yl](triphenylphosphoranylidene)acetate was obtained from tert-butyl 4-{[(2R,3S)-3-((1R)-1-{[tert-butyl(dimethyl)silyl]oxy}ethyl)-4-oxoazetidin-2-yl]acetyl}-thiophene-2-carboxylate in a similar manner to Reference Example 2.

IR (KBr) 3426 (broad), 2934, 1734, 1634, 1558, 1438, 1412, 1307, 1255, 1107, 754, 719, 694 cm$^{-1}$

Reference Example 19

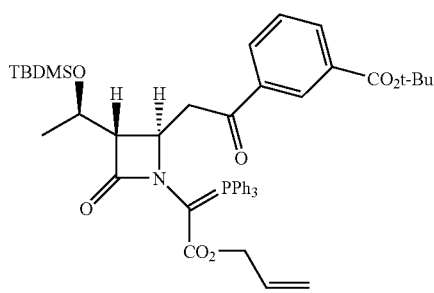

-continued

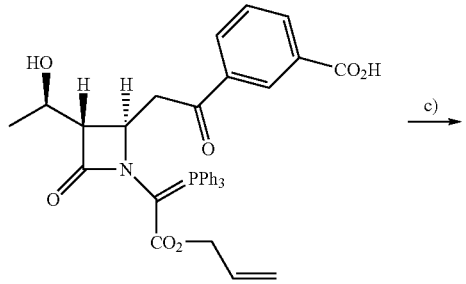

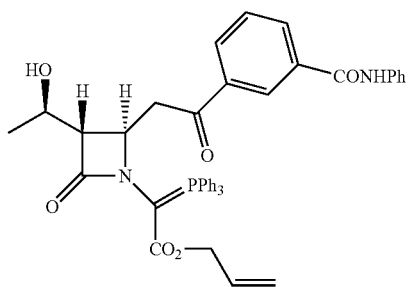

Allyl {(2R,3S)-2-{2-[3-(anilinocarbonyl)phenyl]-2-oxo-ethyl}-3-[(1R)-1-hydroxyethyl]-4-oxoazetidin-1-yl}(triphenylphosphoranylidene)acetate was obtained from tert-butyl 3-{[(2R,3S)-3-((1R)-1-{[tert-butyl(dimethyl)silyl]oxy}ethyl)-4-oxo-2-azetidinyl]acetyl}benzoate in a similar manner to Reference Example 2.

IR (KBr) 3427 (broad), 1736, 1673, 1621, 1601, 1541, 1440, 1243, 1106, 754, 693 cm$^{-1}$ Reference Example 20

-continued

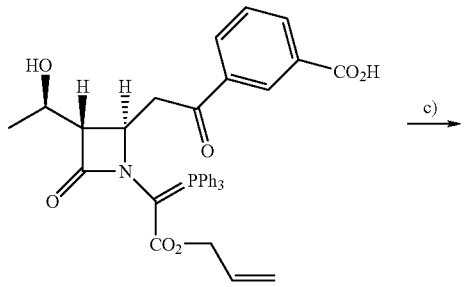

Allyl ((2R,3S)-3-[(1R)-1-hydroxyethyl]-2-{2-[3-(morpholin-4-ylcarbonyl)phenyl]-2-oxoethyl}-4-oxoazetidin-1-yl) (triphenylphosphoranylidene)acetate was obtained from tert-butyl 3-{[(2R,3S)-3-((1R)-1-{[tert-butyl(dimethyl)silyl]oxy}ethyl)-4-oxo-2-azetidinyl]acetyl}-benzoate in a similar manner to Reference Example 2.

IR (KBr) 3445 (broad), 2970, 1742, 1684, 1635, 1438, 1109 cm$^{-1}$

Reference Example 21

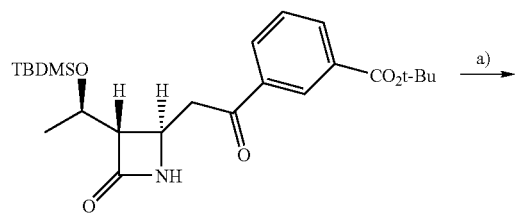

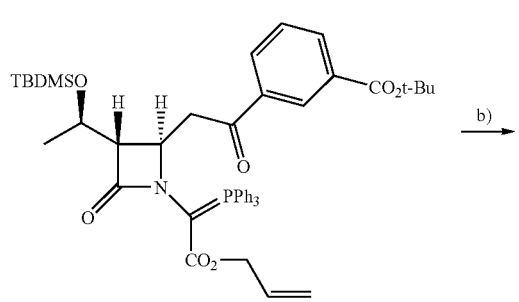

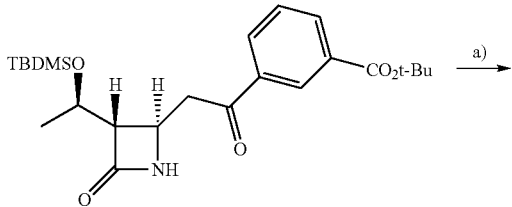

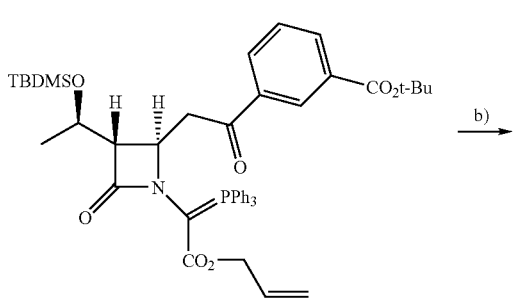

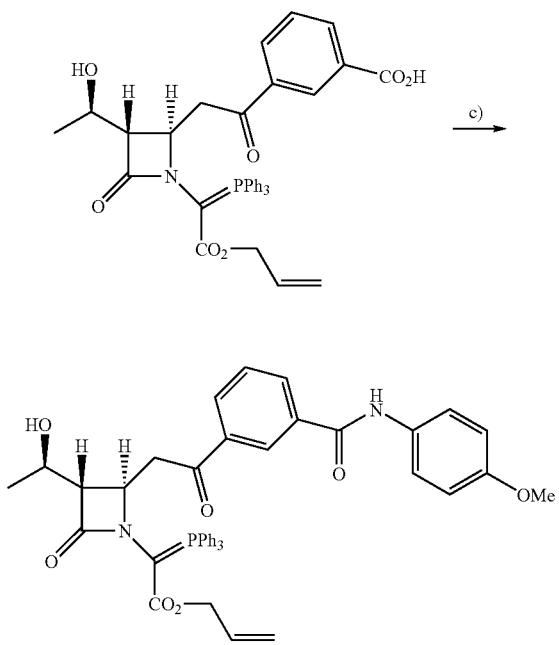

Allyl {(2R,3S)-3-[(1R)-1-hydroxyethyl]-2-[2-(3-{[(4-methoxyphenyl)amino]carbonyl}phenyl)-2-oxoethyl]-4-oxoazetidin-1-yl}(triphenylphosphoranylidene)acetate was obtained from tert-butyl 3-{[(2R,3S)-3-((1R)-1-{[tert-butyl(dimethyl) silyl]oxy}ethyl)-4-oxo-2-azetidinyl]acetyl}-benzoate in a similar manner to Reference Example 2.

IR (KBr) 3423 (broad), 3065, 2930, 1739, 1620, 1512, 1438, 1411, 1299, 1244, 1107, 756, 694 cm$^{-1}$ Reference Example 22

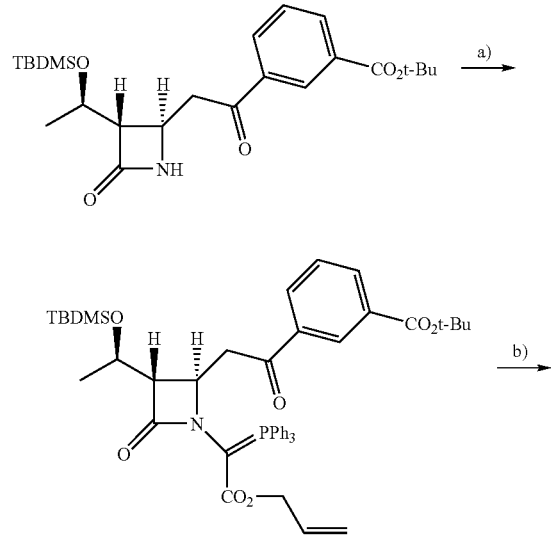

Allyl [(3S,4R)-3-[(1R)-1-hydroxyethyl]-2-oxo-4-(2-oxo-2-{3-[(pyridin-4-ylamino)carbonyl]phenyl}ethyl)azetidin-1-yl](triphenylphosphoranylidene)acetate was obtained from tert-butyl 3-{[(2R,3S)-3-((1R)-1-{[tert-butyl(dimethyl) silyl]oxy}ethyl)-4-oxo-2-azetidinyl]acetyl}-benzoate in a similar manner to Reference Example 2.

IR (KBr) 3418 (broad), 3077, 2971, 1734, 1685, 1597, 1512, 1438, 1332, 1298, 1212, 1107, 694 cm$^{-1}$ Reference Example 23

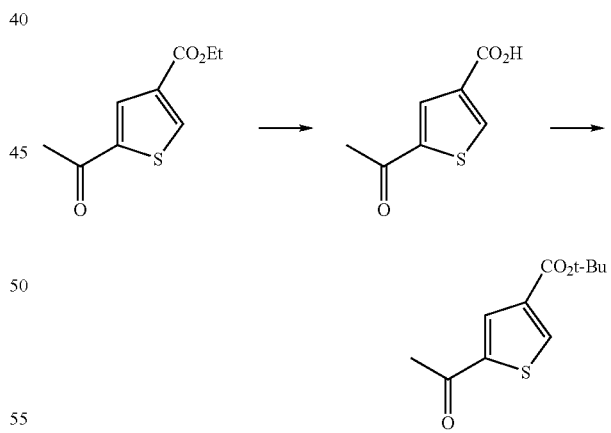

Ethyl 5-acetylthiophene-3-carboxylate (J. Org. Chem., 37, 2615(1972)) was hydrolyzed by the well-known method disclosed in the literature (Chem. Pharm. Bull., 48, 2003 (2000)) to give 5-acetylthiophene-3-carboxylic acid, which was further treated in a similar manner to Reference Example 16 to give tert-butyl 5-acetylthiophene-3-carboxylate.

$^1$H NMR (400 MHz, CDCl$_3$) δ 1.58 (s, 9H), 2.58 (s, 3H), 8.00 (d, 1H, J=1.2 Hz), 8.24 (d, 1H, J=1.2 Hz).

Reference Example 24

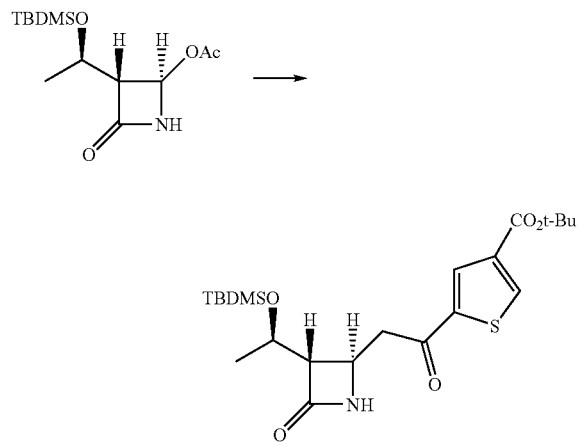

tert-Butyl 5-{[(2R,3S)-3-((1R)-1-{[tert-butyl(dimethyl)silyl]oxy}-ethyl}-4-oxoazetidin-2-yl}acetyl}thiophene-3-carboxylate was obtained from tert-butyl 5-{1-[(trimethylsilyl)oxy]vinyl}thiophene-3-carboxylate, which was obtained by the well-known method disclosed in the literature (Synthesis, 1977, 91), and (2R,3R)-3-((1R)-1-{[tert-butyl(dimethyl)silyl]oxy}ethyl)-4-oxo-2-azetidinyl acetate in a similar manner to Reference Example 1.

$^1$H NMR (400 MHz, CDCl$_3$) δ 0.07 (s, 3H), 0.08 (s, 3H), 0.87 (s, 9H), 1.24 (d, 3H, J=6.2 Hz), 1.59 (s, 9H), 2.89–2.91 (m, 1H), 3.10–3.16 (m, 1H), 3.37–3.42 (m, 1H), 4.09–4.13 (m, 1H), 4.21–4.23 (m, 1H), 6.09 (s, 1H), 8.01 (d, 1H, J=1.2 Hz), 8.29 (d, 1H, J=1.2 Hz).

Reference Example 25

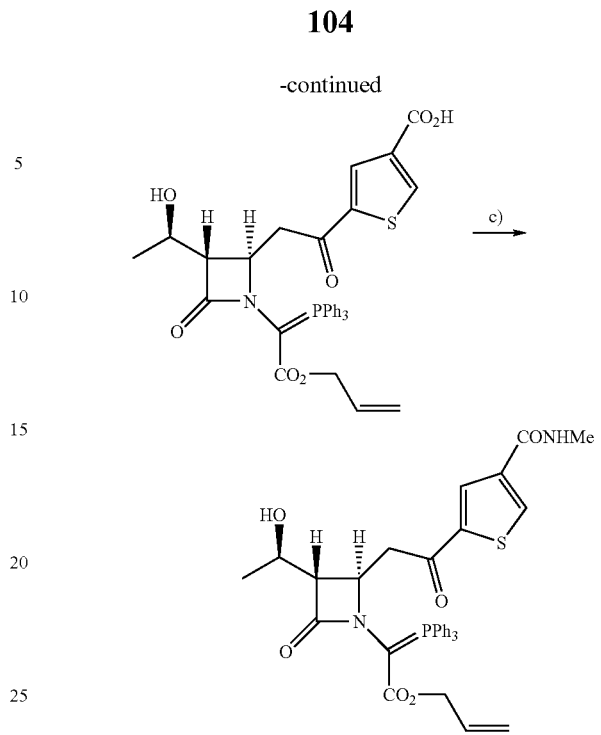

Allyl [(2R,3S)-3-[(1R)-1-hydroxyethyl]-2-(2-{4-[(methylamino)carbonyl]thien-2-yl}-2-oxoethyl)-4-oxoazetidin-1-yl](triphenylphosphoranylidene)acetate was obtained from tert-butyl 5-{[(2R,3S)-3-((1R)-1-{[tert-butyl(dimethyl)silyl]oxy}ethyl)-4-oxoazetidin-2-yl]acetyl}-thiophene-3-carboxylate in a similar manner to Reference Example 2.

IR (KBr) 3335 (broad), 3083, 1734, 1651, 1560, 1438, 1296, 1258, 1192, 753, 693 cm$^{-1}$

Reference Example 26

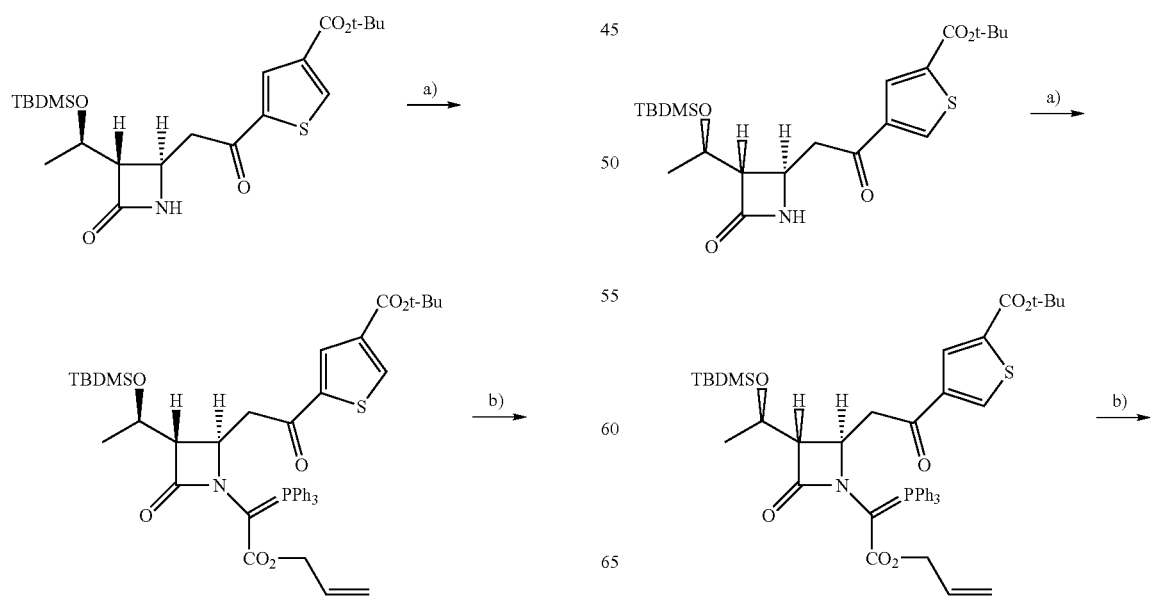

-continued

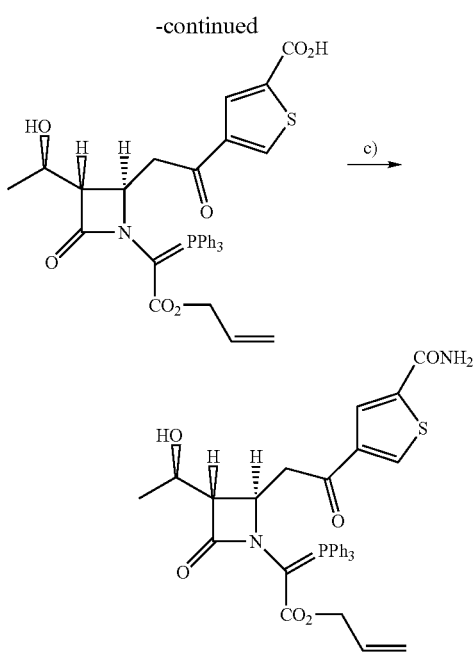

Allyl {(2R,3S)-2-{2-[5-(aminocarbonyl)thien-3-yl]-2-oxoethyl}-3-[(1R)-1-hydroxyethyl]-4-oxoazetidin-1-yl} (triphenylphosphoranylidene)acetate was obtained from tert-butyl 4-{[(2R,3S)-3-((1R)-1-{[tert-butyl(dimethyl)silyl]oxy}ethyl)-4-oxoazetidin-2-yl]acetyl}thiophene-2-carboxylate in a similar manner to Reference Example 2.

IR (KBr) 3412 (broad), 2973, 1735, 1668, 1612, 1439, 1107, 754, 694 cm$^{-1}$

INDUSTRIAL APPLICABILITY

By the present invention, it becomes possible to provide a β-lactam antibiotic with a high oral absorbability showing an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*.

What is claimed is:
1. A carbapenem compound of the formula:

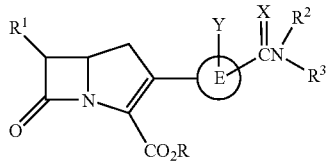

wherein Ring E is a benzene ring;
R$^1$ is an alkyl having 1 to 3 carbon atoms or a hydroxy-substituted alkyl having 1 to 3 carbon atoms;
R$^2$ is a hydrogen atom, and R$^3$ is an optionally substituted lower alkyl, or an optionally substituted aryl;

R is a hydrogen atom, or a group of the formula:

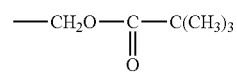

X is an oxygen atom or a sulfur atom;
Y is a hydrogen atom;
or a pharmaceutically acceptable salt thereof.

2. The carbapenem compound according to claim 1, or a pharmaceutically acceptable salt thereof, wherein R$^1$ is a 1-hydroxyethyl.

3. The carbapenem compound according to claim 1, or a pharmaceutically acceptable salt thereof, wherein the group of the formula:

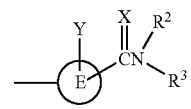

is a group selected from the following formula:

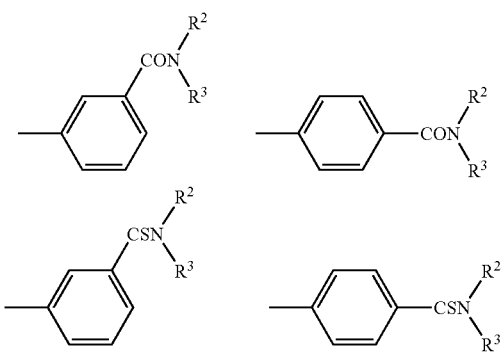

in which Ring E, R$^2$, R$^3$ and Y are as defined in claim 1.

4. The carbapenem compound according to claim 1, or a pharmaceutically acceptable salt thereof, wherein R$^2$ is a hydrogen atom and R$^3$ is a methyl group.

5. A carbapenem compound selected from the following compounds or a pharmaceutically acceptable salt thereof:

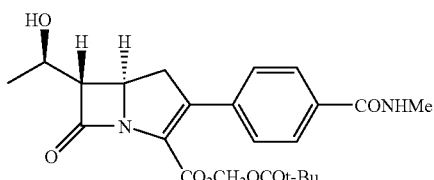

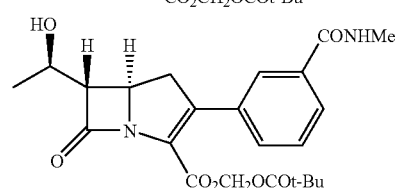

-continued

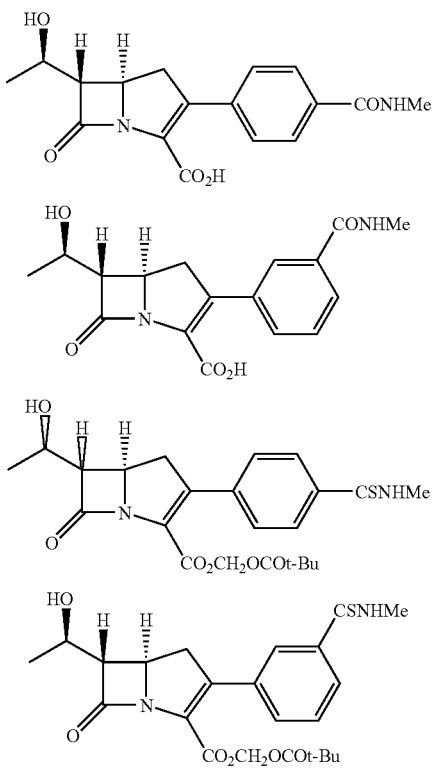

-continued

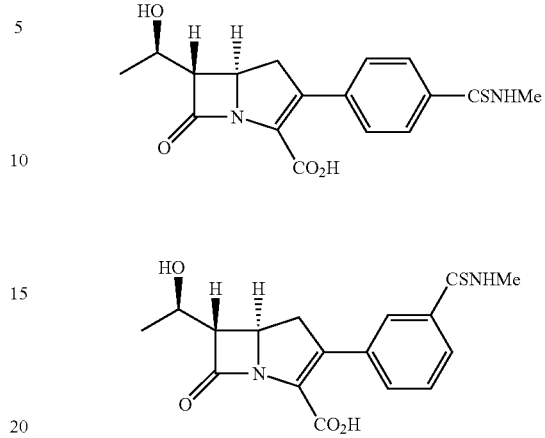

6. A pharmaceutical composition, which comprises as an active ingredient a carbapenem compound as set forth in claim 1 or a pharmaceutically acceptable salt thereof and a pharmaceutically acceptable carrier.

7. A method for the treatment of bacterial infections, which comprises the administration to a mammal of an effective amount of a carbapenem compound as set forth in claim 1 or a pharmaceutically acceptable salt thereof.

* * * * *